US011186807B2

(12) United States Patent
Verstrepen et al.

(10) Patent No.: US 11,186,807 B2
(45) Date of Patent: Nov. 30, 2021

(54) REDUCING ACETATE ESTER PRODUCTION IN YEAST

(71) Applicants: VIB VZW, Ghent (BE); KATHOLIEKE UNIVERSITEIT LEUVEN, K.U. LEUVEN R&D, Leuven (BE)

(72) Inventors: Kevin Verstrepen, Leuven (BE); Jan Steensels, Lommel (BE)

(73) Assignees: VIB VZW, Ghent (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 16/481,951

(22) PCT Filed: Jan. 29, 2018

(86) PCT No.: PCT/EP2018/052084
§ 371 (c)(1),
(2) Date: Jul. 30, 2019

(87) PCT Pub. No.: WO2018/138313
PCT Pub. Date: Aug. 2, 2018

(65) Prior Publication Data
US 2019/0352677 A1 Nov. 21, 2019

(30) Foreign Application Priority Data
Jan. 30, 2017 (EP) ..................................... 17153814

(51) Int. Cl.
| | | |
|---|---|---|
| *C12P 7/04* | (2006.01) | |
| *C12P 7/06* | (2006.01) | |
| *C12P 7/62* | (2006.01) | |
| *C12N 1/19* | (2006.01) | |
| *C12N 9/60* | (2006.01) | |
| *C12G 3/00* | (2019.01) | |
| *C07K 14/395* | (2006.01) | |
| *C12G 3/02* | (2019.01) | |
| *C12N 1/16* | (2006.01) | |

(52) U.S. Cl.
CPC .............. *C12G 3/00* (2013.01); *C07K 14/395* (2013.01); *C12G 3/02* (2013.01); *C12N 1/16* (2013.01); *C12P 7/06* (2013.01)

(58) Field of Classification Search
None
See application file for complete search history.

(56) References Cited

FOREIGN PATENT DOCUMENTS

WO 2007097091 A1 8/2007

OTHER PUBLICATIONS

Donnini et al., "Allelism of IMPJ and GAL2 Genes of *Saccharomyces cerevisiae*", J. Bacteriol. 174:3411-3415, 1992 (Year: 1992).*
Steensels et al., Appl. Environ. Microbiol. 80:6965-6975, 2014 (Year: 2014).*
Esser et al., Mol. Gen. Genomics 271:616-626, 2004 (Year: 2004).*
Meersman et al., "Tuning Chocolate Flavor through Development of Thermotolerant *Saccharomyces cerevisiae* Starter Cultures with Increased Acetate Ester Production", Appl. Envrion. Microbiol. 82:732-746, 2016 (Year: 2016).*
Database UniProt [Online] 1,3-6 Jun. 26, 2013 (Jun. 26, 2013). RecName: Full=Mitochondrial inner membrane protease subunit {EC0:0000256:RuleBase:RU362041}; EC=3.4.21.-{ECO:0000256:RuleBase:RU362041}; XP002779501, retrieved from EBI accession No. UNIPROT:N1NYG6 Database accession No. NINYG6 the whole document.
Database USPTO Proteins [Online] Feb. 7, 2008 (Feb. 7, 2008), "Sequence 1892 from U.S. Pat. No. 7,314,974.", XP002779502, retrieved from EBI accession No. USPOP:ABZ27954, Database accession No. ABZ27954 the whole document.
Jan et al., "Som1, a third component of the yeast mitochondrial inner membrane peptidase complex that contains Imp1 and Imp2", Molecular and General Genetics., vol. 263, No. 3, Apr. 25, 2000 (Apr. 25, 2000), pp. 483-491, XP055462055, DE ISSN: 0026-8925, DOI:10.1007/s004380051192, p. 484 col. 2 par.2.
Lodolo et al., "Evidence of Antimycin-Insensitive Respiration in a Commercial Brewing Yeast", Jan. 1, 1978 (Jan. 1, 1978), pp. 35-43, XP055462260, United States ISBN: 978-0-12-071250-2, Retrieved from the Internet: URL: https://onlinelibrary.wiley com/doi/pdf/10.1002/j.2050-0416.1999.tb00003.x [retrieved on Mar. 23, 2018], p. 40 col. 2 par. 2-p. 41 col. 1 par. I, Tb I, IV.
PCT International Search Report and Written Opinion, Application No. PCT/EP2018/052084, dated Jun. 18, 2018, 18 pages.
Verstrepen et al., Expression levels of the yeast alcohol acetyltransferase genes ATFI, Lg-ATFI, and ATF2 control the formation of a broad range of volatile esters. Applied and Environmental Microbiology, American Society for Microbiology, US, vol. 69, No. 9, Sep. 1, 2003 (Sep. 1, 2003), pp. 5228-5237, XP002421479, ISSN: 0099-2240, DOI:10.1128/AEM.69.9.5228-5237.2003 cited in the application p. 5229 col. 2 par.4, p. 5233 col. 2 par.3, p. 5234 col. 2 par.3.
Yang, Yudi, et al. "QTL Analysis of High Thermotolerance with Superior and Downgraded Parental Yeast Strains Reveals New Minor QTLs and Converges on Novel Causative Alleles Involved in RNA Processing." PLOS Genetics (2013) vol. 9 No. 8, e1003693, 15 pgs.

* cited by examiner

*Primary Examiner* — David Steadman
(74) *Attorney, Agent, or Firm* — Patent Law Works, LLP

(57) ABSTRACT

The present invention relates to the field of fermentation, more particularly to ethanol production. Even more particularly the present invention relates to reduced aroma production during fermentation processes. The present invention provides mutant alleles and chimeric genes useful to develop yeast strains to limit acetate ester levels during fermentation. In addition, the invention also relates to the use of such yeast strains as well as of compounds for the production of fermented foods and liquids with reduced acetate ester levels.

9 Claims, 10 Drawing Sheets
Specification includes a Sequence Listing.

REDUCING ACETATE ESTER PRODUCTION IN YEAST

FIELD OF THE INVENTION

The present invention relates to the field of fermentation, more particularly to ethanol production. Even more particularly the present invention relates to reduced aroma production during fermentation processes. The present invention provides mutant alleles and chimeric genes useful to develop yeast strains to limit acetate ester levels during fermentation. In addition, the invention also relates to the use of such yeast strains as well as of compounds for the production of fermented foods and liquids with reduced acetate ester levels.

Pursuant to 37 C.F.R. § 1.821(c), an ASCII text file of the Sequence Listing has been submitted concomitant with this application, the contents of which are hereby incorporated by reference. The ASCII text file is entitled "08174U5_2019-07-30_SequenceListing.txt" which is 18375 Bytes and was created on Jul. 24, 2019.

BACKGROUND

Microbes produce a wide spectrum of secondary metabolites. Many of these metabolites are volatile and have a strong aroma, contributing significantly to the overall flavour of fermented foods and beverages such as cheese, chocolate, wine, sake and beer. As yeast, and more specificallySaccharomyces cerevisiae, is the main workhorse in many of these fermentation processes, much of the research on microbial aroma production has been devoted to this model organism, often from an industrial point of view. Among the various aroma compounds produced by yeasts, a particularly interesting group are the volatile esters. These esters are generally accepted as important contributors to the flavour and aroma of alcoholic beverages, imparting fruity and flowery notes to the product (Verstrepen et al. 2003 Journal of Bioscience and Bioengineering 96: 110-118). During industrial fermentations, yeasts produce esters in very low concentrations, as low as a few parts per million (ppm) or even billion (ppb). Incidentally, these concentrations hover around the flavour threshold for humans (Engan 1972 Journal of the Institute of Brewing 78:33-36). Therefore, even very small changes in ester production can significantly alter a products' perception. Additionally, there is a strong interaction between the perception of different esters and synergistic effects are at play. Therefore, in a mixture of compounds (such as fermented beverages), some compounds can highlight or mask the presence of others. However, an excess of esters often result in an unpalatable product. For example, the flavour of ethyl acetate, which, in high concentrations, is described as "chemical" or "nail polish remover", is regarded as one of the most important off-flavours in fermented beverages (Pires et al. 2014 Appl Microbiol Biotechnol 98:1937-1949). Unfortunately, novel brewing techniques, such as very high gravity (VHG) brewing, unwantedly increase ester production to undesired levels (Verstrepen et al. 2003 Journal of Bioscience and Bioengineering 96:110-118). Post-fermentation removal of aroma compounds is feasible, but these are often technically challenging and/or cost-ineffective and therefore commercially not viable. Therefore, it would thus be advantageous to develop efficient and cost-effective approaches to reduce the level of off-flavours such as ethyl acetate during fermentation processes, more particularly during beer and wine production, or during the production of ethanol to be used in fortified alcoholic beverages.

One such approach is to regulate the formation of volatile esters during the fermentation process. This can be achieved by changing fermentation parameters or alternatively by using newly developed yeast strains that have a reduced inherent capacity to produce esters. Given the importance of acetate esters on beer and wine quality, most studies that have tried to unravel the parameters influencing the ester formation have done so from an industrial perspective. As a result, the effect of many factors is known, but the underlying signal transduction pathways are not always fully understood. For example, it was found that oxygenation (i.e. the supply of oxygen) during fermentation of the wort at high specific gravity can prevent excessive synthesis of ethyl acetate and isoamyl acetate (Anderson and Kirsop, 1975, J Inst Brew 81:111-115), but this was never investigated in detail. Also, it was initially believed that precursor concentration of acetate esters (i.e. acetyl-CoA and fusel alcohol) was the main rate-limiting factor in acetate ester production. However, more recent research showed that enzyme activity has a more decisive role (Verstrepen et al. 2003 Appl Environ Microbiol 69:5228-5237; Lilly et al. 2006 Yeast 23:641-659). Indeed, for acetate esters, which belong to the quantitatively most prominent group of esters produced by Saccharomyces, various overexpression and deletion experiments identified the alcohol acetyl transferase ATF1 and ATF2 as the most decisive enzymes involved in ester production (Fujii et al. 1996 Yeast 6: 593-598, Verstrepen et al. 2003 App Environ Microbiol 69:5228-5237). Deletion of the ATF1 gene typically results in an 80% reduction in isoamyl acetate (IA) production and a 30% decrease for ethyl acetate (Verstrepen et al. 2003 Appl Environ Microbiol 69:5228-5237). Consequently, many environmental factors that affect alcohol acetyl transferase activity also affect ester formation. The most effective (or at least industrially most relevant) repressors of Atf1 expression are oxygen and unsaturated fatty acids (UFAs), while the carbon and nitrogen sources are established to be main activators (Verstrepen et al. 2003 Journal of Bioscience and Bioengineering 96:110-118). However, apart from ATF1 and ATF2, there is not much information available on which other genes influence acetate ester production, or how ATF1 and ATF2 are regulated. Pathways described to be involved are the Rox1, Ras/cAMP/PKA and the fermentable growth medium-induced (FGM) pathway (Verstrepen et al. 2003 FEMS yeast research 4:285-296). Both ATF1 and ATF2 have a broad spectrum specificity for the alcohol substrate, allowing all C2-C8 acetate esters to be formed during fermentation, although some alcohols are preferred over others (Verstrepen et al. 2003 Journal of Bioscience and Bioengineering 96: 110-118.). Although ATF1 is a known acetate ester production gene, to our knowledge, no natural variants of this gene have been described that influence acetate ester production. Moreover, in the synthetically acquired ATF1 mutants (such as those described in Verstrepen et al. 2003 Applied and environmental microbiology 69: 5228-5237.), there are still relatively high levels of certain acetate esters (e.g. ethyl acetate) produced. This illustrates that nature harbours several genetic mechanisms to effectively modulate acetate ester production. Therefore, it is advantageous to identify new, natural alleles that can more effectively reduce acetate ester production.

Similar to many of the industrially relevant traits, production of acetate esters varies widely between strains, and is a complex (quantitative or polygenic) trait. Indeed, there is an incredible broad diversity in acetate ester production amongst industrial yeast, ranging over 30-fold (Steensels et al. 2014 Applied Environ Microbiol 80:6965-6975), even between strains with identical ATF1 and ATF2 sequence. Genetic analysis of such traits remains an important challenge. Genome-wide analysis studies (GWAS) proved to be difficult in *S. cerevisiae* due to population stratifications (Tucker at al. 2014 Genetics 197: 1045-1049). Therefore, assessment of each trait individually is required. The most commonly applied technique to do this is Quantitative Trait Loci (QTL) analysis, a technique optimized for yeast in 2002 (Steinmetz et al. 2002 Nature 416: 326-330). To date, many industrially relevant traits have been assessed using (slight modification) of this technology, such as ethanol tolerance (Swinnen et al. 2012 Genome research 22: 975-984), thermotolerance (Yang et al. 2014 PLoS Genet 9: e1003693.), wine aromas (Steyer et al. 2012 BMC genomics 13: 1) and lag phase (Zimmer et al. 2014 PLoS One 9: e86298.).

Using high and low isoamyl acetate producing yeast strains and subsequent QTL analysis, we have found a novel natural gene, IMP1, that influences acetate ester production in yeast. Imp1 is a catalytic subunit of the mitochondrial 'Inner Membrane Peptidase' (IMP) complex, a complex that contains two catalytic subunits (Imp1 and Imp2) and Som1 (Jan et al. 2000, Mol Gen Genet 263: 483-491). Imp1p and Imp2p share 25% identity, though each protein has distinct substrate specificities. Most proteins undergo proteolytic processing upon import into mitochondria, and multiple proteases cleave different subsets of these proteins. The IMP processes some proteins that are translocated from the mitochondrial matrix into the intermembrane space. It is required for maturation of mitochondrial proteins of the intermembrane space. Among the substrates of Imp1 are the precursors to NADH-cytochrome b5 reductase (Mcr1), cytochrome b2 (Cyb2p), FAD-dependent glycerol-3-phosphate dehydrogenase (Gut2), and the mitochondrially encoded subunit II of cytochrome c oxidase (Cox2). To the best of our knowledge, Imp1 or other components of the IMP complex, have never been associated with variability in acetate ester production before. In our analysis we also found a novel natural mutant allele of Atf1.

SUMMARY

Given the undesirable effect of an excess amount of esters, especially of acetate esters such as ethyl acetate, on flavour of fermented beverages, there is strong need to develop strategies to reduce aroma production during fermentation. In this application a novel complex is disclosed that regulates acetate ester production levels. Moreover, alleles are disclosed of subunits of the Inner Membrane Peptidase complex with dominant negative effects on acetate ester production in yeast. More precisely, a mutant IMP1 allele is disclosed that encodes a C-terminal truncated Imp1 protein. This C-terminal truncated protein can even heterozygously limit acetate ester production. Therefore, in a first aspect, an isolated truncated yeast Imp1 protein is provided, wherein said protein lacks residues 147 to 190 of a wild-type full length yeast Imp1 protein. Also, an isolated C-terminal truncated yeast Imp1 protein is provided, wherein said protein comprises at least residues 10-148 of a wild-type full length yeast Imp1 protein. Accordingly, a nucleic acid sequence and a vector comprising that nucleic acid sequence, wherein said nucleic acid sequence encode the above described truncated Imp1 proteins are also part of this application. Also, a chimeric gene comprising a promoter which is active in a eukaryotic cell and a nucleic acid sequence encoding the truncated Imp1 proteins of the application and a 3' end region involved in transcription termination or polyadenylation is provided as well as a vector comprising said chimeric gene. In another aspect, a microorganism comprising the above mentioned truncated Imp1 proteins or the nucleic acid sequence, chimeric gene or vector of above is provided. Also, an engineered microorganism is disclosed, wherein said engineered microorganism comprises a mitochondrial Inner Membrane Peptidase (IMP) complex, wherein said engineered microorganism is engineered to disrupt, partially delete or completely delete at least one subunit of said IMP complex, and wherein said engineered microorganism produces at least 5% less of an acetate ester than a corresponding microorganism that has not been engineered to disrupt, partially delete or completely delete said at least one subunit of said IMP complex. In particular embodiment, said at least one subunit of said IMP complex is selected from the list consisting of Imp1, Imp2 and Som1 and/or said acetate ester is one or more acetate ester selected from the list consisting of isoamyl acetate, ethyl acetate, phenylethyl acetate, propyl acetate and isobutyl acetate. In particular embodiments of the application, the microorganism is a yeast, more particularly a *Saccharomyces* yeast, even more particularly *Saccharomyces cerevisiae*. Given that acetate ester production can be unwanted during fermentation processes, also a fermented solution (which can be beer, wine, sake, . . . ) comprising the above mentioned yeast strains is part of this application. In another aspect of the application, the use is provided of a nucleic acid sequence that disrupts, partially deletes or completely deletes at least one subunit of a mitochondrial IMP complex to limit the production of at least one acetate ester in a eukaryotic organism. In particular embodiments, said at least one subunit of said IMP complex is Imp1, Imp2 or Som1 and/or said acetate ester is one or more acetate ester selected from the list consisting of isoamyl acetate, ethyl acetate, phenylethyl acetate, propyl acetate and isobutyl acetate. Accordingly also the use of the truncated yeast Imp1 proteins (which are described above) to limit the production of at least one acetate ester in a eukaryotic organism is envisaged, wherein said acetate ester can be one or more acetate ester selected from the list consisting of isoamyl acetate, ethyl acetate, phenylethyl acetate, propyl acetate and isobutyl acetate. Given that acetate ester production is a complex process, it would be advantageous to combine several alleles that are involved in limiting acetate ester production. Therefore, the combined use of the above described mutant allele with alleles that further limit acetate ester production is provided. Alleles that further limit acetate ester production can be but are not limited to AFT1, AFT2, IMP1, IMP2 or SOM1. In the application also methods are provided to limit the production of at least one acetate ester in a eukaryotic cell, said method comprising the step of disrupting, partially deleting or completely deleting at least one subunit of a mitochondrial IMP complex in said eukaryotic cell. In particular embodiments, the method to limit the production of at least one acetate ester in a eukaryotic cell comprises the step of expressing the above described truncated Imp1 proteins or expressing the nucleic acid sequence, the chimeric gene or the vector from above. Also a method is disclosed to produce a low acetate ester producing yeast, comprising the step of crossing two parental yeast strains, wherein at least one parental yeast strain comprises at least one disrupted, partially deleted or complete deleted subunit of a mitochondrial IMP complex. This at least one subunit can be Imp1, Imp2 or Som1. In line with the previous, the method to produce a low acetate ester producing yeast can also use a parental strain that expresses the truncated Imp1 proteins of the applications or expresses the nucleic acid sequence, the chimeric gene or the vector from above. Finally a screening method is provided to obtain a low acetate ester producing yeast. The screening method comprises the steps of determining the expression and/or activity of at least one subunit of a mitochondrial IMP complex in a yeast strain and selecting a yeast strain wherein the expression and/or activity of said at least one subunit is disrupted, partially deleted or completely deleted.

The application discloses also a mutant yeast ATF1 allele comprising a mutated nucleic acid at position 221 of the open reading frame sequence of the wild-type ATF1 sequence depicted in SEQ ID No. 6. This mutation can be a frame shift mutation, a nonsense mutation or a missense mutation. In a particular embodiment, the mutation is a deletion as identified here and causes a frame shift leading to a premature stop codon. The application also provides a eukaryotic cell comprising that mutant ATF1 allele of this application and in particular embodiments, said eukaryotic cell is a yeast, even more particular a *Saccharomyces* yeast, even more particular *Saccharomyces cerevisiae*. Also a fermented beverage comprising above described yeasts are part of this application. The application also discloses the use of the mutant ATF1 allele of the application to limit the production of at least one acetate ester in a eukaryotic organism. In particular embodiment, said acetate ester is one or more acetate ester selected from the list consisting of isoamyl acetate, ethyl acetate, phenylethyl acetate, propyl acetate and isobutyl acetate. This is equivalent as saying that a method is provided to limit the production of at least one acetate ester in a eukaryotic cell, wherein said method comprises the step of expressing the mutant ATF1 yeast allele of the application.

DETAILED DESCRIPTION

Definitions

Figure 1:
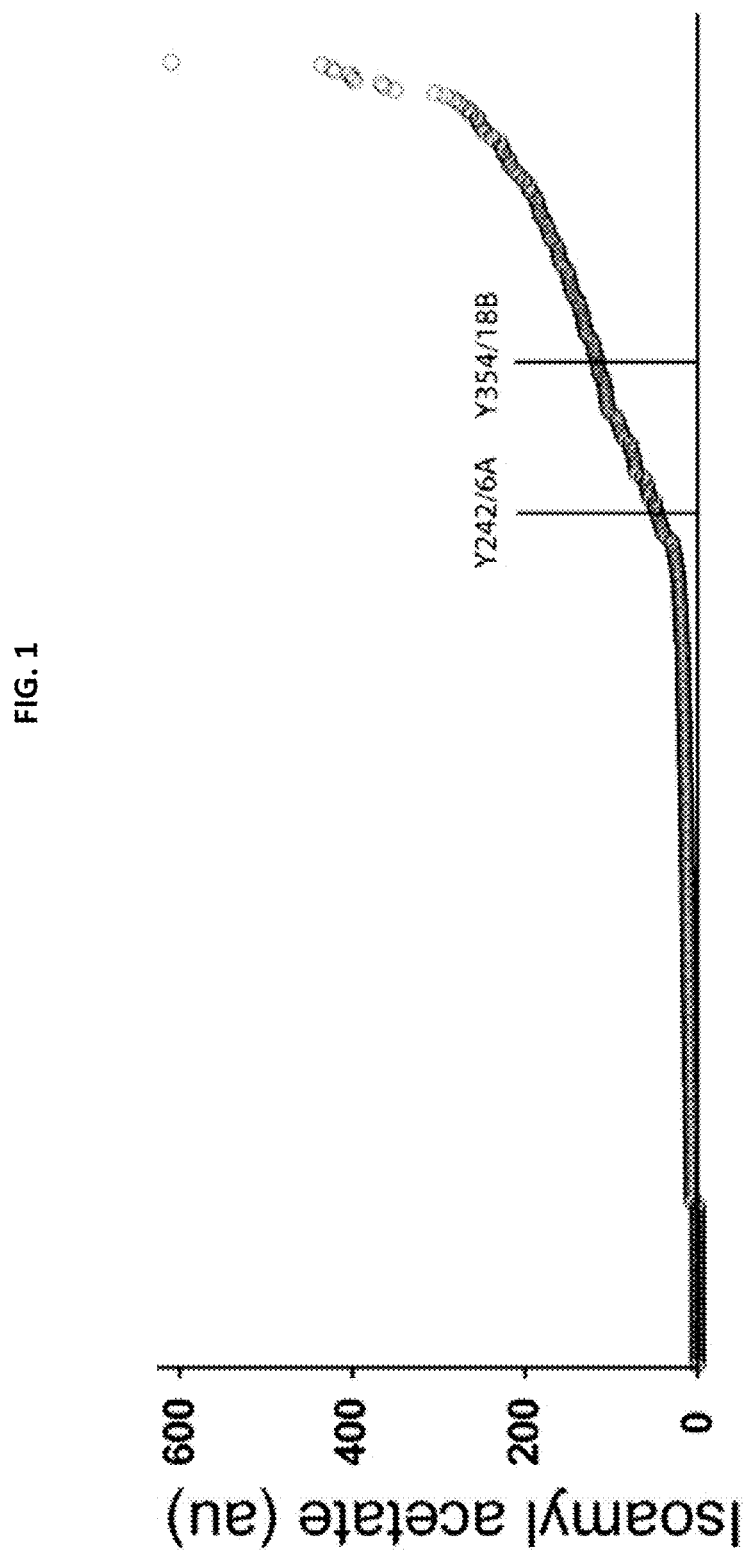
FIG. 1. Overview of the phenotypic variation of isoamyl acetate production among the analyzed segregants. Each dot on the graph represents one segregants, which are ordered from low (left-hand side) to high (right-hand side) isoamyl acetate production. All values are normalized to the value of the Hybrid A (='100'). The isoamyl acetate production of both segregants that were used as parental strain to obtain Hybrid A are indicated on the graph as a reference. au=arbitrary units.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Michael R. Green and Joseph Sambrook, Molecular Cloning: A Laboratory Manual, 4$^{th}$ ed., Cold Spring Harbor Laboratory Press, Plainsview, N.Y. (2012); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

We have identified the mitochondrial Inner Membrane Peptidase (IMP) complex as a regulator of acetate ester production in yeast. Disrupting, partially deleting or completely deleting one of the subunits of the IMP complex in yeast results in a reduced acetate ester production. In this application, we provide several mutant alleles and truncated proteins of the IMP complex subunits Imp1, Imp2 and Som1 that can be used in an industrially setting to limit the production of acetate esters during fermentation.

In a first aspect, an isolated truncated yeast Imp1 protein is provided, wherein said protein lacks residues 147-190 of a wild-type full length yeast Imp1 protein. The amino acid sequence of this wild-type full length yeast Imp1 protein is depicted in or defined by SEQ ID No. 4. "Lacking residues 147-190" is equivalent as saying that the truncated protein lacks residues 147 until 190 or that the truncated protein is devoid of the amino acid region from 147 until 190.

The term "truncated protein" refers to a protein which lacks one or more amino acids of the wild-type version of the protein, preferably the protein lacks one or more functional domains present in the wild-type protein. This is typically achieved by a mutation. A "truncated yeast Imp1 protein" as used here means that a part (N-terminal and/or C-terminal) of the wild-type yeast Imp1 protein (defined by SEQ ID No. 4) is missing. This does not mean that the rest of the truncated Imp1 protein should be identical in length or sequence to the wild-type yeast Imp1 protein. A truncated Imp1 protein lacking residues 147-190 thus also comprises Imp1 proteins with additional truncations besides the C-terminal truncation from residue 190 until residue 147. Alternatively, the truncated Imp1 protein lacking residues 147-190 can be fused to another polypeptide, whereby the C-terminal part of the wild-type Imp1 protein is replaced by said polypeptide and according a fusion protein is made.

For this application, a truncated protein lacks at least 1 amino acid, at least 2 amino acids, at least 3 amino acids, at least 4 amino acids, at least 5 amino acids, at least 6 amino acids, at least 7 amino acids, at least 8 amino acids, at least 9 amino acids, at least 10 amino acids, at least 15 amino acids, at least 20 amino acids, at least 30 amino acids, at least 40 amino acids, at least 50 amino acids of the full length wild-type protein. A truncated protein can be N-terminal truncated or C-terminal truncated.

In case of an N-terminal truncation, the truncated protein lacks the most N-terminal part of the wild-type version of the protein. This can be achieved by one or multiple mutations whereby the wild-type start codon is changed and thus not recognized anymore by the translational machinery of the cell. If protein synthesis is initiated at a later position in the reading frame of SEQ ID No. 3 (thus without a frame-shift has occurred), an N-terminal truncated protein is formed. N-terminal truncated as defined here thus not imply that the truncated protein should be shorter in length compared to the wild-type. The N-terminal truncated part of the wild-type protein can be replaced by any other amino acid sequence, for example but without having the purpose of limiting, a reporter gene or any other functional or non-functional polypeptide.

In case of a C-terminal truncation, the truncated protein lacks the most C-terminal part of the wild-type version of the protein. This can be achieved by a mutation specifically inducing premature termination of messenger RNA translation. As a non-limiting example, said C-terminal truncated protein may be created by a point mutation introducing a stop codon in the reading frame of SEQ ID No 3, or by a deletion or insertion resulting in a stop codon. In the latter case, the deletion or insertion may cause a frame shift, resulting in a mutant sequence at the C-terminal end of the truncated protein.

In one embodiment, an isolated truncated yeast Imp1 protein is provided, wherein said protein lacks residues 146-190 or 145-190 or 144-190 or 143-190 or 142-190 or 141-190 or 140-190 or 120-190 or 100-190 or 60-190 or 40-190 of a wild-type full length yeast Imp1 protein defined by SEQ ID No. 4.

In another embodiment, an isolated C-terminal truncated yeast Imp1 protein is provided, wherein said isolated C-terminal truncated yeast Imp1 protein comprises at least (or in particular embodiments consists of) residues 10-148 of a functional full length yeast Imp1 protein. This is equivalent as saying that an isolated C-terminal truncated yeast Imp1 protein is provided, wherein said protein comprises (or in particular embodiments consist of) an amino acid region starting at residue 10 of a functional full length yeast Imp1 protein and ending at residue 148 (thus residue 148 included) of said functional full length yeast Imp1 protein. In a particular embodiment this functional full length yeast Imp1 protein is a wild-type full length yeast Imp1 protein defined by SEQ ID No. 4.

In another embodiment, an isolated C-terminal truncated yeast Imp1 protein is provided, wherein said protein comprises at least 148, at least 149, at least 150, at least 151, at least 152, at least 153, at least 154, at least 155, at least 160, at least 165, at least 170, at least 175, at least 180 or at least 185 amino acid residues. In another embodiment, an isolated C-terminal truncated yeast Imp1 protein is provided, wherein said protein ends at residue 148, 149, 150, 151, 152, 153, 154, 155, 156, 157, 158, 159, 160, 165, 170, 175, 180 or 185 of the wild-type full length yeast Imp1 protein defined by SEQ ID No. 4.

In another embodiment, an isolated truncated yeast Imp1 protein is provided, wherein said protein is devoid of between 30 to 50 C-terminal amino acids of a full length yeast Imp1 protein depicted in SEQ ID No. 4 and wherein said truncated Imp1 protein is not the truncated yeast Imp1 protein depicted in SEQ ID No. 5. "Devoid of between 30 to 50 C-terminal amino acids" is equivalent as saying that the protein lacks at least the most C-terminal 30 amino acids and maximum the most C-terminal 50 amino acids of the full length yeast Imp1 protein depicted in SEQ ID No. 4. This means, in this embodiment, that truncated Imp1 proteins are provided that lack the 30, 31, 32, 33, 34, 35, 36, 37, 38, 39, 40, 41, 42, 43, 44, 45, 46, 47, 48, 49 or 50 most C-terminal amino acids of a full length yeast Imp1 protein depicted in SEQ ID No. 4 but wherein said truncated Imp1 protein is not the truncated yeast Imp1 protein depicted in SEQ ID No. 5.

In a particular embodiment, an isolated truncated yeast Imp1 protein is provided, wherein said protein is devoid of between 5 to 150, or between 10 to 150, or between 20 to 150, or between 30 to 150, or between 40 to 150 C-terminal amino acids of a full length yeast Imp1 protein depicted in SEQ ID No. 4 and wherein said truncated Imp1 protein is not the truncated yeast Imp1 protein depicted in SEQ ID No. 5. In another particular embodiment, an isolated truncated yeast Imp1 protein is provided, wherein said protein is devoid of between 5 to 130, or between 10 to 130, or between 20 to 130, or between 30 to 130, or between 40 to 130 C-terminal amino acids of a full length yeast Imp1 protein depicted in SEQ ID No. 4 and wherein said truncated Imp1 protein is not the truncated yeast Imp1 protein depicted in SEQ ID No. 5. In yet another embodiment, an isolated truncated yeast Imp1 protein is provided, wherein said protein is devoid of between 5 to 90, or between 10 to 90, or between 20 to 90, or between 30 to 90, or between 40 to 90 C-terminal amino acids of a full length yeast Imp1 protein depicted in SEQ ID No. 4 and wherein said truncated Imp1 protein is not the truncated yeast Imp1 protein depicted in SEQ ID No. 5. In even another particular embodiment, an isolated truncated yeast Imp1 protein is provided, wherein said protein is devoid of between 5 to 50, or between 10 to 50, or between 20 to 50, or between 30 to 50, or between 40 to 50 C-terminal amino acids of a full length yeast Imp1 protein depicted in SEQ ID No. 4 and wherein said truncated Imp1 protein is not the truncated yeast Imp1 protein depicted in SEQ ID No. 5.

In another embodiment, an isolated truncated yeast Imp1 protein is provided, wherein said protein comprises (or in particular embodiments consists of) amino acid residues 1-35, 1-50, 1-65, 1-100, 1-120 or 1-145 from a functional Imp1 protein, and wherein said truncated protein does not end at M147. In a particular embodiment, an isolated truncated yeast Imp1 protein is provided, wherein said protein comprises (or in other particular embodiments consist of) amino acid residues 1-35, 1-50, 1-65, 1-100, 1-120 or 1-145 from a functional Imp1 protein, and wherein said truncated protein is not fused to the C-terminal part of a IMP2 protein. "Comprising amino acid residues 1-35" is equivalent as saying that said protein comprises the amino acid sequence starting from amino acid 1 until amino acid 35 and amino acid 35 included.

In a particular embodiment, an isolated truncated yeast Imp1 protein is provided, wherein said protein comprises at least or consists of amino acid 1-153 of SEQ ID No. 2. Also, isolated truncated yeast Imp1 proteins are provided, wherein said protein comprises or consists of amino acids 1-154 or 1-155 of SEQ ID No. 2. In a more particular embodiment, an isolated truncated yeast Imp1 protein depicted in SEQ ID No. 2 is provided.

All the above described truncated Imp1 proteins lack a functional catalytic domain which is located in the C-terminal part of the full length wild-type Imp1 protein, more precisely from amino acid residue 148 until amino acid residue 190 of the full length Imp1 protein as depicted in SEQ ID No. 4, while the above described truncated yeast Imp1 proteins maintain a functional transmembrane domain and thus their integration in the mitochondrial membrane. As such, said truncated Imp1 proteins are still part of the IMP complex but negatively interfere with the function of the IMP complex. Indeed, the truncated Imp1 proteins have a dominant negative effect on the IMP complex. Therefore, this application also provides a dominant negative IMP1 mutant yeast protein comprising a transmembrane domain, wherein said mutant Imp1 protein is devoid of a functional C-terminal catalytic domain and wherein said mutant Imp1 protein is not the truncated yeast Imp1 protein depicted in SEQ ID No. 5. In a more particular embodiment, said mutant Imp1 protein is not fused to the C-terminal part of an IMP2 protein.

Surprisingly it was found that also N-terminal truncations of the Imp1 protein lead to reduced acetate ester production. More precisely, deletion of the N-terminal transmembrane domain (amino acids 14 to 31) was sufficient to reduce ethyl acetate and isoamyl acetate (see Example 7) production in yeast fermentations. Therefore, an isolated truncated yeast Imp1 protein is provided comprising a non-functional N-terminal transmembrane domain. More particularly, an isolated truncated yeast Imp1 protein lacking residues 14-31 of a wild-type full length yeast Imp1 protein defined by SEQ ID No. 4 is provided. In other particular embodiments, an isolated truncated yeast Imp1 protein is provided lacking residue 1-35, 1-50, 1-65, 1-100, 1-120 or 1-145 of a wild-type full length yeast Imp1 protein defined by SEQ ID No. 4. In a more particular embodiment, said truncated yeast Imp1 protein is an N-terminal truncated yeast Imp1 protein. "Non-functional" as used herein refers to a protein complex, a protein or certain domain within the protein (e.g. transmembrane domain) that performs suboptimal compared to a wild-type complex, protein or domain within a protein. In particular embodiments, non-functional means having at least a 50%, 60%, 70%, 80%, 90% or 100% reduction of the wild-type performance or function.

In another embodiment, an isolated truncated yeast Imp1 protein is provided, wherein said protein comprises at least amino acid 32-148 of SEQ ID No. 2. In a more particular embodiment, said protein lacks residues 14-31 of a wild-type full length yeast Imp1 protein defined by SEQ ID No. 4. In a more particular embodiment, an isolated truncated yeast Imp1 protein as depicted in SEQ ID No. 2, 6, 7 or 8 is provided.

In a second aspect, a nucleic acid sequence is provided, wherein said nucleic acid encodes a truncated yeast Imp1 protein, wherein said protein lacks residues 147-190 of a wild-type full length yeast Imp1 protein defined by SEQ ID No. 4.

In one embodiment, a nucleic acid sequence is provided, wherein said nucleic acid encodes a C-terminal truncated yeast Imp1 protein, wherein said protein comprises at least (or consists of) residues 10-148 of a functional full length yeast Imp1 protein defined by SEQ ID No. 4. In another embodiment, a nucleic acid sequence is provided, wherein said nucleic acid encodes a truncated yeast Imp1 protein, wherein said protein comprises at least (or consists of) amino acid 1-153, comprises (or consists of) amino acid 1-154 or comprises (or consists of) amino acid 1-155 of SEQ ID No. 2.

In another embodiment, a nucleic acid sequence is provided, wherein said nucleic acid encodes a truncated yeast Imp1 protein, wherein said nucleic acid sequence has a stop codon at position 457, 460, 463, 466, 469, 472, 475, 478, 481, 484, 487, 490, 493, 496, 499, 502, 505, 508, 511, 514, 517, 520, 523, 526, 529, 532, 535, 538, 541, 544, 547, 550, 553, 556, 559, 562, 565, 568 or 571.

In yet another embodiment, a nucleic acid sequence is provided, encoding a truncated yeast Imp1 protein, wherein said Imp1 protein lacks amino acids 14-31 of a wild-type full length yeast Imp1 protein defined by SEQ ID No. 4 or wherein said Imp1 protein comprises at least amino acid 32-148 of SEQ ID No. 2. More particularly, a nucleic acid sequence is provided encoding a truncated yeast Imp1 protein comprising at least amino acid 32-148 of SEQ ID No. 2 and further lacking amino acids 14-31 of a wild-type full length yeast Imp1 protein defined by SEQ ID No. 4. In another embodiment, a nucleic acid sequence is provided, wherein said nucleic acid encodes a truncated yeast Imp1 protein, and wherein said nucleic acid sequence is depicted in SEQ ID No. 1 or wherein said truncated yeast Imp1 protein is depicted in SEQ ID No. 2, 6, 7 or 8.

In a particular embodiment, a nucleic acid sequence is provided, wherein said nucleic acid encodes one of the truncated yeast Imp1 proteins above described in the first aspect or in the accompanying embodiments of the first aspect.

In another embodiment, a vector is provided, wherein said vector comprises a nucleic acid sequence described in the second aspect or in one of its embodiments.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g. peptide nucleic acids).

By "encoding" or "encodes" or "encoded", with respect to a specified nucleic acid, is meant comprising the information for transcription into an RNA molecule and in some embodiments, translation into the specified protein or amino acid sequence. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

The term "vector" refers to any linear or circular DNA construct containing the above described chimeric gene of the invention. The vector can refer to an expression cassette or any recombinant expression system for the purpose of expressing a nucleic acid sequence of the invention in vitro or in vivo, constitutively or inducibly, in any cell, including, in addition to plant cells, prokaryotic, yeast, fungal, insect or mammalian cells. The vector can remain episomal or integrate into the host cell genome. The vector can have the ability to self-replicate or not (i.e., drive only transient expression in a cell). The term includes recombinant expression cassettes that contain only the minimum elements needed for transcription of the recombinant nucleic acid. The vector of the invention is a "recombinant vector" which is by definition a man-made vector.

In a third aspect, a chimeric gene is provided, said chimeric gene comprises a promoter which is active in a eukaryotic cell; a nucleic acid sequence encoding a truncated yeast Imp1 protein, wherein said protein lacks residues 147-190 or residues 14-31 of a wild-type full length yeast Imp1 protein defined by SEQ ID No. 4; and a 3' end region involved in transcription termination or polyadenylation. In one embodiment, a chimeric gene is provided, said chimeric gene comprises a promoter which is active in a eukaryotic cell; a nucleic acid sequence encoding a C-terminal truncated yeast Imp1 protein, wherein said protein comprises at least (or consists of) residues 10-148 of a wild-type full length yeast Imp1 protein defined by SEQ ID No. 4; and a 3' end region involved in transcription termination or polyadenylation. In another embodiment, a chimeric gene is provided, said chimeric gene comprises a promoter which is active in a eukaryotic cell; a nucleic acid sequence encoding a truncated yeast Imp1 protein, wherein said protein comprises at least (or consists of) amino acid 1-153 of SEQ ID No. 2; and a 3' end region involved in transcription termination or polyadenylation. In another embodiment, a chimeric gene is provided, said chimeric gene comprises a promoter which is active in a eukaryotic cell; a nucleic acid sequence encoding a truncated yeast Imp1 protein, wherein said nucleic acid sequence is depicted in SEQ ID No. 1 or wherein said nucleic acid sequence encodes the protein depicted in SEQ ID No. 2, 6, 7 or 8; and a 3' end region involved in transcription termination or polyadenylation.

In particular embodiments, a chimeric gene is provided, said chimeric gene comprises a promoter which is active in a eukaryotic cell; one of the nucleic acid sequences described in the second aspect or in the embodiments of the second aspect of this application; and a 3' end region involved in transcription termination or polyadenylation.

In another embodiment, a vector is provided, wherein said vector comprises a chimeric gene described in the one of the embodiments of the third aspect.

In a particular embodiment the promoter in the chimeric gene of the invention is active in yeast. In a preferred embodiment, said promoter is selected from the list comprising pTEF1 (Translation Elongation Factor 1); pTEF2; pHXT1 (Hexose Transporter 1); pHXT2; pHXT3; pHXT4; pTDH3 (Triose-phosphate Dehydrogenase) also known in the art as pGADPH (Glyceraldehyde-3-phosphate dehydrogenase) or pGDP or pGLD1 or pHSP35 or pHSP36 or pSSS2; pTDH2 also known in the art as pGLD2; pTDH1 also known in the art as pGLD3; pADH1 (Alcohol Dehydrogenase) also know in the art as pADC1; pADH2 also known in the art as pADR2; pADH3; pADH4 also known in the art as pZRG5 or pNRC465; pADH5; pADH6 also known in the art as pADHVI; pPGK1 (3-Phosphoglycerate Kinase); pGAL1 (Galactose metabolism); pGAL2; pGAL3; pGAL4; pGAL5 also known in the art as pPGM2 (Phosphoglucomutase); pGAL6 also known in the art as pLAP3 (Leucine Aminopeptidase) or pBLH1 or pYCP1; pGAL7; pGAL10; pGAL11 also known in the art as pMED15 or pRAR3 or pSDS4 or SPT13 or ABE1; pGAL80; pGAL81; pGAL83 also know in the art as pSPM1; pSIP2 (SNF1-interacting Protein) also know in the art as pSPM2; pMET (Methionine requiring); pPMA1 (Plasma Membrane ATPase) also known in the art as pKTI10; pPMA2; pPYK1 (Pyruvate Kinase) also known in the art as pCDC19; pPYK2; pENO1 (Enolase) also known in the art as pHSP48; pENO2; pPHO (Phosphate metabolism); pCUP1 (Cuprum); pCUP2 also known in the art as pACE1; pPET56 also known in the art as pMRM1 (Mitochondrial rRNA Methyltransferase); pNMT1 (N-Myristoyl Transferase) also known in the art as pCDC72; pGRE1 (Genes de Respuesta a Estres); pGRE2; GRE3; pSIP18 (Salt Induced Protein); pSV40 (Simian Vacuolating virus) and pCaMV (Cauliflower Mosaic Virus). These promoters are widely used in the art. The skilled person will have no difficulty identifying them in databases. For example, the skilled person will consult the *Saccharomyces* genome database website (world wide web at yeastgenome.org) or the Promoter Database of *Saccharomyces cerevisiae* (world wide web at rulai.cshl.edu/SCPD/) for retrieving the yeast promoters' sequences. Yeast, as used here, can be any yeast useful for industrial applications. Preferable, said yeast is useful for ethanol production, including, but not limited to *Saccharomyces, Zygosaccharomyces, Brettanomyces* and *Kluyveromyces*. Preferably, said yeast is a *Saccharomyces* sp., even more preferably it is a *Saccharomyces cerevisiae* sp.

In the present application a "promoter" comprises regulatory elements, which mediate the expression of a nucleic acid molecule. For expression, the nucleic acid molecule must be linked operably to or comprise a suitable promoter which expresses the gene at the right point in time and with the required spatial expression pattern. The term "operably linked" as used herein refers to a functional linkage between the promoter sequence and the gene of interest, such that the promoter sequence is able to initiate transcription of the gene of interest. A promoter that enables the initiation of gene transcription in a eukaryotic cell is referred to as being "active". To identify a promoter which is active in a eukaryotic cell, the promoter can be operably linked to a reporter gene after which the expression level and pattern of the reporter gene can be assayed. Suitable well-known reporter genes include for example beta-glucuronidase, beta-galactosidase or any fluorescent or luminescent protein. The promoter activity is assayed by measuring the enzymatic activity of the beta-glucuronidase or beta-galactosidase. Alternatively, promoter strength may also be assayed by quantifying mRNA levels or by comparing mRNA levels of the nucleic acid, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994).

A "chimeric gene" or "chimeric construct" is a recombinant nucleic acid sequence in which a promoter or regulatory nucleic acid sequence is operably linked to, or associated with, a nucleic acid sequence that codes for a mRNA and encodes an amino acid sequence, such that the regulatory nucleic acid sequence is able to regulate transcription or expression of the associated nucleic acid coding sequence. The regulatory nucleic acid sequence of the chimeric gene is not operably linked to the associated nucleic acid sequence as found in nature.

The term "a 3' end region involved in transcription termination or polyadenylation" encompasses a control sequence which is a DNA sequence at the end of a transcriptional unit which signals 3' processing or polyadenylation of a primary transcript and is involved in termination of transcription. The control sequence for transcription termination or terminator can be derived from a natural gene or from a variety of genes. For expression in yeast the terminator to be added may be derived from, for example, the TEF or CYC1 genes or alternatively from another yeast gene or less preferably from any other eukaryotic or viral gene.

Also envisaged in this application and thus in a fourth aspect, is an inhibitor of the functional expression or activity of at least one subunit of the mitochondrial IMP complex. In a particular embodiment, said at least one subunit of the mitochondrial IMP complex is Imp1, Imp2 or Som1. In another particular embodiment, said inhibitor is selected from the list consisting of an antisense oligomer, a miRNA, a siRNA, a shRNA, a gapmer, a morpholino, a locked nucleic acid, a peptide nucleic acid, ribozyme, ZFN, a TALEN, a CRISPR-Cas, a CRISPR-C2c2 and a meganuclease. This application also provides the use of said inhibitor to reduce or to limit the production of at least one acetate ester in a eukaryotic cell. In a particular embodiment said at least one acetate ester is one or more acetate ester selected from the list consisting of isoamyl acetate, ethyl acetate, phenylethyl acetate, propyl acetate and isobutyl acetate. Nowadays, the most attractive genetic inhibitors of functional gene expression and/or gene activity are nucleases, such as zinc-finger nucleases (ZFNs), Transcription Activator-Like Effector Nucleases (TALENs), meganucleases but especially the CRISPR-Cas system. "Nucleases" as used herein are enzymes that cut nucleotide sequences. These nucleotide sequences can be DNA or RNA. If the nuclease cleaves DNA, the nuclease is also called a DNase. If the nuclease cuts RNA, the nuclease is also called an RNase. Upon cleavage of a DNA sequence by nuclease activity, the DNA repair system of the cell will be activated. Yet, in most cases the targeted DNA sequence will not be repaired as it originally was and small deletions, insertions or replacements of nucleic acids will occur, mostly resulting in a mutant DNA sequence.

ZFN are artificial restriction enzymes generated by fusing a zinc finger DNA-binding domain to a DNA-cleavage domain. Zinc finger domains can be engineered to target desired DNA sequences, which enables zinc-finger nucleases to target a unique sequence within a complex genome. By taking advantage of endogenous DNA repair machinery, these reagents can be used to precisely alter the genomes of simple and higher organisms. Other technologies for genome customization that can be used to knock out genes are meganucleases and TAL effector nucleases (TALENs, Cellectis bioresearch). A TALEN® is composed of a TALE DNA binding domain for sequence-specific recognition fused to the catalytic domain of an endonuclease that introduces double strand breaks (DSB). The DNA binding domain of a TALEN® is capable of targeting with high precision a large recognition site (for instance 17 bp). Meganucleases are sequence-specific endonucleases, naturally occurring "DNA scissors", originating from a variety of single-celled organisms such as bacteria, yeast, algae and some plant organelles. Mega nucleases have long recognition sites of between 12 and 30 base pairs. The recognition site of natural meganucleases can be modified in order to target native genomic DNA sequences (such as endogenous genes). Another recent and very popular genome editing technology is the CRISPR-Cas system, which can be used to achieve RNA-guided genome engineering. CRISPR interference is a genetic technique which allows for sequence-specific control of gene expression in prokaryotic and eukaryotic cells. It is based on the bacterial immune system-derived CRISPR (clustered regularly interspaced palindromic repeats) pathway and has been modified to edit basically any genome. By delivering the Cas nuclease (in many cases Cas9) complexed with a synthetic guide RNA (gRNA) in a cell, the cell's genome can be cut at a desired location depending on the sequence of the gRNA, allowing existing genes to be removed and/or new one added and/or more subtly removing, replacing or inserting single nucleotides (e.g. DiCarlo et al 2013 Nucl Acids Res doi:10.1093/nar/gkt135; Sander & Joung 2014 Nat Biotech 32:347-355).

Expression of subunits of the IMP complex can also be inhibited at the level of RNA. This can for example be done by nucleases that target the RNA molecules or by the inhibitory RNA technology wherein inhibitors will break down transcribed mRNA or mRNA precursors. The inhibitory RNA technology or RNA interference (RNAi) is a form of post-transcriptional gene silencing that can be used as one of the methods to inhibit or reduce the functional expression of IMP1, IMP2 or SOM1. The phenomenon of RNA interference was first observed and described in *Caenorhabditis elegans* where exogenous double-stranded RNA (dsRNA) was shown to specifically and potently disrupt the activity of genes containing homologous sequences through a mechanism that induces rapid degradation of the target RNA. Numerous reports have describe the same catalytic phenomenon in other organisms, including experiments demonstrating spatial and/or temporal control of gene inactivation, including plants, protozoa, invertebrates, vertebrates and mammals. RNAi mediated degradation of the target mRNA can be detected by measuring levels of the target mRNA or protein in yeast, using standard techniques for isolating and quantifying mRNA or protein which are known by the skilled one. The mediators of sequence-specific messenger RNA degradation are small interfering RNAs (siRNAs) generated by ribonuclease III cleavage from longer dsRNAs. Generally, the length of siRNAs is between 20-25 nucleotides (Elbashir et al. (2001) Nature 411, 494 498). The siRNA typically comprise a sense RNA strand and a complementary antisense RNA strand annealed together by standard Watson Crick base pairing interactions (hereinafter "base paired"). The sense strand comprises a nucleic acid sequence that is identical to a target sequence (e.g. the IMP1, IMP2 and/or SOM1 sequence) contained within the target mRNA. The sense and antisense strands of the present siRNA can comprise two complementary, single stranded RNA molecules or can comprise a single molecule in which two complementary portions are base paired and are covalently linked by a single stranded "hairpin" area (often referred to as shRNA). The siRNAs that can be used to inhibit or reduce the functional expression of an IMP complex subunit can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion. The siRNAs can be targeted to any stretch of approximately 19 to 25 contiguous nucleotides in sequence of an IMP complex subunit (the "target sequence"). Techniques for selecting target sequences for siRNA are well known in the art. Thus, the sense strand of the present siRNA comprises a nucleotide sequence identical to any contiguous stretch of about 19 to about 25 nucleotides in the target mRNA. siRNAs can be obtained using a number of techniques known to those of skill in the art. For example, the siRNAs can be chemically synthesized or recombinantly produced using methods known in the art. Preferably, the siRNA of the application are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Alternatively, siRNA can also be expressed from recombinant circular or linear DNA plasmids using any suitable promoter. Selection of other suitable promoters is within the skill in the art. The recombinant plasmids of the invention can also comprise inducible or regulatable promoters for expression of the siRNA in a eukaryotic cell.

Next to the use of dsRNA or the derived siRNAs, also antisense oligomers can be used as inhibitors of the expression of an IMP complex subunit. An "antisense oligomer" refers to an antisense molecule or anti-gene agent that comprises an oligomer of at least about 10 nucleotides in length. In particular embodiments an antisense oligomer comprises at least 15, 18, 20, 25, 30, 35, 40, or 50 nucleotides. Antisense approaches involve the design of oligonucleotides (either DNA or RNA, or derivatives thereof) that are complementary to the RNA sequence of an IMP complex subunit. Antisense oligomers used to inhibit expression of an IMP complex subunit may consist of DNA, RNA or other, synthetic structures such as phosphorothiates, 2'-O-alkyl ribonucleotide chimeras, locked nucleic acid (LNA) (which will be discussed further), peptide nucleic acid (PNA), or morpholinos. With the exception of RNA oligomers, PNAs and morpholinos, antisense oligomers typically act in eukaryotic cells through the mechanism of RNase H-mediated target cleavage. PNAs and morpholinos bind complementary DNA and RNA targets with high affinity and specificity, and thus act through a simple steric blockade of the RNA translational machinery, and appear to be completely resistant to nuclease attack. Recently it has been shown that morpholino antisense oligonucleotides in zebrafish and frogs overcome the limitations of RNase H-competent antisense oligonucleotides, which include numerous non-specific effects due to the non-target-specific cleavage of other mRNA molecules caused by the low stringency requirements of RNase H. Morpholino oligomers therefore represent an important new class of antisense molecule. Oligomers of the invention may be synthesized by standard methods known in the art. As examples, phosphorothioate oligomers may be synthesized by the method of Stein et al. (1988) Nucleic Acids Res. 16, 3209 3021), methylphosphonate oligomers can be prepared by use of controlled pore glass polymer supports (Sarin et al. (1988) Proc. Natl. Acad. Sci. USA. 85, 7448-7451). Morpholino oligomers may be synthesized by the method of Summerton and Weller U.S. Pat. Nos. 5,217,866 and 5,185,444. Antisense RNA may be introduced into a cell to inhibit translation of a complementary mRNA by base pairing to it and physically obstructing the translation machinery. This effect is therefore stoichiometric. Absolute complementarity, although preferred, is not required. A sequence "complementary" to a portion of an RNA, as referred to herein, means a sequence having sufficient complementarity to be able to hybridize with the RNA, forming a stable duplex; in the case of double stranded antisense polynucleotide sequences, a single strand of the duplex DNA may thus be tested, or triplex formation may be assayed. The ability to hybridize will depend on both the degree of complementarity and the length of the antisense polynucleotide sequence. Generally, the longer the hybridizing polynucleotide sequence, the more base mismatches with an RNA it may contain and still form a stable duplex (or triplex, as the case may be). One skilled in the art can ascertain a tolerable degree of mismatch by use of standard procedures to determine the melting point of the hybridized complex.

An antisense construct can be delivered, for example, as an expression plasmid, which, when transcribed in the cell, produces RNA that is complementary to at least a unique portion of a subunit of the IMP complex.

Another particularly form of antisense RNA strategy are gapmers. A gapmer is a chimeric antisense oligonucleotide that contains a central block of deoxynucleotide monomers sufficiently long to induce RNase H cleavage. The central block of a gapmer is flanked by blocks of 2'-O modified ribonucleotides or other artificially modified ribonucleotide monomers such as bridged nucleic acids (BNAs) that protect the internal block from nuclease degradation. Gapmers have been used to obtain RNase-H mediated cleavage of target RNAs, while reducing the number of phosphorothioate linkages. Phosphorothioates possess increased resistance to nucleases compared to unmodified DNA. However, they have several disadvantages. These include low binding capacity to complementary nucleic acids and non-specific binding to proteins that cause toxic side-effects limiting their applications. The occurrence of toxic side-effects together with non-specific binding causing off-target effects has stimulated the design of new artificial nucleic acids for the development of modified oligonucleotides that provide efficient and specific antisense activity in vivo without exhibiting toxic side-effects. By recruiting RNase H, gapmers selectively cleave the targeted oligonucleotide strand. The cleavage of this strand initiates an antisense effect. This approach has proven to be a powerful method in the inhibition of gene functions.

Finally, miRNA activity may also be inhibited using ribozymes instead of antisense RNA. Ribozymes are catalytic RNA molecules with enzyme-like cleavage properties that can be designed to target specific RNA sequences. Successful target gene inactivation, including temporally and tissue-specific gene inactivation, using ribozymes has been reported in mouse, zebrafish and fruitflies. The feasibility of this approach for miRNA modulation has recently been demonstrated (Suryawanshi H et al., Mol Biosyst. 6(10): 1807-9 (2010)). Recently, it was demonstrated that the Crispr-Cas editing system can also be used to target RNA. It has been shown that the Class 2 type VI-A CRISPR-Cas effector C2c2 can be programmed to cleave single stranded RNA targets carrying complementary protospacers (Abudayyet et al 2016 Science 10.1126/science.aaf5573). C2c2 is a single-effector endoRNase mediating ssRNA cleavage once it has been guided by a single crRNA guide toward the target RNA. This system can thus also be used to target and thus to break down one or more subunits of the IMP complex.

In a fifth aspect, a microorganism is provided comprising a truncated yeast Imp1 protein, wherein said truncated Imp1 protein lacks residues 147-190 of a wild-type full length yeast Imp1 protein defined by SEQ ID No. 4 or comprising a nucleic acid sequence encoding said truncated Imp1 protein or comprising a vector, wherein said vector comprises said nucleic acid sequence. In one embodiment, a microorganism is provided comprising a C-terminal truncated yeast Imp1 protein, wherein said protein comprises at least (or consists of) residues 10-148 of a functional full length yeast Imp1 protein defined by SEQ ID No. 4 or comprising a nucleic acid sequence encoding said C-terminal truncated yeast Imp1 protein or comprising a vector, wherein said vector comprises said nucleic acid sequence. In another embodiment, a microorganism is provided comprising a truncated yeast Imp1 protein, wherein said protein comprises at least (or consists of) amino acid 1-153 of SEQ ID No. 2 or comprising a nucleic acid sequence encoding said truncated Imp1 protein or comprising a vector, wherein said vector comprises said nucleic acid sequence. In yet another embodiment, a microorganism is provided comprising a truncated yeast Imp1 protein, wherein said Imp1 protein lacks amino acids 14-31 of a wild-type full length yeast Imp1 protein defined by SEQ ID No. 4 or wherein said Imp1 protein comprises at least amino acid 32-148 of SEQ ID No. 2. More particularly, a microorganism is provided comprising a truncated yeast Imp1 protein comprising at least amino acid 32-148 of SEQ ID No. 2 and further lacking amino acids 14-31 of a wild-type full length yeast Imp1 protein defined by SEQ ID No. 4. In another embodiment, a microorganism is provided comprising a nucleic acid as depicted in SEQ ID No. 1 or comprising a truncated yeast Imp1 protein as depicted in SEQ ID No. 2, 6, 7 or 8.

In another embodiment, a microorganism is provided, wherein said microorganism comprises a chimeric gene comprising a promoter which is active in a eukaryotic cell; a nucleic acid sequence encoding a truncated yeast Imp1 protein which lack residues 147-190 of a wild-type full length yeast Imp1 protein defined by SEQ ID No. 4 or a nucleic acid sequence encoding a truncated yeast Imp1 protein which lacks amino acids 14-31 of a wild-type full length yeast Imp1 protein defined by SEQ ID No. 4 or a nucleic acid sequence encoding a truncated yeast Imp1 protein comprising at least amino acid 32-148 of SEQ ID No. 2 or a nucleic acid sequence encoding a truncated yeast Imp1 protein comprising at least amino acid 32-148 of SEQ ID No. 2 and further lacking amino acids 14-31 of a wild-type full length yeast Imp1 protein defined by SEQ ID No. 4. or a nucleic acid sequence encoding a truncated yeast Imp1 protein comprising at least (or consists of) residues 10-148 of a functional full length yeast Imp1 protein defined by SEQ ID No. 4 or a nucleic acid sequence encoding a truncated Imp1 protein comprising at least (or consists of) amino acid 1-153 of SEQ ID No. 2 or comprising the nucleic acid sequence depicted in SEQ ID No. 1 or encoding a truncated yeast Imp1 protein as depicted in SEQ ID No. 2, 6, 7 or 8; and a 3' end region involved in transcription termination or polyadenylation.

In other particular embodiments, a microorganism is provided, wherein said microorganism comprises one of the truncated Imp1 proteins described in the first aspect or in the embodiments of the first aspect of this application. In other particular embodiments, a microorganism is provided, wherein said microorganism comprises a nucleic acid sequence encoding a truncated yeast Imp1 protein, wherein said nucleic acid sequence is one of the nucleic acid sequences described in the second aspect or in the embodiments of the second aspect of this application. In yet another particular embodiment, a microorganism is provided, wherein said microorganism comprises a chimeric gene, wherein said chimeric gene is one of the chimeric genes described in the third aspect or in the embodiments of the third aspect of this application.

In a particular extension of the fifth aspect and of all embodiments of the fifth aspect, said microorganism is a yeast, more particularly a yeast useful for ethanol production, including, but not limited to *Saccharomyces*, *Zygosaccharomyces*, *Brettanomyces* and *Kluyveromyces*. Even more particularly, said yeast is a *Saccharomyces* sp., most particularly it is a *Saccharomyces cerevisiae* sp. Said yeast strains are particularly useful for industrial fermentation at conditions wherein too much acetate esters, more particularly too much ethyl acetate is produced.

In a sixth aspect, an engineered eukaryotic cell comprising a mitochondrial inner membrane peptidase (IMP) complex is provided, wherein said engineered eukaryotic cell is engineered to disrupt, partially delete or completely delete at least one subunit of said IMP complex, and wherein said engineered microorganism produces at least 5%, at least 10%, at least 20%, at least 30%, at least 40%, at least 50%, at least 60%, at least 70%, at least 80%, at least 90%, at least 95% or 100% less of an acetate ester or produces between 10% and 50%, or between 20% and 60%, or between 30% and 70% or between 40% and 80% less of an acetate ester than a corresponding eukaryotic cell that has not been engineered to disrupt, partially delete or completely delete said at least one subunit of said IMP complex. This is equivalent as saying that an engineered eukaryotic cell comprising a mitochondrial inner membrane peptidase (IMP) complex is provided, wherein said engineered eukaryotic cell is engineered to disrupt, partially delete or completely delete at least one subunit of said IMP complex, and wherein the level of a produced acetate ester in said engineered eukaryotic cell is reduced with at least 5%, at least 10%, at least 20%, at least 30%, at least 40%, at least 50%, at least 60%, at least 70%, at least 80%, at least 90%, at least 95% or 100% compared to a corresponding eukaryotic cell that has not been engineered to disrupt, partially delete or completely delete said at least one subunit of said IMP complex or is reduced between 10% and 50%, or between 20% and 60%, or between 30% and 70% or between 40% and 80% compared to a corresponding eukaryotic cell that has not been engineered to disrupt, partially delete or completely delete said at least one subunit of said IMP complex. In case of a 100% reduction in production of one acetate ester, said acetate ester is present at a non-detectable level or is absent. In a more particular embodiment, said at least one subunit of said IMP complex is selected from the list consisting of Imp1, Imp2 and Som1. In another particular embodiment, said acetate ester is one or more acetate ester selected from the list consisting of isoamyl acetate, ethyl acetate, phenylethyl acetate, propyl acetate and isobutyl acetate. This application thus also provides an engineered eukaryotic cell comprising a mitochondrial inner membrane peptidase (IMP) complex, wherein said engineered eukaryotic cell is engineered to disrupt, partially delete or completely delete Imp1, Imp2 and/or Som1 function, and wherein said engineered eukaryotic cell produces at least 5%, at least 10%, at least 20%, at least 30%, at least 40%, at least 50%, at least 60%, at least 70%, at least 80%, at least 90, at least 95% or 100% less or reduced between 10% and 50%, or between 20% and 60%, or between 30% and 70% or between 40% and 80% less isoamyl acetate, ethyl acetate, phenylethyl acetate, propyl acetate and/or isobutyl acetate than a corresponding eukaryotic cell that has not been engineered to disrupt, partially delete or completely delete Imp1, Imp2 and/or Som1 function. In particular embodiments, said eukaryotic cell is a yeast, more particularly a yeast useful for ethanol production, including, but not limited to *Saccharomyces*, *Zygosaccharomyces*, *Brettanomyces* and *Kluyveromyces*. Even more particularly, said yeast is a *Saccharomyces* sp., most particularly it is a *Saccharomyces cerevisiae* sp.

As previously explained, production of particular acetate esters can have negative effects on consumers' appreciation of a certain fermented product. Indeed, for example, fermented beverages (e.g. beer) with high concentrations of ethyl acetate are often negatively perceived as having a "chemical" or "nail polish remover" flavour. Therefore, the yeast strains which are subject of and are disclosed in the current application are extremely useful in the fermentation industry. Fermented products can have applications in food (for example but not limited to chocolate) and beverages (for example but not limited to beer, wine, sake) as well as in general industry (for example but not limited to bioethanol production) where the production of a flavour neutral product is desired or more particularly where a product is desired with low acetate ester levels. Thus, also envisaged in this application is a fermented solution comprising the yeast strains of this application, or more particularly comprising a yeast strain that comprises a truncated yeast Imp1 protein, wherein said protein lacks residues 147-190 of a wild-type full length yeast Imp1 protein defined by SEQ ID No. 4 or that lacks amino acids 14-31 of a wild-type full length yeast Imp1 protein defined by SEQ ID No. 4 or that comprises at least amino acid 32-148 of SEQ ID No. 2 or that comprises at least amino acid 32-148 of SEQ ID No. 2 and further lacks amino acids 14-31 of a wild-type full length yeast Imp1 protein defined by SEQ ID No. 4. or that comprises a C-terminal truncated yeast Imp1 protein, wherein said protein comprises at least (or consists of) residues 10-148 of a wild-type full length yeast Imp1 protein defined by SEQ ID No. 4 or that comprises a truncated yeast Imp1 protein, wherein said protein comprises at least (or consists of) amino acid 1-153 of SEQ ID No. 2 and that comprises the nucleic acid sequence depicted in SEQ ID No. 1 or encoding a truncated yeast Imp1 protein as depicted in SEQ ID No. 2, 6, 7 or 8. In even more particular embodiments, said fermented solution is a fermented beverage or is a fermented solution not suited for consumption. Non-limiting examples of a fermented beverage are beer, wine, sake, . . . . A non-limiting example of a fermented solution not suited for consumption is bio-ethanol. In an even more particular embodiment, said fermented beverage is beer.

As clearly illustrated in this application, interference with the function of the IMP complex reduces the production of acetate esters in yeast. Prove for this has been provided using several dominant negative IMP1 mutants and loss-of-function mutants for IMP2 or SOM1. Therefore, and in a seventh aspect of this application, the use is provided of a disrupted, partially deleted or complete deleted nucleic acid sequence encoding a subunit of a mitochondrial IMP complex or the use of a nucleic acid sequence that disrupts, partially deletes or completely deletes at least one subunit of a mitochondrial IMP complex to limit the production of at least one acetate ester in a eukaryotic organism or particularly to limit the production of at least one acetate ester during yeast fermentation. In particular embodiments, the use is provided of a disrupted or partially deleted nucleic acid sequence encoding a subunit of a mitochondrial IMP complex or of a nucleic acid sequence that disrupts, partially deletes or completely deletes at least one subunit of a mitochondrial IMP complex to produce a fermented solution with a reduced level of at least one acetate ester or to produce a flavour neutral alcohol or to produce a low acetate ester producing yeast. In one embodiment, said at least one subunit of a mitochondrial IMP complex is Imp1, Imp2 or Som1. In another embodiment, said acetate ester is one or more acetate ester selected from the list consisting of isoamyl acetate, ethyl acetate, phenylethyl acetate, propyl acetate and isobutyl acetate.

In another embodiment, the use is provided of a disrupted or partially deleted nucleic acid sequence encoding a subunit of a mitochondrial IMP complex or of a nucleic acid sequence that disrupts, partially deletes or completely deletes the expression or the functional expression of at least one gene that encodes a subunit of a mitochondrial IMP complex or of a nucleic acid sequence that disrupts, partially deletes or completely deletes the function of at least one subunit of a mitochondrial IMP complex to limit the production of at least one acetate ester in a eukaryotic organism or to limit the production of at least one acetate ester during yeast fermentation. In a particular embodiment, said subunit of a mitochondrial IMP complex is Imp1, Imp2 or Som1.

With "functional expression" of at least one gene that encodes a subunit of the IMP complex, it is meant the transcription of a functional gene product. "Disrupting, partially deleting or completely deleting the functional expression" is equivalent as saying partially or completely inhibiting the formation of a functional mRNA molecule encoding a subunit of the IMP complex. Means and methods to disrupt, partially deleted or completely delete a gene or protein are well known in the art. The skilled person can select from a plethora of techniques to affect the expression or function of a subunit of the IMP complex (also described above in the fourth aspect). At the DNA level this can for example be achieved by removing or disrupting a gene encoding an IMP complex subunit or by mutations in the promoter of a gene encoding an IMP complex subunit. Non-limiting examples are knock-outs or loss-of-function mutations but also gain-of-function mutations and dominant negative mutations can disrupt the functional expression or inhibit the formation of a functional mRNA molecule. A "knock-out" can be a gene knockdown (leading to reduced gene expression) or the gene can be knocked out by a mutation such as, a point mutation, an insertion, a deletion, a frameshift, or a missense mutation by techniques known in the art. The lack of transcription can e.g. be caused by epigenetic changes (e.g. DNA methylation) or by loss-of-function mutations. A "loss-of-function" or "LOF" mutation as used herein is a mutation that prevents, reduces or abolishes the function of a gene product as opposed to a gain-of-function mutation that confers enhanced or new activity on a protein. A special form of a gain-of-function mutation (which is a particular part of this application) is a dominant negative mutation. A dominant negative mutation leads to the formation of a mutated protein (such as the truncated Imp1 protein from this application), but in contrast to its wild-type function, the dominant negative protein will have a loss-of-function effect, however, this effect is dominant. Therefore the mutation does not have to be homozygous to lead to the mutant phenotype. Both dominant negative or LOF mutations can be caused by a wide range of mutation types, including, but not limited to, a deletion of the entire gene or part of the gene, splice site mutations, frame-shift mutations caused by small insertions and deletions, nonsense mutations, missense mutations replacing an essential amino acid and mutations preventing correct cellular localization of the product.

As used here, "esters" are chemical compounds derived from an acid (organic or inorganic) in which at least one —OH (hydroxyl) group is replaced by an —O-alkyl (alkoxy) group. Usually, esters are derived from a carboxylic acid and an alcohol. The term "acetate esters" used in this application refers to esters formed from acetic acid or (from acetyl-CoA in yeast) and have the general formula $CH_3CO_2R$, wherein R is an organyl group. An "acetate ester" as referred to in this application is thus any carboxylic ester where the carboxylic acid component is acetic acid. Non-limiting examples of acetate esters are isoamyl acetate, ethyl acetate, phenylethyl acetate, propyl acetate and isobutyl acetate. "Isoamyl acetate", also known as isopentyl acetate, is an organic compound that is the ester formed from isoamyl alcohol and acetic acid. It is a colorless liquid that is only slightly soluble in water, but very soluble in most organic solvents, as alcohol. Isoamyl acetate has a strong odor which is also described as similar to both banana and pear. "Ethyl acetate" (systematically, ethyl ethanoate, commonly abbreviated EtOAc or EA) is the organic compound with the formula $CH_3$—COO—$CH_2$—$CH_3$, simplified to $C_4H_8O_2$. This colorless liquid has a characteristic sweet smell (similar to pear drops) and is used in glues, nail polish removers, decaffeinating tea and coffee, and cigarettes. Ethyl acetate is the ester of ethanol and acetic acid. "Propyl acetate", also known as propyl ethanoate, is a chemical compound used as a solvent and an example of an ester. This clear, colorless liquid is known by its characteristic odor of pears. Due to this fact, it is commonly used in fragrances and as a flavor additive. "Phenethyl acetate" is the ester resulting from the condensation of acetic acid and phenethyl alcohol. Like many esters, it is found in a range of fruits and biological products. It is a colorless liquid with a rose and honey scent and a raspberry-like taste. The chemical compound "isobutyl acetate", also known as 2-methylpropyl ethanoate (IUPAC name) or β-methylpropyl acetate, is a common solvent. It is produced from the esterification of isobutanol with acetic acid. It is used as a solvent for lacquer and nitrocellulose. Like many esters it has a fruity or floral smell at low concentrations and occurs naturally in raspberries, pears and other plants. At higher concentrations the odor can be unpleasant and may cause symptoms of central nervous system depression such as nausea, dizziness and headache.

"Limiting the production of an acetate ester" or "limiting acetate ester production" as used herein means that the eukaryotic cell (in particular embodiments the microorganism, in more particular embodiments the yeast), that comprises a disrupted, partially deleted or completely deleted subunit of the mitochondrial IMP complex produces less of at least one acetate ester, compared to a corresponding reference eukaryotic cell (in particular embodiments the microorganism, in more particular embodiments the yeast) lacking a disrupted, partially deleted or completely deleted subunit of the mitochondrial IMP complex. Synonyms for limiting are reducing, lowering, restricting, constraining, decreasing, lessening, diminishing. In particular embodiments, "limiting the production of an acetate ester" or "a reduced level of an acetate ester" means an at least 5%, at least 10%, at least 20%, at least 30%, at least 40%, at least 50%, at least 60%, at least 70%, at least 80%, at least 90%, at least 95% or 100% reduction in the production of said acetate ester. In other particular embodiments, "limiting the production of an acetate ester" or "a reduced level of an acetate ester" means obtaining a reduced production of said acetate ester of between 10% and 50%, of between 20% and 60%, of between 30% and 70% or of between 40% and 80% of the production of said acetate ester in conditions where a subunit of a mitochondrial IMP complex is not disrupted, not partially deleted or not completely deleted. The skilled person is familiar with methods to analyse and quantify the production of total and single acetate esters from a sample. In this application, acetate ester were quantified using head-space gas chromatography coupled with flame ionization detection (HS-GC-FID) as clearly described in the materials and method section.

To obtain an eukaryotic cell, microorganism or yeast with a disrupted, partially deleted or completely deleted subunit of the mitochondrial IMP complex, the truncated Imp1 proteins of current application can be used, as well the nucleic acid sequences (including the mutant alleles) that disrupt, partially delete or completely delete expression and/or activity of said subunit such as IMP1, IMP2 and/or SOM1.

In another embodiment, the use is provided of a disrupted, partially deleted or completely deleted subunit of a mitochondrial IMP complex to limit the production of at least one acetate ester in a eukaryotic organism or particularly during yeast fermentation. In a particular embodiment, said subunit is Imp1, Imp2 or Som1. In yet another embodiment, the use of a mitochondrial IMP complex is provided to limit the production of at least one acetate ester in a eukaryotic organism, more particularly the use of a non-functional mitochondrial IMP complex is provided to limit the production of at least one acetate ester in a eukaryotic organism. In particular embodiments, said acetate ester is one or more acetate ester selected from the list consisting of isoamyl acetate, ethyl acetate, phenylethyl acetate, propyl acetate and isobutyl acetate.

Also provided in this application, is the use of a disrupted, partially deleted or completely deleted subunit of a mitochondrial IMP complex or the use of a mitochondrial IMP complex or the use of a non-functional mitochondrial IMP complex to produce a fermented solution with a reduced level of at least one acetate ester. Also provided in this application, is the use of a disrupted, partially deleted or completely deleted subunit of a mitochondrial IMP complex or the use of a mitochondrial IMP complex or the use of a non-functional mitochondrial IMP complex to produce a flavour neutral alcohol. In another embodiment, the use of a disrupted, partially deleted or completely deleted subunit of a mitochondrial IMP complex or the use of a mitochondrial IMP complex or the use of a non-functional mitochondrial IMP complex is provided to produce a low acetate ester producing yeast.

Also provided is the use of a eukaryotic cell to limit or reduce the production of at least on acetate ester, wherein said eukaryotic cell comprises at least one disrupted, partially deleted or completely deleted subunit of the IMP complex. In a particular embodiment, said subunit is Imp1, Imp2 or Som1. In other particular embodiments, said acetate ester is one or more acetate ester selected from the list consisting of isoamyl acetate, ethyl acetate, phenylethyl acetate, propyl acetate and isobutyl acetate.

Also, this application envisages the combined use of a disrupted, partially deleted or completely deleted subunit of a mitochondrial IMP complex and the use of other mutant alleles also limiting acetate ester production to further limit or reduce acetate ester production in yeast. In particular embodiments, said subunit is Imp1, Imp2 or Som1. In other particular embodiments, said mutant alleles also limiting acetate ester production disrupt, partially delete or completely delete AFT1, AFT2, IMP1, IMP2, SOM1, COX9, COX12, CBS1, COR1 or QCR9 expression and/or function.

In an eighth aspect, the use of a truncated yeast Imp1 protein is provided to limit the production of at least one acetate ester in a eukaryotic organism or during yeast fermentation. In a particular embodiment, said truncated yeast Imp1 protein lacks residues 147-190 of a wild-type full length yeast Imp1 protein defined by SEQ ID No. 4. In another particular embodiment, said truncated yeast Imp1 proteins is a C-terminal truncated yeast Imp1 protein, wherein said protein comprises at least (or consists of) residues 10-148 of a functional or wild-type full length yeast Imp1 protein defined by SEQ ID No. 4. In another particular embodiment, said protein lacks amino acids 14-31 of a wild-type full length yeast Imp1 protein defined by SEQ ID No. 4 or comprises at least amino acid 32-148 of SEQ ID No. 2 or comprises at least amino acid 32-148 of SEQ ID No. 2 and further lacks amino acids 14-31 of a wild-type full length yeast Imp1 protein defined by SEQ ID No. 4. In another particular embodiment, said truncated yeast Imp1 protein comprises at least (or consists of) amino acid 1-153 of SEQ ID No. 2. In an even more particular embodiment, said truncated yeast Imp1 protein is depicted in SEQ ID No. 2, 6, 7 or 8. In this application also the use is provided of any of the truncated yeast Imp1 proteins described in the first aspect of the current application and in the embodiments of the first aspect to limit the production of at least one acetate ester in a eukaryotic organism. Also, the use is provided of any of the nucleic acid sequences described in the second aspect of current application and in the embodiments of the second aspect to limit the production of at least one acetate ester in a eukaryotic organism. In a most particular embodiment, the use of the nucleic acid sequence which is depicted in SEQ ID No. 1 is provided to limit the production of at least one acetate ester in a eukaryotic organism. Also, the use is provided of any of the chimeric genes described in the third aspect of current application and in the embodiments of the third aspect to limit the production of at least one acetate ester in a eukaryotic organism. In particular embodiments, said acetate ester is one or more acetate ester selected from the list consisting of isoamyl acetate, ethyl acetate, phenylethyl acetate, propyl acetate and isobutyl acetate.

In another embodiment, the use is provided of all described subject-matter of the first, second, third, fourth, fifth and six aspect and of all their accompanying embodiments to produce a fermented solution with a reduced level of at least one acetate ester or to produce a flavour neutral alcohol or to produce a low acetate ester producing yeast.

"Flavour neutral alcohol" as used herein is synonym for "odorless alcohol" or "essentially tasteless alcohol". The odor or flavour is the property of a substance that activates the sense of smell. Odor, smell, scent, stench all refer to sensations perceived through the nose by the olfactory nerves. Flavour neutral alcohols or odorless alcohols are sometimes used for blending fermented or alcoholised beverages but also for the industrial production of non-beverage alcohol, for example but not limited to bio-ethanol. Besides expression of a truncated Imp1 protein, other strategies are possible to limit acetate ester production. These strategies (e.g. the use of a mutant atf1 allele) are compatible with the means and methods described in the application to lower acetate ester production. Therefore, the above disclosed uses of the truncated yeast Imp1 proteins from the application or the nucleic acid sequences encoding those truncated yeast Imp1 proteins or the chimeric genes comprising those nucleic acid sequences, can be combined with the use of mutant alleles that further limit acetate ester production. Non-limiting example of said mutant alleles that further limit acetate ester production are ATF1, ATF2, IMP1, IMP2 and SOM1. In one embodiment, the combined use is thus provided of one of the truncated yeast IMP1 alleles of current application and mutant alleles that disrupt, partially delete or completely delete AFT1, AFT2, IMP1, IMP2 or SOM1.

In a ninth aspect, a method to limit or reduce the production of at least one acetate ester in a eukaryotic cell is provided, said method comprising the step of disrupting, partially deleting or completely deleting at least one subunit of a mitochondrial IMP complex in said eukaryotic cell. In a particular embodiment, said at least one subunit of a mitochondrial IMP complex is Imp1, Imp2 or Som1. In another particular embodiment, said at least one acetate ester is one or more acetate ester selected from the list consisting of isoamyl acetate, ethyl acetate, phenylethyl acetate, propyl acetate and isobutyl acetate.

In another embodiment, a method is provided to limit the production of at least one acetate ester in a eukaryotic cell, said method comprising the step of expressing a truncated yeast Imp1 protein in said eukaryotic cell, wherein said truncated yeast Imp1 protein lacks residues 147-190 of a wild-type full length yeast Imp1 protein defined by SEQ ID No. 4 or expressing a nucleic acid sequence encoding said truncated Imp1 protein in said eukaryotic cell or expressing a vector in said eukaryotic cell, wherein said vector comprises said nucleic acid sequence.

In another embodiment, a method is provided to limit the production of at least one acetate ester in a eukaryotic cell, said method comprising the step of expressing a C-terminal truncated yeast Imp1 protein, wherein said protein comprises at least (or consists of) residues 10-148 of a functional full length yeast Imp1 protein defined by SEQ ID No. 4 in said eukaryotic cell or expressing a nucleic acid sequence encoding said C-terminal truncated yeast Imp1 protein in said eukaryotic cell or expressing a vector in said eukaryotic cell, wherein said vector comprises said nucleic acid sequence. In another embodiment, a method is provided to limit the production of at least one acetate ester in a eukaryotic cell, said method comprising the step of expressing a truncated yeast Imp1 protein, wherein said truncated Imp1 protein comprises at least (or consists of) amino acid 1-153 of SEQ ID No. 2 in said eukaryotic cell or expressing a nucleic acid sequence encoding said truncated Imp1 protein in said eukaryotic cell or expressing a vector in said eukaryotic cell, wherein said vector comprises said nucleic acid sequence. In a more particular embodiment, a method is provided to limit the production of at least one acetate ester in a eukaryotic cell, said method comprising the step of expressing the nucleic acid sequence depicted in SEQ ID No. 1 or encoding a truncated Imp1 protein as depicted in SEQ ID No. 2, 6, 7 or 8 or expressing a vector containing one of said nucleic acid sequences in said eukaryotic cell.

In another embodiment, a method is provided to limit the production of at least one acetate ester in a eukaryotic cell, said method comprising the step of expressing in said eukaryotic cell a truncated yeast Imp1 protein lacking amino acids 14-31 of a wild-type full length yeast Imp1 protein defined by SEQ ID No. 4 or comprising at least amino acid 32-148 of SEQ ID No. 2 or comprising at least amino acid 32-148 of SEQ ID No. 2 and further lacking amino acids 14-31 of a wild-type full length yeast Imp1 protein defined by SEQ ID No. 4 or expressing in said eukaryotic cell a nucleic acid sequence encoding one of said truncated yeast Imp1 proteins in said eukaryotic cell or expressing cell a vector in said eukaryotic cell, wherein said vector comprises one of said nucleic acid sequences.

In another embodiment, a method is provided to limit the production of at least one acetate ester in a eukaryotic cell, said method comprising the step of expressing a chimeric gene in said eukaryotic cell, wherein said chimeric gene comprises a promoter which is active in a eukaryotic cell; a nucleic acid sequence encoding a truncated yeast Imp1 protein which lacks residues 147-190 of a wild-type full length yeast Imp1 protein defined by SEQ ID No. 4 or a nucleic acid sequence encoding a truncated yeast Imp1 protein comprising at least (or consists of) residues 10-148 of a functional full length yeast Imp1 protein defined by SEQ ID No. 4 or a nucleic acid sequence encoding a truncated Imp1 protein comprising at least (or consists of) amino acid 1-153 of SEQ ID No. 2 or a nucleic acid sequence encoding a truncated Imp1 protein lacking amino acids 14-31 of a wild-type full length yeast Imp1 protein defined by SEQ ID No. 4 or a nucleic acid sequence encoding a truncated Imp1 protein comprising at least amino acid 32-148 of SEQ ID No. 2 or a nucleic acid sequence encoding a truncated Imp1 protein comprising at least amino acid 32-148 of SEQ ID No. 2 and further lacking amino acids 14-31 of a wild-type full length yeast Imp1 protein defined by SEQ ID No. 4 or comprising the nucleic acid sequence depicted in SEQ ID No. 1 or encoding a truncated Imp1 protein as depicted in SEQ ID No. 2, 6, 7 or 8; and a 3' end region involved in transcription termination or polyadenylation.

In this application also more particular methods are provided to limit the production of at least one acetate ester in a eukaryotic cell, said methods comprising the step of expressing in said eukaryotic cell any of the truncated yeast Imp1 proteins described in the first aspect of the current application and in the embodiments of the first aspect or expressing in said eukaryotic cell any of the nucleic acid sequences described in the second aspect of current application and in the embodiments of the second aspect or expressing in said eukaryotic cell the nucleic acid sequence which is depicted in SEQ ID No. 1 or expressing in said eukaryotic cell any of the chimeric genes described in the third aspect of current application and in the embodiments of the third aspect. In particular embodiments, said acetate ester is one or more acetate ester selected from the list consisting of isoamyl acetate, ethyl acetate, phenylethyl acetate, propyl acetate and isobutyl acetate.

In a particular extension of the ninth aspect and of all embodiments of the ninth aspect, said eukaryotic cell is a yeast and said methods are methods to limit or reduce the production of at least one acetate ester during yeast fermentation. More particularly said yeast is a yeast useful for ethanol production, including, but not limited to *Saccharomyces*, *Zygosaccharomyces*, *Brettanomyces* and *Kluyveromyces*. Even more particularly, said yeast is a *Saccharomyces* sp., most particularly it is a *Saccharomyces cerevisiae* sp. Said yeast strains are particularly useful for industrial fermentation at conditions wherein too much acetate esters, more particularly too much ethyl acetate is produced.

Also in this application, methods are provided to produce a fermented solution with a reduced level of at least one acetate ester, the method comprising the step of expressing in yeast any of the truncated yeast Imp1 proteins described in the first aspect of the current application and in the embodiments of the first aspect or expressing in yeast any of the nucleic acid sequences described in the second aspect of current application and in the embodiments of the second aspect or expressing in yeast the nucleic acid sequence which is depicted in SEQ ID No. 1 or encoding a truncated yeast Imp1 protein as depicted in SEQ ID No. 2, 6, 7 or 8 or expressing in yeast any of the chimeric genes described in the third aspect of current application and in the embodiments of the third aspect. In particular embodiments, said reduced level is at least 5%, at least 10%, at least 15%, at least 20%, at least 30%, at least 40%, at least 50%, at least 60%, at least 70%, at least 80%, at least 90%, at least 95%, or 100% less or said reduced level is between 10% and 50%, of between 20% and 60%, of between 30% and 70% or of between 40% and 80% less compared to a yeast not expressing any of the truncated yeast Imp1 proteins described in the first aspect of the current application and in the embodiments of the first aspect or any of the nucleic acid sequences described in the second aspect of current application and in the embodiments of the second aspect or not expressing the nucleic acid sequence which is depicted in SEQ ID No. 1 or encoding a truncated Imp1 protein as depicted in SEQ ID No. 2, 6, 7 or 8 or not expressing any of the chimeric genes described in the third aspect of current application and in the embodiments of the third aspect. In particular embodiments, said acetate ester is one or more acetate ester selected from the list consisting of isoamyl acetate, ethyl acetate, phenylethyl acetate, propyl acetate and isobutyl acetate. In other particular embodiments, said yeast is a yeast useful for ethanol production, including, but not limited to *Saccharomyces, Zygosaccharomyces, Brettanomyces* and *Kluyveromyces*. Even more particularly, said yeast is a *Saccharomyces* sp., most particularly it is a *Saccharomyces cerevisiae* sp. Said yeast strains are particularly useful for industrial fermentation at conditions wherein too much acetate esters, more particularly too much ethyl acetate is produced.

Also in this application, methods are provided to produce or ferment a flavour neutral alcohol, the method comprising the step of expressing in yeast any of the truncated yeast Imp1 proteins described in the first aspect of the current application and in the embodiments of the first aspect or expressing in yeast any of the nucleic acid sequences described in the second aspect of current application and in the embodiments of the second aspect or expressing in yeast the nucleic acid sequence which is depicted in SEQ ID No. 1 or encoding a truncated Imp1 protein as depicted in SEQ ID No. 2, 6, 7 or 8 or expressing in yeast any of the chimeric genes described in the third aspect of current application and in the embodiments of the third aspect. In particular embodiments, said reduced level is at least 5%, at least 10%, at least 15%, at least 20%, at least 30%, at least 40%, at least 50%, at least 60%, at least 70%, at least 80%, at least 90%, at least 95%, or 100% less or said reduced level is of between 10% and 50%, of between 20% and 60%, of between 30% and 70% or of between 40% and 80% less compared to a yeast not expressing any of the truncated yeast Imp1 proteins described in the first aspect of the current application and in the embodiments of the first aspect or any of the nucleic acid sequences described in the second aspect of current application and in the embodiments of the second aspect or not expressing the nucleic acid sequence which is depicted in SEQ ID No. 1 or encoding a truncated Imp1 protein as depicted in SEQ ID No. 2, 6, 7 or 8 or not expressing any of the chimeric genes described in the third aspect of current application and in the embodiments of the third aspect. In particular embodiments, said acetate ester is one or more acetate ester selected from the list consisting of isoamyl acetate, ethyl acetate, phenylethyl acetate, propyl acetate and isobutyl acetate. In other particular embodiments, said yeast is a yeast useful for ethanol production, including, but not limited to *Saccharomyces, Zygosaccharomyces, Brettanomyces* and *Kluyveromyces*. Even more particularly, said yeast is a *Saccharomyces* sp., most particularly it is a *Saccharomyces cerevisiae* sp. Said yeast strains are particularly useful for industrial fermentation at conditions wherein too much acetate esters, more particularly too much ethyl acetate is produced.

In a particular extension of the methods described in the ninth aspect or in one of the accompanying embodiments from aspect nine, the methods further include a step of quantifying at least one acetate ester.

In a tenth aspect, a method to produce a low acetate ester producing yeast is provided, said method comprises the step of crossing two parental yeast strains, wherein at least one parental yeast strain comprises at least one disrupted, partially deleted or complete deleted subunit of a mitochondrial IMP complex. In more particular embodiments, said at least one parental yeast strain comprises at least a disrupted, partially deleted or complete deleted IMP1, IMP2 or SOM1. In even more particularly embodiments, said at least one parental yeast strain comprises a truncated yeast Imp1 protein which lacks residues 147-190 of a wild-type full length yeast Imp1 protein defined by SEQ ID No. 4 or comprises a nucleic acid sequence encoding said truncated Imp1 protein or comprises a vector comprising said nucleic acid sequence. In another equally particularly embodiment, said at least one parental yeast strain comprises a C-terminal truncated yeast Imp1 protein, wherein said protein comprises at least (or consists of) residues 10-148 of a functional full length yeast Imp1 protein defined by SEQ ID No. 4 or comprises a nucleic acid sequence encoding said C-terminal truncated yeast Imp1 protein or comprises a vector comprising said nucleic acid sequence. In another equally particular embodiment, said at least one parental yeast strain comprises a truncated Imp1 protein lacking amino acids 14-31 of a wild-type full length yeast Imp1 protein defined by SEQ ID No. 4 or a truncated Imp1 protein comprising at least amino acid 32-148 of SEQ ID No. 2 or a truncated Imp1 protein comprising at least amino acid 32-148 of SEQ ID No. 2 and further lacking amino acids 14-31 of a wild-type full length yeast Imp1 protein defined by SEQ ID No. 4 or comprises a nucleic acid sequence encoding one of said truncated yeast Imp1 proteins or comprises a vector comprising one of said nucleic acid sequences. In another equally particularly embodiment, said at least one parental yeast strain comprises a truncated yeast Imp1 protein, wherein said truncated Imp1 protein comprises at least (or consists of) amino acid 1-153 of SEQ ID No. 2 or comprises a nucleic acid sequence encoding said truncated Imp1 protein or comprises a vector comprising said nucleic acid sequence. In another equally particularly embodiment, said at least one parental yeast strain comprises the nucleic acid sequence depicted in SEQ ID No. 1 or comprises a vector containing said nucleic acid sequence.

In even other equally particularly embodiments, said at least one parental yeast strain comprises chimeric gene comprising a promoter which is active in a eukaryotic cell; a nucleic acid sequence encoding a truncated yeast Imp1 protein which lacks residues 147-190 of a wild-type full length yeast Imp1 protein defined by SEQ ID No. 4 or a nucleic acid sequence encoding a truncated yeast Imp1 protein comprising at least (or consists of) residues 10-148 of a functional full length yeast Imp1 protein defined by SEQ ID No. 4 or a nucleic acid sequence encoding a truncated Imp1 protein comprising at least (or consists of)

amino acid 1-153 of SEQ ID No. 2 or comprising the nucleic acid sequence depicted in SEQ ID No. 1 or encoding a truncated Imp1 protein as depicted in SEQ ID No. 2, 6, 7 or 8; and a 3' end region involved in transcription termination or polyadenylation.

In other embodiments, methods to produce a low acetate ester producing yeast are provided, said methods comprise the step of crossing two parental yeast strains, wherein at least one parental yeast strain comprises any of the truncated yeast Imp1 proteins described in the first aspect of the current application and in the embodiments of the first aspect or comprises any of the nucleic acid sequences described in the second aspect of current application and in the embodiments of the second aspect or comprises the nucleic acid sequence which is depicted in SEQ ID No. 1 or encoding the truncated Imp1 protein as depicted in SEQ ID No. 2, 6, 7 or 8 or comprises any of the chimeric genes described in the third aspect of current application and in the embodiments of the third aspect. In particular embodiments, said acetate ester is one or more acetate ester selected from the list consisting of isoamyl acetate, ethyl acetate, phenylethyl acetate, propyl acetate and isobutyl acetate.

A "low acetate ester producing yeast" as used in this application, refers to a yeast strain that produces a lower amount of at least one acetate ester compared to a wild-type yeast strain. Said wild-type yeast strain is a yeast strain which was not selected and/or engineered to produce a low level of acetate esters. In particular embodiments, said lower amount is an at least 5%, at least 10%, at least 15%, at least 20%, at least 30%, at least 40%, at least 50%, at least 60%, at least 70%, at least 80%, at least 90%, at least 95%, or 100% smaller amount or a between 10% and 50%, or a between 20% and 60%, or a between 30% and 70% or a between 40% and 80% smaller amount less compared to said wild-type yeast strain. In alternative embodiments, said lower amount is a statistical significant lower amount of at least one acetate ester. "Statistical significant" as used here refers to a p-value of less than 0.5, which is a commonly accepted level for statistical significance and well known by the person skilled in the art.

In an eleventh aspect, a screening method to obtain a low acetate ester producing yeast is provided, comprising:
  determining the expression and/or activity of at least one subunit of a mitochondrial IMP complex in a yeast strain;
  selecting a yeast strain wherein the expression and/or activity of said at least one subunit is disrupted, partially deleted or completely deleted;
  to obtain a low acetate ester producing yeast.

In particular embodiments, said at least one subunit of a mitochondrial IMP complex is Imp1, Imp2 or Som1. Means and methods to determine the expression of protein-encoding genes or to determine the activity of proteins are well-known in the art. Determining protein activity is particularly well-documented for Imp1 and Imp2, both subunits of the IMP complex with proteolytic activity but non-overlapping substrate specificities (Esser et al 2004 Mol Gen Genomics 271:616-626). Imp1 has been shown to catalyse the maturation of cytochrome oxidase subunit 2 (Cox2), cytochrome b2 (Cytb2), the 32 kDa form of NADH-dependent cytochrome b5 reductase (Mcr1[32]) and the mitochondrial FAD-dependent glyceral-3-phosphate dehydrogenase (Gut2) (Esser et al 2004 Mol Gen Genomics 271:616-626). Imp2 participates in the maturation of cytochrome c1. Detection and efficiency of the processing of the Imp1 and Imp2 substrates can thus be used to determine the activity of said IMP complex subunits as was discussed in Esser et al (2004 Mol Gen Genomics 271:616-626), incorporated here as reference.

In current application we have convincingly shown that a non-functional IMP complex has severe effects on the production of acetate esters in yeast. The mitochondrial IMP complex functions in the respiration chain and in line with our findings, genetic and pharmacological inhibition of respiration in yeast has the same effect on acetate ester production (Example 9). This means that current application discloses a much broader and more general concept of how acetate ester production in yeast can be reduced. Therefore, and in a twelfth aspect, the use of a mutant yeast allele is provided to limit the production of at least one acetate ester during yeast fermentation or to produce a fermented solution with a reduced level of at least one acetate ester or to produce a flavour neutral alcohol, wherein said mutant yeast allele inhibits or reduces respiration in yeast. This is equivalent as saying that a method is provided to limit the production of at least one acetate ester during yeast fermentation or to produce a fermented solution with a reduced level of at least one acetate ester or to produce a flavour neutral alcohol, said method comprising the step of expressing a mutant yeast allele in a yeast culture, wherein said mutant yeast allele inhibits or reduces respiration in said yeast culture. Non-limiting examples of yeast alleles involved in respiration are genes encoding subunits of the COX complex (e.g. COX9, COX12), genes encoding subunits of the HAP complex (e.g. HAP2, HAP4) or genes involved in the mitochondrial function (e.g. CBS1, COR1, QCR9). Hence, in a particular embodiment, the use of a yeast strain is provided to limit the production of at least one acetate ester during yeast fermentation or to produce a fermented solution with a reduced level of at least one acetate ester or to produce a flavour neutral alcohol, wherein said yeast strain comprises a disrupted, partially deleted or completely deleted COX complex, or even more particularly wherein said yeast strain comprises a disrupted, partially deleted or completely deleted COX9 or COX12 allele. In another particular embodiment, the use of a yeast strain is provided to limit the production of at least one acetate ester during yeast fermentation or to produce a fermented solution with a reduced level of at least one acetate ester or to produce a flavour neutral alcohol, wherein said yeast strain comprises a disrupted, partially deleted or completely deleted CBS1, COR1 or QCR9 allele.

In a thirteenth aspect, the use of an inhibitor of cellular respiration is provided to limit the production of at least one acetate ester in a eukaryotic cell or during yeast fermentation. Also the use of an inhibitor of cellular respiration is provided to produce a fermented solution with a reduced level of at least one acetate ester or to produce a flavour neutral alcohol. In one embodiment, said inhibitor is a compound, more particularly a chemical compound. Hence, the use of a compound or chemical compound is provided to limit the production of at least one acetate ester during yeast fermentation or to produce a fermented solution with a reduced level of at least one acetate ester or to produce a flavour neutral alcohol, where said compound is an inhibitor of respiration in yeast. This is equivalent as saying that a method is provided to limit the production of at least one acetate ester during a yeast fermentation or to produce a fermented solution with a reduced level of at least one acetate ester or to produce a flavour neutral alcohol, said method comprising the step of adding or administrating a compound to a yeast culture, wherein said compound inhibits respiration in yeast. Said compound can be chemically synthesized or can be a biological compound. In particular embodiments, said compound is antimycin, carbonyl cyanide 3-chlorophenylhydrazone or oligomycin. In most particular embodiments, said compound is antimycin.

In another embodiment, said inhibitor is a nucleic acid sequence that disrupts, partially deletes or completely deletes cellular respiration in a eukaryotic cell. Non-limiting examples of said nucleic acid sequence are besides mutant alleles, also suppressors and inhibitors of respiration selected from the list consisting of an antisense oligomer, a miRNA, a siRNA, a shRNA, a gapmer, a morpholino, a locked nucleic acid, a peptide nucleic acid, ribozyme, ZFN, a TALEN, a CRISPR-Cas, a CRISPR-C2c2 and a meganuclease. Said nucleic acid sequences are then expressed in said eukaryotic cell to inhibit or reduce the expression of genes involved in cellular respiration. Hence, the use of a nucleic acid sequence that disrupts, partially deletes or completely deletes cellular respiration in a eukaryotic cell is provided to limit the production of at least one acetate ester during yeast fermentation or to produce a fermented solution with a reduced level of at least one acetate ester or to produce a flavour neutral alcohol. In a particular embodiment, said nucleic acid sequence is selected from the list consisting of SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27 and SEQ ID No. 28. In another embodiment, a method is provided to limit the production of at least one acetate ester during a yeast fermentation or to produce a fermented solution with a reduced level of at least one acetate ester or to produce a flavour neutral alcohol, said method comprising the step of disrupting, partially deleting or completely deleting a nucleic acid sequence, wherein said nucleic acid sequence encodes a protein in the respiratory chain. In particular embodiments, said nucleic acid sequence is a gene that is needed for cellular respiration in a eukaryotic cell or is needed for the synthesis of respiratory enzymes in a eukaryotic cell.

The application also provides the use of a microorganism wherein cellular respiration is disrupted, partially deleted or completely deleted to limit the production of at least one acetate ester during fermentation or to produce a fermented solution with a reduced level of at least one acetate ester or to produce a flavour neutral alcohol. Cellular respiration can be disrupted, partially deleted or completely deleted by adding a chemical or biological compound to the fermentation medium. Non-limiting examples of such compounds are antimycin, carbonyl cyanide 3-chlorophenylhydrazone or oligomycin. However, cellular respiration in a microorganism can also be disrupted, partially deleted or completely deleted by disrupting, partially deleting or completely deleting a gene or protein which is needed for cellular respiration. Said gene or protein can be essential in the respiratory chain or can be a modulator for the production of respiratory enzymes. Non-limiting examples of such genes are the cytochrome c oxidase (COX) genes such as COX9 and COX12 or the cytochrome B synthesis (CBS) genes such as CBS1 or genes encoding subunits of the ubiquinol-cytochrome C oxidoreductase complex such as COR1 and QCR9. Means and methods to disrupt, partially delete or completely delete specific genes are described earlier in this application and are well-known by the skilled person.

COX genes encode subunits of the cytochrome c oxidase enzyme, which is a large transmembrane protein complex found in bacteria and in the mitochondria of eukaryotes. It is the last enzyme in the respiratory electron transport chain of mitochondria (or bacteria) located in the mitochondrial (or bacterial) membrane. It receives an electron from each of four cytochrome c molecules, and transfers them to one oxygen molecule, converting molecular oxygen to two molecules of water. In the process, it binds four protons from the inner aqueous phase to make water, and in addition translocates four protons across the membrane, helping to establish a transmembrane difference of proton electrochemical potential that the ATP synthase then uses to synthesize ATP. The COX complex is a multimeric enzyme formed by subunits of dual genetic origin whose assembly is intricate and highly regulated. In addition to the structural subunits, a large number of accessory factors are required to build the holoenzyme. The function of these factors is required in all stages of the assembly process and affecting their expression and/or activity and/or folding will affect the function of COX and thus of cellular respiration. All factors that could affect the functioning of COX are thus provided in this application to reduce acetate ester production during fermentation.

CBS1 or cytochrome B synthesis 1 is a membrane protein that interacts with translating ribosomes and translationally activates the COB mRNA.

The ubiquinol-cytochrome c oxidoreductase complex sometimes called the cytochrome bc1 complex, and at other times complex III, is the third complex in the electron transport chain (EC 1.10.2.2), playing a critical role in biochemical generation of ATP (oxidative phosphorylation). Complex III is a multisubunit transmembrane protein encoded by both the mitochondrial (cytochrome b) and the nuclear genomes (all other subunits). Complex III is present in the mitochondria of all animals and all aerobic eukaryotes and the inner membranes of most eubacteria. The bc1 complex contains several subunits (such as QCR9), core proteins (such as COR1) and low-molecular weight proteins.

COR1 stands for core protein 1 of QH2 cytochrome c reductase while QCR9 stands for subunit 9 of ubiquinol cytochrome-c reductase.

All living cells, including yeast, need energy for cellular processes such as pumping molecules into or out of the cell or synthesizing needed molecules. Cellular respiration is the process that cells use to transfer energy from the organic molecules in food to ATP. ATP is a special molecule which provides energy in a form that cells can use for cellular processes. The following equation summarizes the chemical changes that occur in cellular respiration of the monosaccharide glucose when oxygen is available. $C_6H_{12}O_6$ (glucose)+6 $O_2$ (oxygen)→6 $CO_2$ (carbon dioxide)+6 $H_2O$ (water)+ATP (energy) In particular embodiments of the thirteenth aspect, said eukaryotic cell is a yeast, more particularly a yeast useful for ethanol production, including, but not limited to *Saccharomyces, Zygosaccharomyces, Brettanomyces* and *Kluyveromyces*. Even more particularly, said yeast is a *Saccharomyces* sp., most particularly it is a *Saccharomyces cerevisiae* sp. Said yeast strains are particularly useful for industrial fermentation at conditions wherein too much acetate esters, more particularly too much ethyl acetate is produced.

In a particular extension of any of the aspects 7 till 13 described above or of any of the embodiments of said aspects, the said uses or methods to limit the production of at least one acetate ester in a eukaryotic cell or to produce a fermented solution with reduced levels of at least one acetate ester or to produce a flavour neutral alcohol, do not reduce or negatively influence alcohol and more particular ethanol production. In a most particular embodiment of the above, the truncated Imp1 yeast protein is not the truncated yeast Imp1 protein as depicted in SEQ ID No. 5.

We have also identified and isolated a novel mutant allele from the *Saccharomyces cerevisiae* ATF1 gene that when expressed in industrial *S. cerevisiae* strains limits the production of acetate esters including ethyl acetate. Therefore, in one aspect, this application provides a mutant yeast ATF1 allele comprising a mutated nucleic acid at position 221 of the open reading frame sequence depicted in SEQ ID No. 10, wherein said mutation is a frame shift mutation, a nonsense mutation or a missense mutation. In a particular embodiment, said mutation is a frame shift mutation. This is equivalent as saying that a nucleic acid sequence encoding a mutant yeast Atf1 protein is provided, wherein said nucleic acid sequence comprises a frame shift mutation at position 221. In an even more particular embodiment, a mutant yeast ATF1 allele is provided, wherein said allele is depicted in SEQ ID No. 9.

"Position 221" as used herein refers to the nucleic acid that is 220 positions removed downstream from the first nucleotide (i.e. adenosine) from the start codon. This position is indicated in SEQ ID No. 9 by an underlined space.

In another aspect, a eukaryotic cell comprising a mutant yeast ATF1 allele is provided, wherein said mutant yeast ATF1 allele comprises a mutated nucleic acid at position 221 of the open reading frame sequence depicted in SEQ ID No. 10. In a particular embodiment, said mutation is a frame shift mutation. This is equivalent as saying that a eukaryotic cell comprising a nucleic acid sequence encoding a mutant yeast Atf1 protein is provided, wherein said nucleic acid sequence comprises a frame shift mutation at position 221. In an even more particular embodiment, a eukaryotic cell comprising a mutant yeast ATF1 allele is provided, wherein said allele is depicted in SEQ ID No. 9.

In particular embodiments, said eukaryotic cell is a yeast, more particularly a yeast useful for ethanol production, including, but not limited to *Saccharomyces*, *Zygosaccharomyces*, *Brettanomyces* and *Kluyveromyces*. Even more particularly, said yeast is a *Saccharomyces* sp., most particularly it is a *Saccharomyces cerevisiae* sp. Said yeast strains are particularly useful for industrial fermentation at conditions wherein too much acetate esters, more particularly too much ethyl acetate is produced. Therefore, the application also envisages fermented solutions comprising yeast, wherein said yeast comprises a mutant yeast ATF1 allele comprising a mutated nucleic acid at position 221 of the open reading frame sequence depicted in SEQ ID No. 10 or wherein said yeast comprises a nucleic acid sequence encoding a mutant yeast Atf1 protein, wherein said nucleic acid sequence comprises a frame shift mutation at position 221 or wherein said yeast comprises a mutant yeast ATF1 allele as depicted in SEQ ID No. 9. In particular embodiments, said fermented solution is a fermented beverage, for example but not limited to beer. In other particular embodiments, said fermented solution is a non-food or non-beverage solution, for example but not limited bio-ethanol.

In another aspect, the use of a mutant yeast ATF1 allele is provided to limit or reduce the production of at least one acetate ester in a eukaryotic organism or to produce a fermented solution with a reduced level of at least one acetate ester or to produce a flavour neutral alcohol, wherein said mutant yeast ATF1 allele comprises a mutated nucleic acid at position 221 of the open reading frame sequence depicted in SEQ ID No. 10. In a particular embodiment, said mutation is a frame shift mutation. Also, the use is provided of a nucleic acid sequence encoding a mutant yeast Atf1 protein to limit the production of at least one acetate ester in a eukaryotic organism or to produce a fermented solution with a reduced level of at least one acetate ester or to produce a flavour neutral alcohol, wherein said nucleic acid sequence comprises a frame shift mutation at position 221. In a particular embodiment, said nucleic acid sequence is depicted in SEQ ID No. 9. In another embodiment, the use of a yeast is provided to limit the production of at least one acetate ester during yeast fermentation or to produce a fermented solution with a reduced level of at least one acetate ester or to produce a flavour neutral alcohol, wherein said yeast comprises a mutant yeast ATF1 allele, wherein said mutant yeast ATF1 allele comprises a mutated nucleic acid at position 221 of the open reading frame sequence depicted in SEQ ID No. 10. In a particular embodiment, said mutation is a frame shift mutation. This is equivalent as saying that the use of a yeast is provided to limit the production of at least one acetate ester during yeast fermentation or to produce a fermented solution with a reduced level of at least one acetate ester or to produce a flavour neutral alcohol, wherein said yeast comprises a nucleic acid sequence comprising a frame shift mutation at position 221. In another embodiment, the use of a yeast is provided to limit the production of at least one acetate ester during yeast fermentation or to produce a fermented solution with a reduced level of at least one acetate ester or to produce a flavour neutral alcohol, wherein said yeast comprises the mutant yeast ATF1 allele depicted in SEQ ID No. 9.

In another embodiment, the use of a mutant yeast ATF1 allele, wherein said allele comprises a mutated nucleic acid at position 221 of the open reading frame sequence depicted in SEQ ID No. 10 or the use of a nucleic acid depicted in SEQ ID No. 9 or the use of a yeast comprising said mutant yeast ATF1 allele or said nucleic acid is provided, to produce a low acetate ester producing yeast. In particular embodiments, said one or more acetate ester is selected from the list consisting of isoamyl acetate, ethyl acetate, phenylethyl acetate, propyl acetate and isobutyl acetate.

In another aspect, a method to limit or reduce the production of at least one acetate ester during yeast fermentation or to produce a fermented solution with a reduced level of at least one acetate ester or to produce a flavour neutral alcohol is provided, said method comprising the step of expressing a mutant yeast ATF1 allele comprising a mutated nucleic acid at position 221 of the open reading frame sequence depicted in SEQ ID No. 10, wherein in a particular embodiment said mutation is a frame shift mutation. In a more particular embodiment, a method to limit or reduce the production of at least one acetate ester during yeast fermentation or to produce a fermented solution with a reduced level of at least one acetate ester or to produce a flavour neutral alcohol is provided, said method comprising the step of expressing the mutant yeast ATF1 allele depicted in SEQ ID No. 9. Throughout the application said one or more acetate ester is in particular embodiments selected from the list consisting of isoamyl acetate, ethyl acetate, phenylethyl acetate, propyl acetate and isobutyl acetate.

This application envisages also the combined use of the disclosed mutant yeast ATF1 allele and the use of other mutant alleles limiting acetate ester production to further limit or reduce acetate ester production in yeast. Examples of such mutant alleles are disrupted, partially deleted or completely deleted subunits of a mitochondrial IMP complex, more particularly of Imp1, Imp2 or Som1, or even more particularly the mutant Imp1 alleles disclosed in this application. Other non-limiting examples of mutant alleles limiting acetate ester production are disrupted, partially deleted or completely deleted AFT1, AFT2, COX9, COX12, CBS1, COR1 or QCR9 alleles.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1: Selection of High- and Low-Isoamyl Acetate Producing Parental Strains to Identify QTL's Involved in Acetate Ester Production Previously, the aroma profile and genetic relatedness of 301 different *Saccharomyces* yeast strains was analysed and led to the identification of a strain (i.e. Y354) with exceptionally high isoamyl acetate production (Steensels et al. 2014, Applied Environ Microbiol 80:6965-6975). A strain, more precisely strain Y242, with exceptionally low isoamyl acetate production was also identified. Here, strains Y354 and Y242 were used as parental strains for the development of a hybrid strain (Table 1). First, the parental strains were sporulated to obtain haploid segregants. Given that complex, polygenic traits can vary significantly among meiotic segregants, the isoamyl acetate production was tested in the resulting segregants and compared to the parental strains. Segregants having (at least equally) high (in case of Y354) or low (in case of Y242) isoamyl acetate production could be identified (Table 1).

TABLE 1

Overview of the parental strains selected for the developed hybrid.

| Strain code | Strain info | Isoamyl acetate (mg/L) |
|---|---|---|
| Y354 | Natural beer yeast | 1.620 |
| Y354-18B | Y354 segregant used as parent | 2.187 |
| Y242 | Natural bioethanol yeast | 0.650 |
| Y242-6A | Y242 segregant used as parent | 0.488 |

Production of isoamyl acetate (which was the main selection criterion) of the natural strain and the segregants used to make the hybrid are given. Isoamyl acetate was measured in medium containing 1% (w/v) yeast extract, 2% (w/v) peptone and 10% (w/v) glucose, after a 1-week static fermentation in 150 mL incubated at 30° C.

Example 2: Selection of High Acetate Ester-Producing Segregants from a Y354-Y242 Hybrid In a next step, the haploid segregants Y354-18B and Y242-6A (Table 1) were used to develop a hybrid, which from hereon is referred to as 'Hybrid A'. After sporulation, the resulting haploid segregants of Hybrid A were screened for isoamyl acetate production. In total, 480 segregants were screened in small-scale fermentations for isoamyl acetate production. FIG. 1 gives an overview of the isoamyl acetate production of all segregants. 28 segregants showing high isoamyl acetate production were selected. We opted to select for high production, as the resolution within this group was higher (see FIG. 1). These segregants were first genetically screened on mating type and ploidy. Segregants showing aberrant features (e.g. diploid mating type or non-haploid ploidy) were excluded from the selection. The other segregants were pooled and genomic DNA was extracted. Subsequently, the segregant pool as well as the haploid parental strains were sequenced. To correct for involuntarily selection of phenotypes conferring a selective advantage in this experimental setup (such as high sporulation efficiency and high spore viability), pools with randomly selected segregants were also included.

Example 3. Identification of QTLs Determining High Isoamyl Acetate Production

Figure 2:
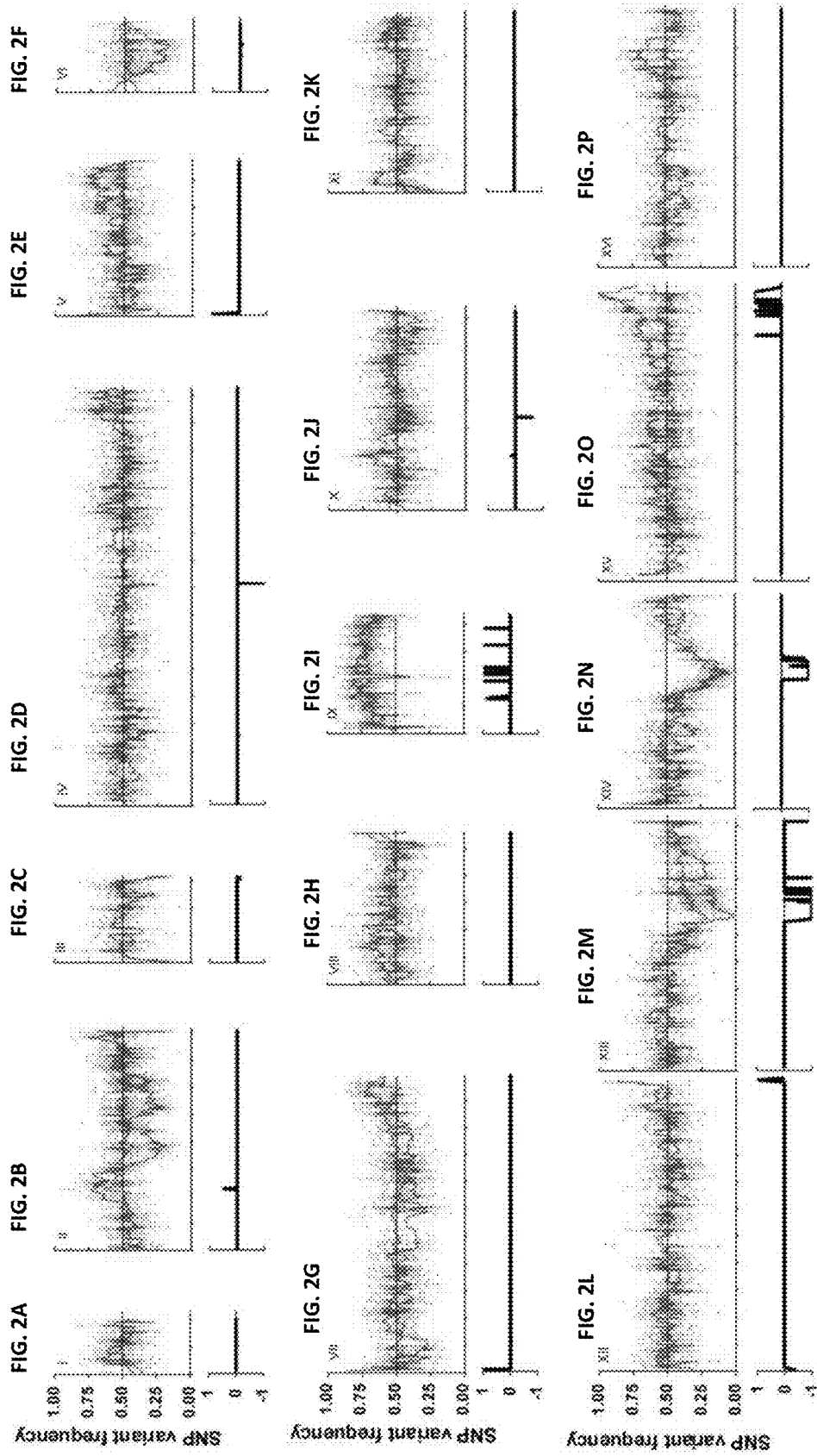
FIGS. 2A-2P. Genetic mapping of QTLs involved in high IA production, determined by pooled segregant whole-genome sequence analysis. The nucleotide frequency of the quality-selected SNPs in the sequence of the pool was plotted against the chromosomal position (green dots: selected pool, red dots: random pool). Each panel represents one chromosome. Unit scales of the X-axis are identical and represent 100 kbp. The green and red lines represent trendlines, calculated by the moving average of the 5 neighboring dots of the same color. The black horizontal line indicates a normal segregation of 50%. Significant deviations [as determined by EXPLoRA (Duitama et al., 2014 BMC genomics 15: 1), from this 50:50 ratio indicate candidate QTLs, except when the same pattern is observed in the random pool. Upward deviations indicate bias towards the allele of Y354, while downward deviations indicate bias towards Y242.
Figure 3:
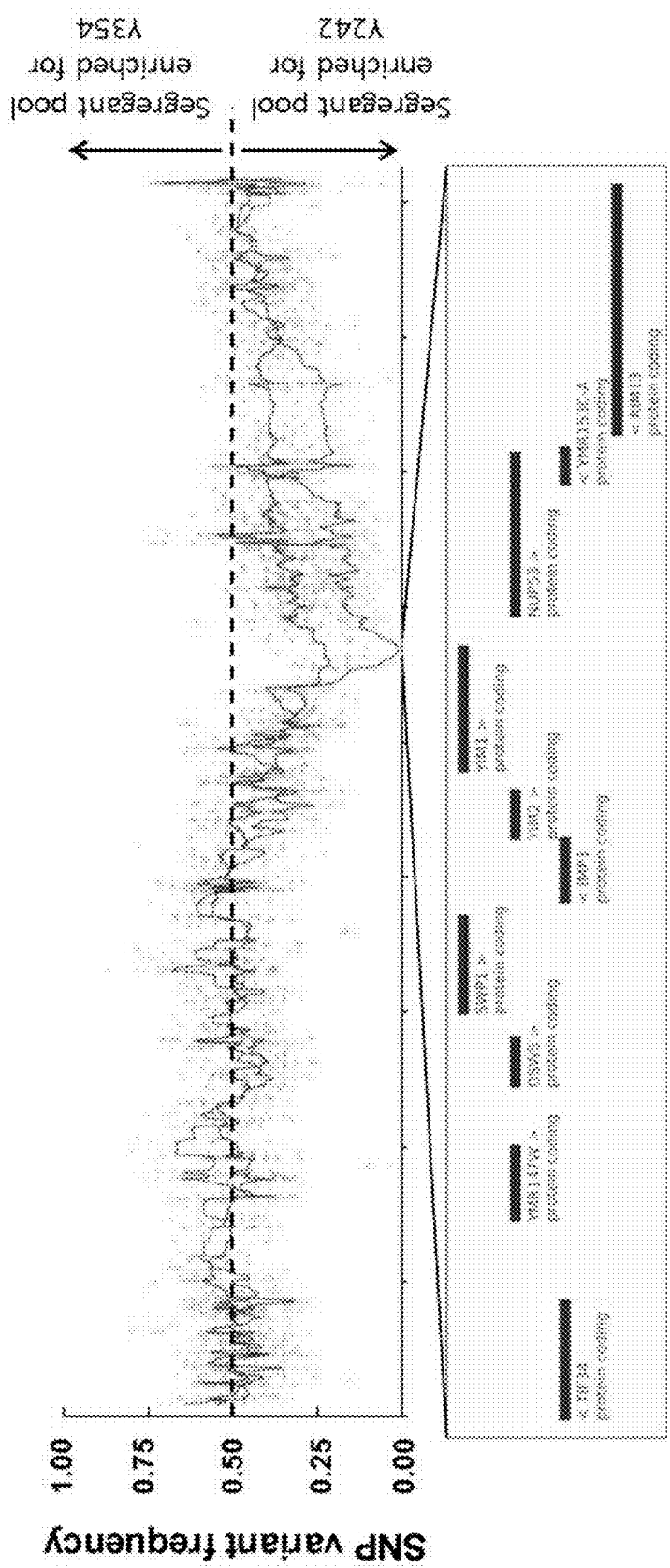
FIG. 3. Overview of the genes present in QTL1. QTL1 is located on chromosome XIII (ChrXIII:557,000-568,000). The nucleotide frequency of the quality-selected SN Ps in the sequence of the segregant pool was plotted against the chromosomal position (green dots: selected pool, red dots: random pool). The green and red lines represent trendlines, calculated by the moving average of the 5 neighboring dots of the same color. The black horizontal line indicates a normal segregation of 50%. Significant deviations [as determined by EXPLoRA (Duitama et al., 2014 BMC genomics 15: 1), from this 50:50 ratio indicate candidate QTLs, except when the same pattern is observed in the random pool. Upward deviations indicate bias towards the allele of Y354, while downward deviations indicate bias towards Y242.
Figure 4:
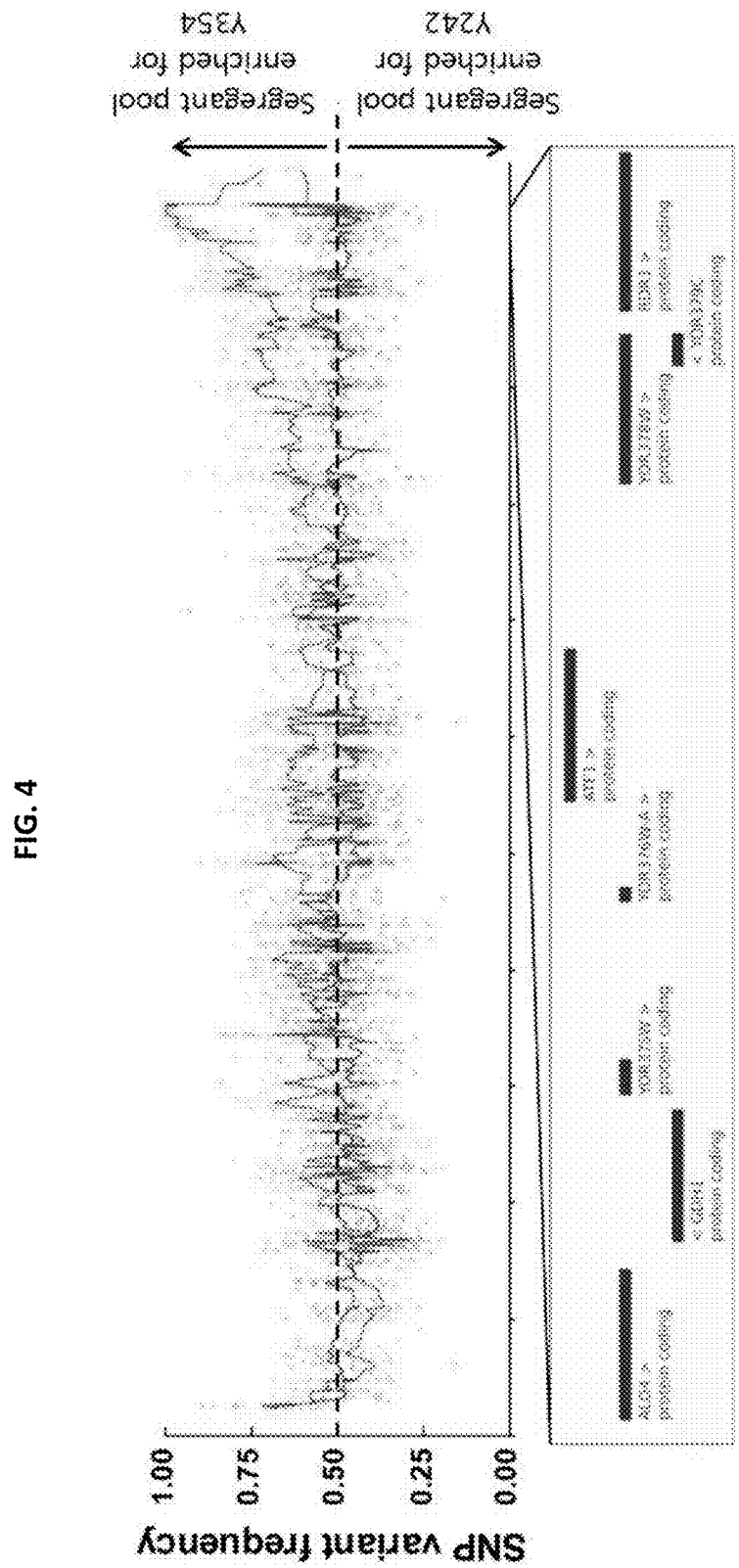
FIG. 4. Overview of the genes present in QTL2. QTL2 is located on chromosome XV (ChrXV:1,040,000-1,053,000). The nucleotide frequency of the quality-selected SNPs in the sequence of the segregant pool was plotted against the chromosomal position (green dots: selected pool, red dots: random pool). The green and red lines represent trendlines, calculated by the moving average of the 5 neighboring dots of the same color. Significant deviations [as determined by EXPLoRA (Duitama et al., 2014 BMC genomics 15: 1), from the 50:50 ratio indicate candidate QTLs, except when the same pattern is observed in the random pool. Upward deviations indicate bias towards the allele of Y354, while downward deviations indicate bias towards Y242.

For the pooled segregants, the SNP (single nucleotide polymorphism) variant frequency was determined using NGSEP (Duitama et al. 2014 Nucleic acids research 42: e44-e44) and the probability of linkage was calculated using EXPLoRA (Duitama et al. 2014 BMC genomics 15: 1). The results are shown in FIG. 2. Statistical analysis was performed using EXPLoRA (Extraction of over-represented alleles in BSA), an algorithm for BSA (Bulk Segregant Analysis) data analysis that explicitly models the dependency between neighboring marker sites by exploiting the properties of linkage disequilibrium through a Hidden Markov Model (HMM) (for more information, see Duitama et al. (2014) BMC Genomics 15:207). This analysis revealed several putative QTLs linked to acetate ester production in Hybrid A. Next, we plotted the resulting sequencing data (each site that differs between the segregants that were used to make the hybrid are used as 'markers'), and looked where frequency of a certain region was completely shifted towards one of the parents. There were three of those regions that reached 100% frequency in one of the parents: on ChrXIII, on Chr XV and on ChrXIV. Because the pooled segregants (green line) and the random pool (red line) showed the same trend for ChrXIV (FIG. 2), ChrXIV was excluded from further analysis. As such, two main QTLs, i.e. QTL1 on chromosome 13 (ChrXIII:557,000-568,000) (FIG. 3) and QTL2 on chromosome 15 (ChrXV:1,040,000-1,053, 000) (FIG. 4) were selected. QTL1 reached 100% frequency in the Y242 strain, while QTL2 reached 100% in Y354. These QTL's were further analysed using reciprocal hemizygosity analysis (RHA) to pinpoint the causative alleles. However, due to our segregant selection strategy, caution has to be taken when interpreting the results. Indeed, because segregants from Hybrid A were selected (and pooled) for their high level of isoamyl acetate production ((HIGH IA), see Example 2), while we were looking for alleles that reduce the acetate ester production, unravelling the origin of the QTLs is not straightforward. For QTL1, a SNP variant frequency of ~0 was achieved for this DNA region in the segregant pool (see FIG. 3). This means that the pool does not contain any segregants containing the Y354 allele and thus that all selected segregants from Hybrid A possesses the Y242 QTL. Given that Hybrid A segregants were selected for high isoamyl acetate production (Example 2), an allele that reduces acetate ester production should be absent from the pool. Consequently, the allele that we are looking for in QTL1 and that limits acetate ester production originates from Y354. This would mean that although Y354 is a high acetate ester producing strain, it still harbours an inhibitor of acetate ester production, which might be masked by a compensatory mutation. This is in line with the data shown in Table 1: the isoamyl acetate production in the parental Y354 strain is lower than the Y354 segregant. On the other hand, for QTL2, a SNP variant frequency of ~1 was reached (see FIG. 4), meaning that all selected segregants from Hybrid A possessed the Y354 QTL. Given that segregants were selected for high isoamyl acetate production, the allele to be identified and that reduces acetate ester production should be absent from the pool and thus originates from Y242.

Example 4. Pinpointing Causative Alleles within the QTLs Using Reciprocal Hemizygosity Analysis To further narrow down both selected QTLs to a single-gene level and in order to distinguish between phenotype-relevant and phenotype-irrelevant genes within the QTLs, a reciprocal hemizygosity analysis (RHA) was performed for each gene within the QTL. In this strategy, the phenotypic impact of the two parental alleles of the gene under investigation is analyzed in a uniform genetic background, which is the diploid hybrid strain. The major advantage of using this background is that any important interactions between the respective gene and the various parent strain-specific genetic factors contributing to the phenotype are retained. Hence, one mutant carries the allele from Y354 and is deleted for the allele from Y242, while the other mutant carries the allele from Y242 and is deleted for the allele from Y354. By comparing the phenotypes of the two mutants, it will be revealed whether an allele from one genetic background is advantageous over that from the other (for more info, see Steinmetz et al. 2002, Nature 416: 326-330). To knock out the gene of interest in the diploid hybrid strain, first a deletion cassette (containing the kanamycin antibiotic resistance marker) was designed for each gene. The region of homology was designed in such a way, that both alleles in the hybrid were targeted. Then, the diploid hybrid was transformed with the construct, plated on agar medium supplemented with kanamycin, and presence of the cassette in the resulting colonies was assessed using PCR. Next, sequencing of the targeted gene in the positive transformants revealed which of the two alleles was deleted, and which was retained (simultaneous deletion of both alleles is unlikely due to the relatively low transformation efficiency). For each targeted gene, we stored four mutants: two containing only the Y242 allele and two containing only the Y354 allele. All four were tested in the experiments described below. This pipeline was repeated for each gene in both selected QTLs.

Example 5. IMP1, a Novel Regulator of Acetate Ester Production

Figure 5A:
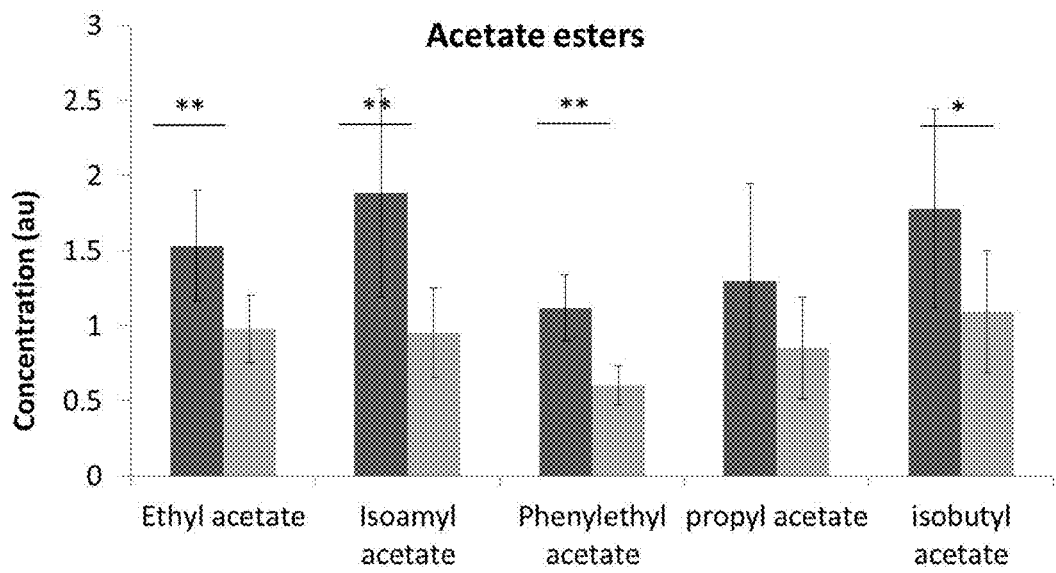
FIGS. 5A and 5B. Production of aromatic acetate esters (FIG. 5A) and alcohols (FIG. B) of the IMP1 RHA mutants. The dark grey bars represent the aroma profile of the RHA mutant containing only the Y242 allele, light grey bars the profile of the RHA mutant containing only the Y354 allele. Acetate ester production (FIG. 5A) differs heavily between the two strains, while no influence on alcohol production (FIG. 5B) (one of the acetate ester precursors) was noticed. Data are normalized to the production of the WT hybrid (consisting of both alleles). *; p-value <0.05 and **; p-value <0.01. These experiments were performed in lab-scale fermentations (see Materials and Methods).
Figure 5B:
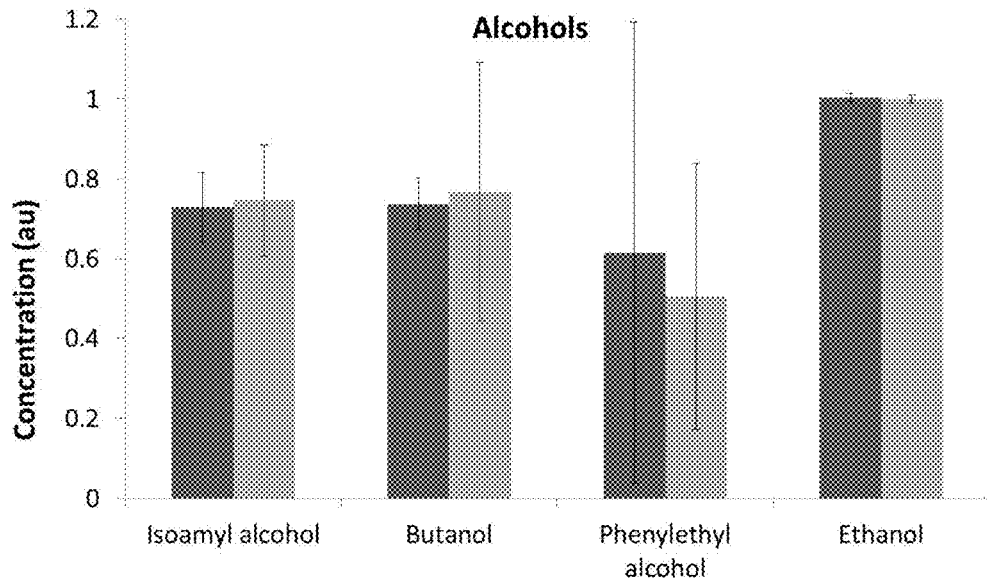

As described above (Example 3), the allele from QTL1 that putatively reduces acetate ester production originates from Y354. For QTL1, the above describe RHA analysis revealed a clear effect for only one gene, namely IMP1 or inner membrane peptidase 1. The data shown in FIG. 5A indicate that the three most industrially relevant acetate esters (isoamyl acetate, ethyl acetate and phenyl ethyl acetate) are significantly reduced in strains harbouring the Y354 IMP1 allele. Also propyl acetate and isobutyl acetate are strongly reduced in strains harbouring the Y354 IMP1 allele. Surprisingly, we show that higher alcohols (the precursors of acetate esters) are not affected (FIG. 5B). Interestingly, the allele also seems to have an effect in a heterozygous state. Indeed, the mutant harbouring only the Y242 IMP1 allele produces more acetate esters compared to Hybrid A (which contains both Y242 and Y354 IMP1 alleles), while production of the mutant harbouring only the Y354 IMP1 allele often shows a similar (or slightly lower) production to Hybrid A. This illustrates the dominant effect of the Y354 IMP1 allele, which has clear advantages for strain design and thus for industrial applicability. Interestingly, the Y354 IMP1 allele caused a reduced acetate ester production while the Y354 strain as well as the hybrid segregants were initially selected for high isoamyl acetate production. Although this is counterintuitive, it is not entirely uncommon. It has previously been shown that alleles can be identified with an opposite phenotype to that for which the parental strain was selected (e.g. Yang et al. 2013 PLoS Genet 9: e1003693). Importantly, we did not detect any differences in ethanol production between the mutant strains (FIG. 5B), indicating that this Y354 IMP1 allele can be introduced in industrial strains without compromising fermentation yield and efficiency.

Example 6. Sequencing of the Identified IMP1 Allele

Upon identifying the Y354 IMP1 allele as inhibitor of acetate ester production in yeast, the allele was sequenced to unravel the nature of the mutation. The sequence of the identified Y354 IMP1 allele is given below and from here on referred to as SEQ ID No. 1. Sequencing revealed an insertion of 2 nucleotides at position 459 and 461 (underlined and highlighted in bold) compared to the wild type (as present in S288c) sequence, causing a frameshift and a premature stop codon (underlined and italics). This mutation leads to the production of a truncated protein of 155 amino acids (AA), instead of 190 AA. The AA sequence of the truncated Imp1 protein is depicted in SEQ ID No. 2.

```
(open reading frame of mutant Imp1 allele)
(Please note that the IMP1 gene is present on the
antisense strand, and that the sequence below is
therefore the reverse compliment).
                                          SEQ ID No. 1
ATGACGGTTGGTACACTTCCCATCTGGTCAAAAACCTTTTCTTATGCAATT

AGGTCATTATGCTTCTTGCATATAATACATATGTATGCATACGAATTTACT

GAGACGAGGGGAGAATCAATGTTGCCAACACTGTCAGCGACCAATGATTAT

GTGCATGTCTTGAAAAATTTCCAAAATGGTAGAGGCATAAAAATGGGTGAC

TGCATAGTAGCACTGAAACCTACTGACCCTAATCATAGGATTTGCAAAAGG

GTTACGGGTATGCCTGGTGATCTCGTGCTCGTGGATCCCAGTACGATAGTT

AATTATGTCGGCGATGTGCTTGTTGATGAGGAGAGGTTTGGTACCTATATT

AAAGTCCCTGAAGGTCATGTTTGGGTAACCGGAGATAATTTGTCACATTCA

TTAGATTCAAGAACATACAATGCATTACCCATGGGGCTGATCATGGGTAAT

GCATTG_TAG_
```

Example 7. The IMP Complex as Regulator for Acetate Ester Production

Figure 6A:
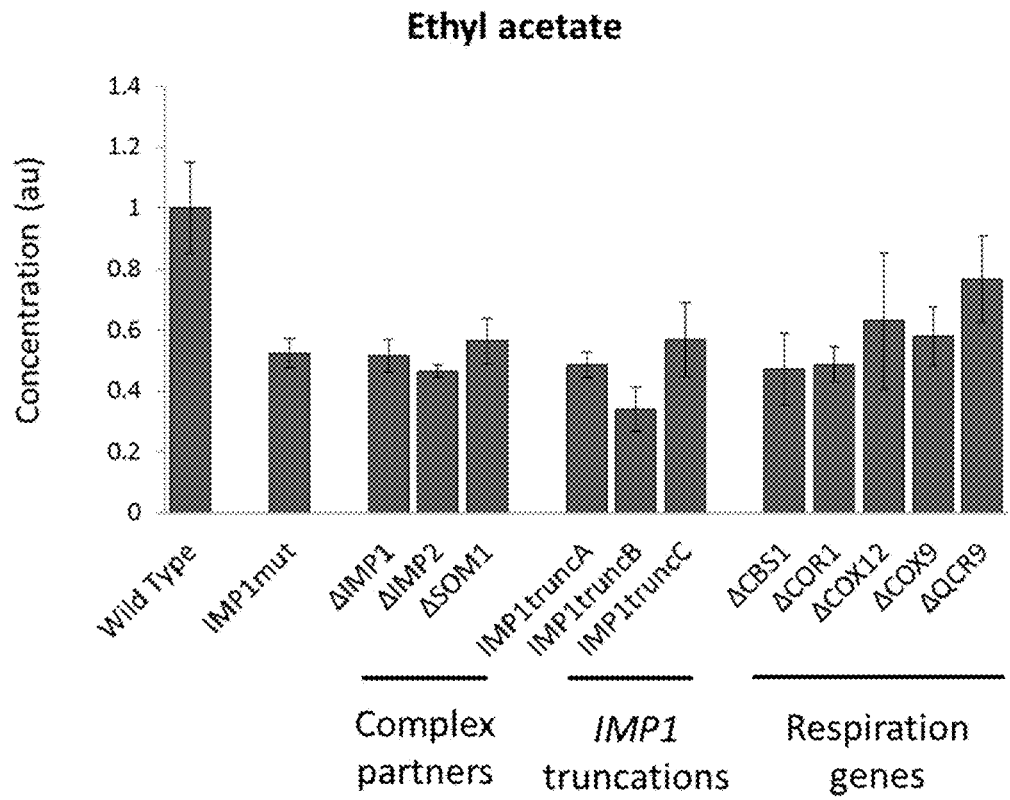
FIGS. 6A and 6B. Ethyl acetate (FIG. 6A) and isoamyl acetate (FIG. 6B) production of the wild type strain, a mutant carrying the identified mutated IMP1 (IMP1mut) allele, mutants with members of the IMP complex knocked out, mutants with truncated IMP1 variants, and mutants in which genes related to respiration are knocked out. The haploid yeast strain BY4742 (derived from the commonly used lab strain S288c) is used as the genetic background. The truncated IMP variants consist of a protein lacking the full C-terminal domain (IMP1truncA; AA 1-148), lacking part of the C-terminal domain (IMP1truncB; AA 1-167) or lacking the transmembrane domain (IMP1-truncC; AA 1-13 fused to AA 32-190). These experiments were performed in mini-scale fermentation (see Materials and Methods).
Figure 6B:
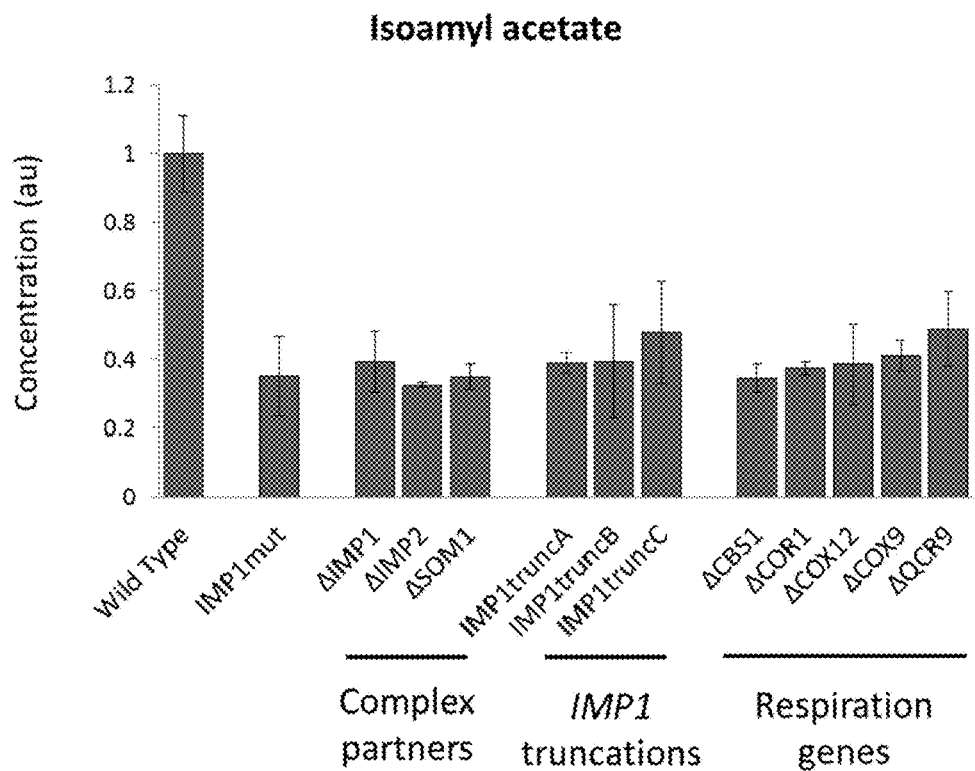

Imp1, the newly identified regulator of acetate ester production in yeast, is a catalytic subunit of the mitochondrial 'Inner Membrane Peptidase' (IMP) complex. The IMP complex processes proteins that are translocated from the mitochondrial matrix into the intermembrane space. Besides Imp1, the IMP complex comprises two other subunits, i.e. Imp2 and Som1. We asked the question whether the reduced acetate production in the IMP1 mutant background was due to a non-functional IMP complex. Therefore, mutants of the haploid yeast strain BY4742 (derived from the commonly used lab strain S288c) were generated in which the genes encoding the other IMP complex subunits (Imp2 and Som1) were deleted were generated and compared to BY4742 expressing the mutant Y354 IMP1 allele (MP/mut) and to BY4742 yeast in which IMP1 was fully deleted. The mutant strains were used to perform fermentation experiments to determine the aroma production. From these experiments several conclusions can be drawn. First, the drastic effect of the identified Y354 IMP1 mutant allele on acetate ester production could be confirmed in another genetic background, more precisely S288c (FIGS. 6A and 6B). Second, the Y354 IMP1 mutant allele has the same effect as a complete deletion of the IMP1 gene (ΔIMP1, FIGS. 6A and 6B). However, the Y354 IMP1 mutant allele has (especially for industrial purposes) a major advantage compared to an IMP1 deletion because the Y354 IMP1 mutant allele surprisingly shows its effect already in a heterozygous state (FIGS. 5A and 5B). Third, deletion of IMP complex subunit IMP2 and SOM1 have a similar effect on ethyl acetate as well as on isoamyl acetate production compared to a full deletion of IMP1 or to expression of the mutant Y354 IMP1 allele (FIGS. 6A and 6B). Fourth, other truncations of the IMP1 gene (IMP1truncA, IMP1truncB, IMP1truncC) have the same effect as the identified allele (FIGS. 6A and 6B). These results demonstrate that acetate ester production depends on a fully functional IMP complex.

Figure 10A:
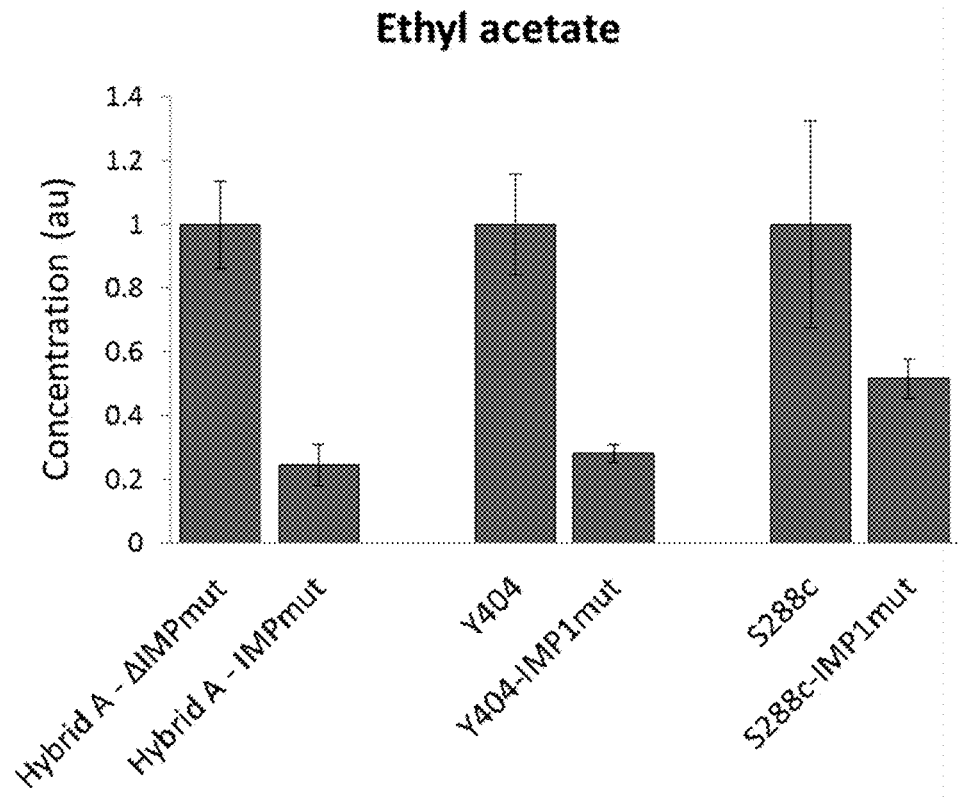
FIGS. 10A and 10B. Production of ethyl acetate (FIG. 10A) and isoamyl acetate (FIG. 10B) of various genetic backgrounds in which IMP1mut was integrated. These data show that the effect of the identified allele is not restricted to a specific genetic background. Interestingly, the effect on severity of ester reduction seems at least slightly strain-dependent, as ethyl acetate reduction (FIG. 10A) was less drastic in the S288c background compared to Hybrid A and Y404. In these examples, IMP1mut was integrated homozygously. These experiments were performed in mini-scale fermentation (see Materials and Methods).
Figure 10B:
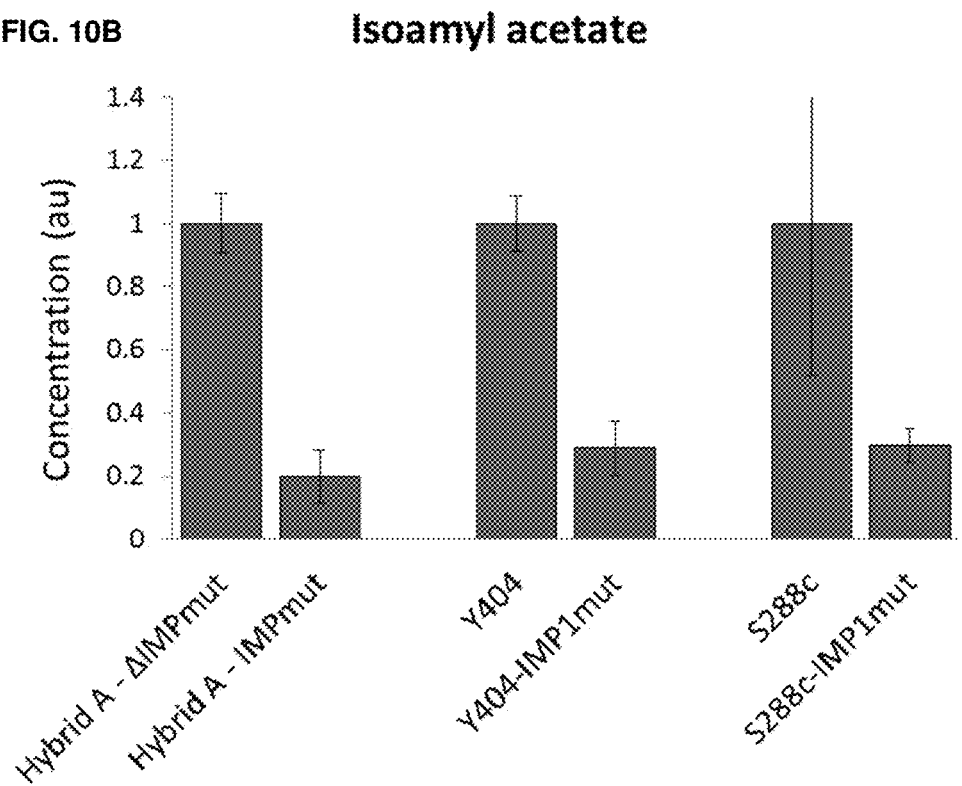

Example 8. Introduction of the Mutant IMP1 Allele in Other Industrial Strains Using CRISPR/Cas To assess the dependency of IMPmut on genetic background of the strain, we are introducing the identified allele in two additional genetically diverse strains, i.e. S288c (the common lab strain) and Y404 (a commercial beer strain) (FIGS. 10A and 10B). In all three genetic backgrounds (Hybrid A, Y404 and S288c), we see a similar effect of the mutant allele. However, the effect for ethyl acetate reductions seems more drastic in Hybrid A and Y404, compared to S288c. Nevertheless, we can conclude that the effect of the identified QTL is not restricted to the genetic background in which the QTL was discovered, which is a phenomenon commonly encountered in QTL studies.

Example 9. Blocking Respiration in Yeast Reduces Acetate Ester Production

Figure 7A:
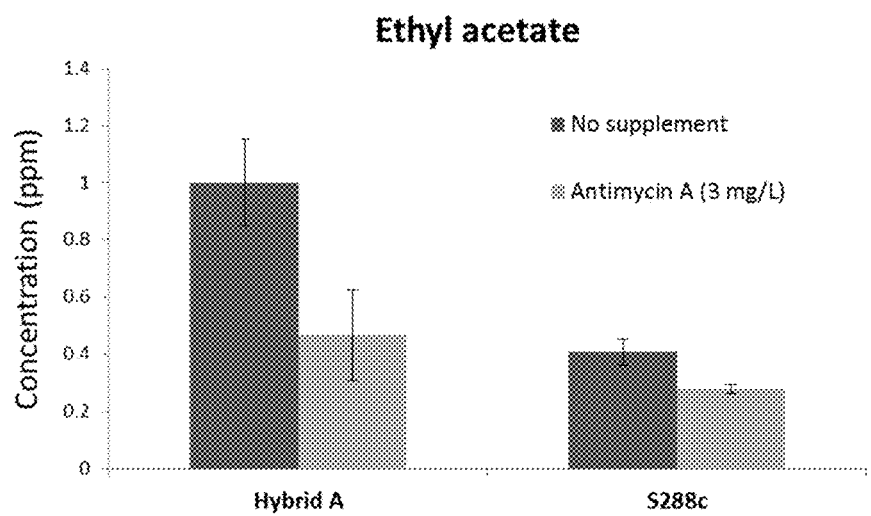
FIGS. 7A and 7B. Ethyl acetate (FIG. 7A) and isoamyl acetate (FIG. 7B) production in yeast in the presence or absence of the respiration blocker antimycin. Data are arbitrary units (au), normalized to the level of production of Hybrid A in the absence of Antimycin A (=1). These experiments were performed in mini-scale fermentation (see Materials and Methods).
Figure 7B:
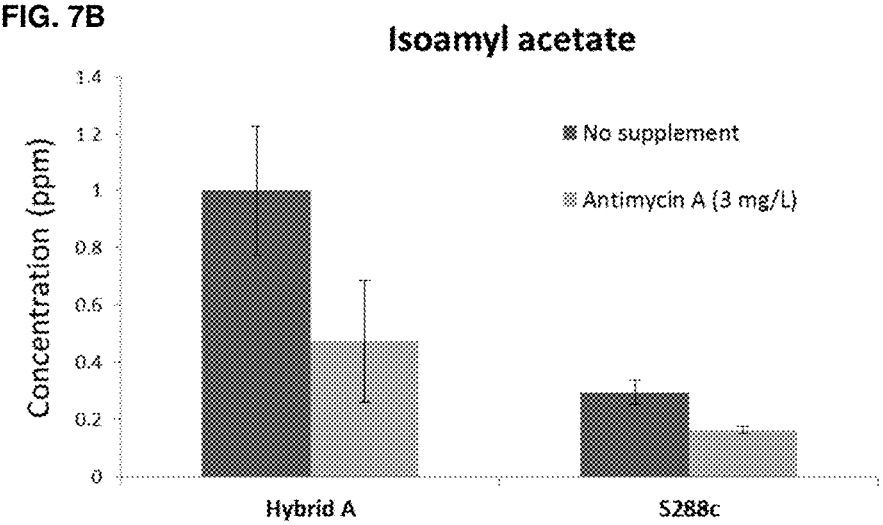

One of the main functions of the IMP complex is processing of subunits of the respiration chain. Given the surprising finding that genetic inference with the IMP complex reduces the production of acetate esters (see Example 5 and 8), we wondered whether respiration in general modulates acetate ester production. First, yeasts strains were developed in which five genes known to be crucial for respiration (i.e. CBS1, COR1, COX9, QCR9 and COX12) were separately deleted and subsequently were used in a fermentation experiment to determine aroma production. All selected genes function independently from the IMP complex. The experiments surprisingly show that absence of respiration in the mutants drastically reduces acetate ester production (FIGS. 6A and 6B). Moreover, acetate ester production in all knock-outs was reduced to the same level observed in IMP1, IMP2 or SOM1 mutants (FIGS. 6A and 6B). Next, we interfered with respiration in yeast in a pharmacological manner and subsequently tested the production of acetate esters. More precisely, an experiment was performed in which acetate ester production of a yeast strain was measured in medium with or without supplementation of 3 mg/L Antimycin A, a chemical compound blocking the respiratory pathway (Kim et al 1999 J Am Chem Soc 121:4902). This experiment revealed a drastic effect of blocking respiration on isoamyl acetate production. When respiration was pharmacologically blocked with antimycin, the isoamyl acetate production dropped about 50% (FIG. 7B). This experiment was done in two genetic backgrounds: S288c and Hybrid A (FIGS. 7A and 7B). Importantly and very surprisingly, the genetic interference with respiration (e.g. with the IMP complex) does not influence alcohol production (FIG. 5B). To summarize, the above results clearly demonstrate that applicant has unraveled a surprising mechanism in which acetate ester production can be reduced during yeast fermentation by blocking respiration. This has been shown using a pharmacologic as well as a genetic approach.

Example 10. Analysis of QTL2 Reveals a Novel Allele of ATF1

Figure 8A:
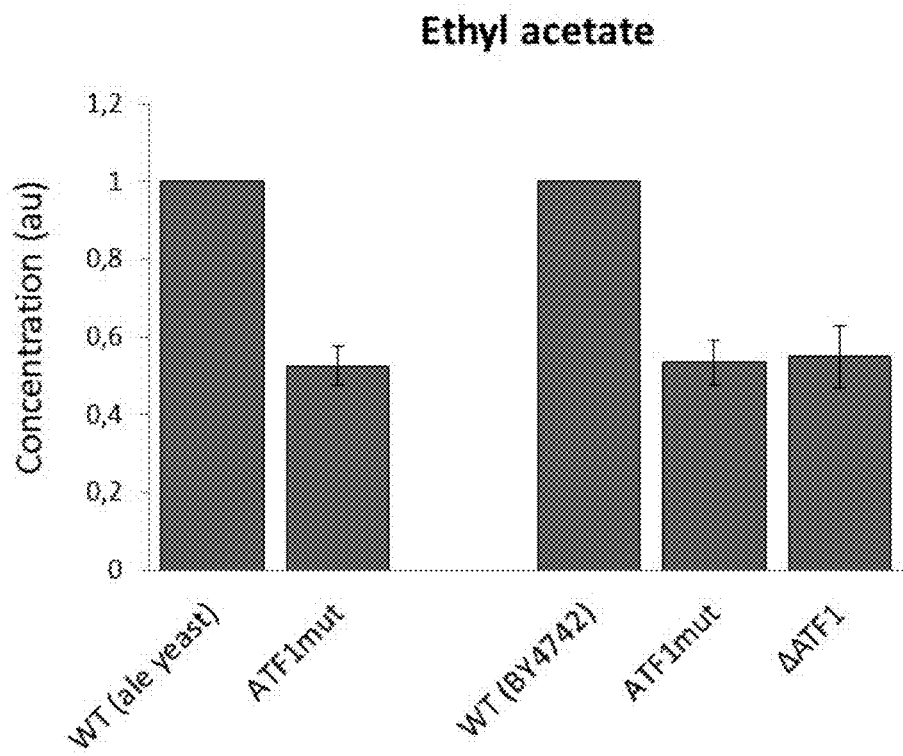
FIGS. 8A and 8B. Production of ethyl acetate (FIG. 8A) and isoamyl acetate (FIG. 8B) of the ATF1 mutant. Ethyl acetate (FIG. 8A) and isoamyl acetate (FIG. 8B) production in a haploid derivative of Y354, a commercial beer strain (ale yeast) and in the haploid strain BY4742 (derived from the commonly used lab strain S288c) possessing a wild-type ATF1 allele (WT) or the newly identified mutant ATF1 allele (ATF1mut). In BY4742, the effect of a full deletion of ATF1 was also analysed as a comparison. These experiments were performed in mini-scale fermentation (see Materials and Methods).
Figure 8B:
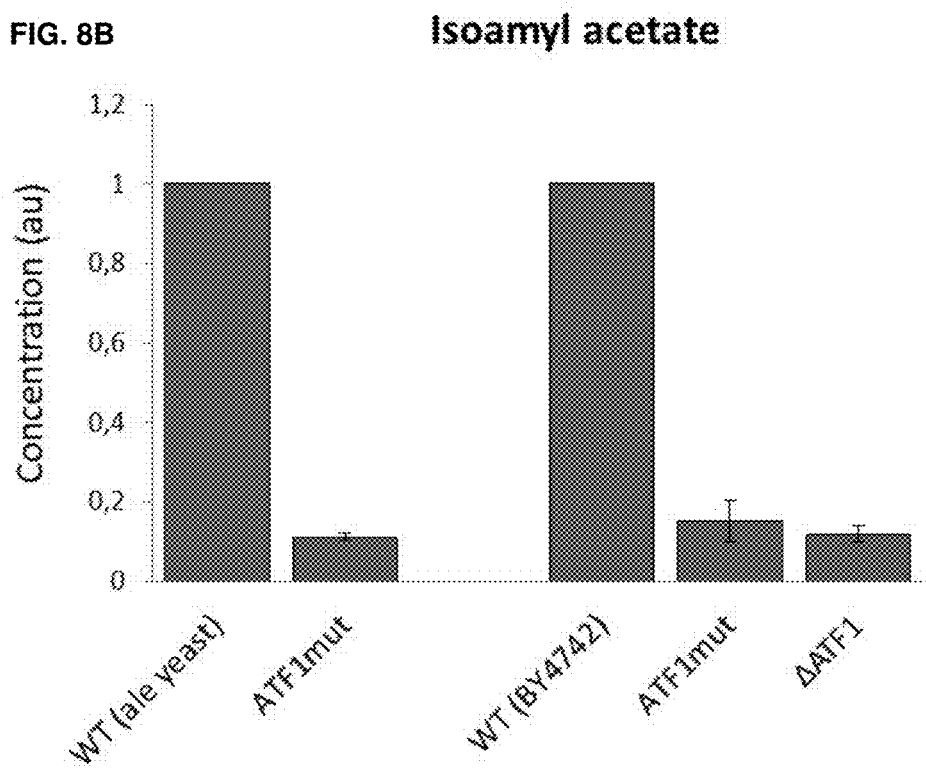
Figure 9A:
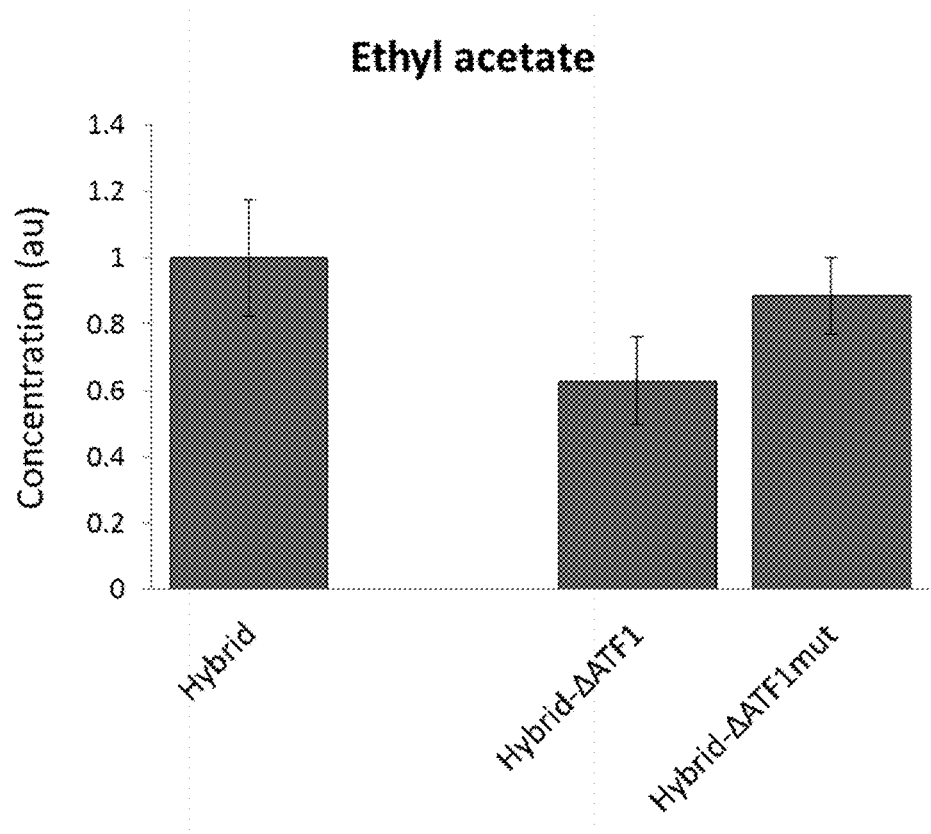
FIGS. 9A and 9B. Production of ethyl acetate (FIG. 9A) and isoamyl acetate (FIG. 9B) of the ATF1 RHA mutants. These experiments confirm that the ATF1 allele present in Y242 is indeed the causative allele in QTL2. Moreover, these data confirm that ATF1 has indeed a more drastic effect on isoamyl (FIG. 9B) compared to ethyl acetate (FIG. 9A). These experiments were performed in mini-scale fermentation (see Materials and Methods).
Figure 9B:
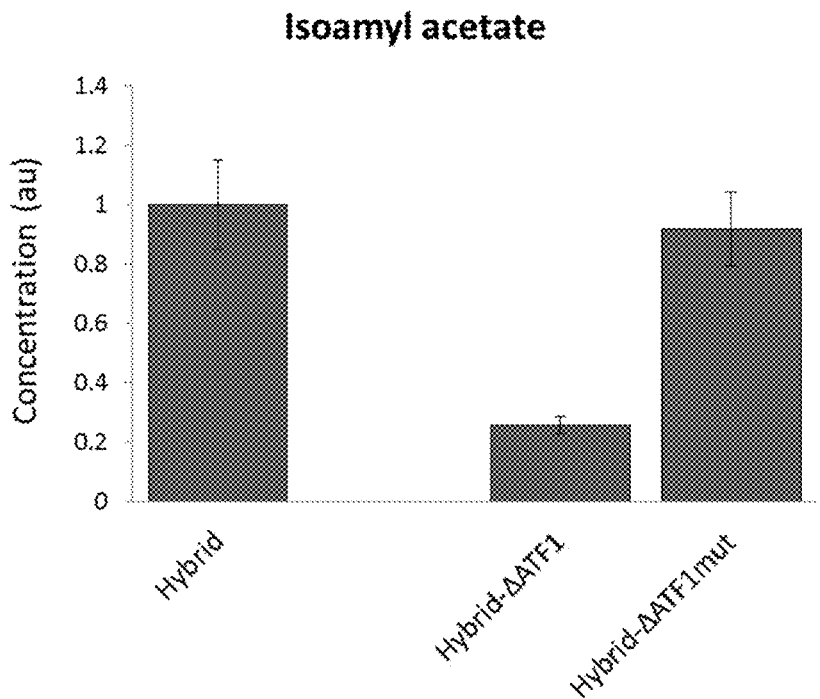

RHA analysis of QTL2 (which originates from Y242, see Example 3) revealed a novel allele of Alcohol 0-acetyltransferase 1 (ATF1) that caused the observed drop in acetate ester production (FIGS. 9A and 9B). ATF1 encodes Alcohol Acetyl Transferase 1 (AATase I; EC 2.3.1.84), which is together with AATase II (encoded by ATF2) the most studied and best characterized enzyme responsible for ester synthesis in yeast (Pires et al. 2014 Appl Microbiol Biotechnol 98:1937-1949). Acetyl-CoA and a fusel alcohol are its substrates, from which it produces acetate esters. Deletion of the ATF1 gene typically results in an 80% reduction in isoamyl acetate production and a 30% decrease for ethyl acetate (Verstrepen et al. 2003 Appl Environ Microbiol 69:5228-5237). This is consistent with the observed drop in acetate esters in our experiments, which points to a complete loss of function of the identified mutant allele (ATF1mut). Although ATF1 is a known acetate ester production gene, naturally occurring ATF1 mutations that are predicted to have an effect on the function of the resulting protein are very rare. The allele identified here and present in QTL2 has a frameshift mutation leading to a premature stop codon very early in the sequence in the Y242 ATF1 allele (from which the region leading to reduced acetate ester production is originating, see Example 3 and FIG. 4). The nucleotide acid sequence of the identified Y242 ATF1 allele is given below and referred to as SEQ ID No. 9. The mutation is a deletion at position 221 (underlined space) causing a frameshift (highlighted in italics) and a premature stop codon (highlighted in italics and underlined). The mutated allele encodes a protein of 114 amino acids instead of 525 amino acids. The effect of the Y242 ATF1 mutation on acetate ester production was determined in the haploid strain BY4742 (derived from the commonly used lab strain S288c) and in a haploid derivative of a commercial beer strain as genetic background. In BY4742, we also compared the Y242 mutant ATF1 allele with a full deletion of the ATF1 gene. These results show that the Y242 ATF1 mutant allele has a similar effect compared to the complete deletion of ATF1 and that the effect of the mutant Y242 ATF1 allele is the same in both genetic backgrounds (FIGS. 8A and 8B).

```
(open reading frame of mutant ATF1 allele)
                                        SEQ ID No. 9
ATGAATGAAATCGATGAGAAAAATCAGGCCCCCGTGCAACAAGAATGCCTG

AAAGAGATGATTCAGAATGGGCATGCTCGGCGTATGGGATCTGTTGAAGAT

CTGTATGTTGCTCTCAACAGACAAAACTTATATCGAAACTTCTGCACATAT
```

-continued
```
GGAGAATTGAGTGATTACTGTACTAGGGATCAGCTCACATTAGCTTTGAAG

GAAATCTGCCTGAAAA_TCCAACTCTTTTACATATTGTTCTACCAACAAGA

TGGCCAAATCATGAAAATTATTATCGCAGTTCCGAATACTATTCACGGCCA

CATCCAGTGCATGATTATATTTCAGTATTACAAGAATTGA
```

Materials and Methods

Yeast Strains and Growth Conditions

In this study, two different hybrids were developed (Table 1). Parental strains were selected based on their acetate ester production profile. Overview of mutants developed and disclosed in the application is given in Table 2 and Table 3.

TABLE 2

Overview of the deletion mutants developed in this study.

| Strain background | Gene deleted |
| --- | --- |
| BY4742 | COX9 |
| BY4742 | COX12 |
| BY4742 | ATF1 |
| BY4742 | IMP2 |
| BY4742 | IMP1 |
| BY4742 | SOM1 |
| BY4742 | QCR9 |
| BY4742 | CBS1 |
| BY4742 | COR1 |
| Hybrid A | The ATF1 allele of Y242 |
| Hybrid A | The ATF1 allele of Y354 |
| Hybrid A | The IMP1 allele of Y242 |
| Hybrid A | The IMP1 allele of Y354 |

All strains were long term stored in −80° C. using a glycerol based standard storage medium (peptone 2% w v$^{-1}$, yeast extract 1% w v$^{-1}$, glucose 2% w v$^{-1}$, glycerol 25% v v$^{-1}$).

TABLE 3

Overview of the other mutants developed in this study.

| Strain background | Modification |
| --- | --- |
| BY4742 | IMP1truncA |
| BY4742 | IMP1truncB |
| BY4742 | IMP1truncC |
| BY4742 | Introduction of IMP1mut |
| BY4742 | Introduction of ATF1mut |
| Y354-18B | Introduction of ATF1mut |
| Y404 | Homozygous Introduction of IMP1mut |
| BY4742 | CBS1 |
| BY4742 | COR1 |

Sporulation, Tetrad Dissection and Mating Type Characterization

Sporulation was induced on acetate medium (1% w v$^{-1}$ potassium acetate, 0.05% w v$^{-1}$ amino acid mix (Adenine 21 mg L$^{-1}$; L-Alanine 86.5 mg L$^{-1}$; L-Arginine HCl 85.6 mg L$^{-1}$; L-Asparagine 85.6 mg L$^{-1}$; L-Aspartic Acid 85.6 mg L$^{-1}$; L-Cysteine HCl 85.6 mg L$^{-1}$; Glutamine 85.6 mg L$^{-1}$; L-Glutamic Acid 85.6 mg L$^{-1}$; Glycine 85.6 mg L$^{-1}$; L-Histidine HCl 85.6 mg L$^{-1}$; Myo-Inositol 85.6 mg L$^{-1}$; L-Isoleucine 85.6 mg L$^{-1}$; L-Leucine 173.4 mg L$^{-1}$; L-Lysine HCl 85.6 mg L$^{-1}$; L-Methionine 85.6 mg L$^{-1}$; Para-Aminobenzoic Acid 8.6 mg L$^{-1}$; L-Phenylalanine 85.6 mg L$^{-1}$; L-Proline 85.6 mg L$^{-1}$; L-Serine 85.6 mg L$^{-1}$; L-Threonine 85.6 mg L$^{-1}$; L-Tryptophan 85.6 mg L$^{-1}$; L-Tyrosine 85.6 mg L$^{-1}$; Uracil 85.6 mg L$^{-1}$; L-Valine 85.6 mg L$^{-1}$), 2% w v$^{-1}$ agar) after 5-10 days at 25° C. The ascus wall was digested with 4 mg mL$^{-1}$ zymolyase (Seikagaku, Tokyo, Japan) suspension (dissolved in 2 M sorbitol), incubated for 3 minutes at room temperature. Tetrads were dissected using a micromanipulator (Singer SMS Manual, Somerset, UK) on YPGlu 2% agar. The hetero- or homothallic nature of the parental strain was determined by mating type testing all viable spores originating from four different tetrads. Mating type was determined by a PCR approach, using MAT-A (5'-ACTCCACTTCAAGTAAGAGTT-3' (SEQ ID NO:29)), MAT-α (5'-GCACGGAATATGGGACTACTTCG-3' (SEQ ID NO:30)) and MAT-R (5'-AGTCACATCAAGATCGTT-TATGG-3' (SEQ ID NO:31)) as primers, and a temperature profile consisting of an initial denaturation step (98° C./2 min), 30 cycles of 98° C./30 s, 55° C./30 s, 72° C./40 s and a final extension of 72° C./5 min.

Flow Cytometry

Segregants selected for the phenotype were first genetically screened to verify that they are clean haploids. The DNA content of yeast was measured by staining of the DNA with propidium iodide (PI) combined with fluorescence-activated cell sorting (FACS). As a reference, S288c haploid (BY4741; ATCC 201388) and diploid (BY4743; ATCC: 201390) strains were used.

Lab-Scale Fermentations in Rich Growth Medium

To assess the production of aroma compounds (acetate esters, ethyl esters and alcohols), lab scale fermentation experiments were performed. These fermentations were performed in rich growth medium (peptone 2% w v$^{-1}$, yeast extract 1% w v$^{-1}$, glucose 10% w v$^{-1}$; YPGlu 10%). Yeast precultures were shaken overnight at 30° C. in test tubes containing 5 mL of yeast extract (1% w v$^{-1}$), peptone (2% w v$^{-1}$) and glucose (4% w v$^{-1}$) medium (YPGlu 4%). After 16 h of growth, 0.5 mL of the preculture was used to inoculate 50 mL of YPGlu 4% medium in 250 mL Erlenmeyer flasks, and this second preculture was shaken at 30° C. for 16 h. This preculture was used for inoculation of the fermentation medium (YPGlu 10%) at an initial optical density (at 600 nm; OD$_{600}$) of 0.5, roughly equivalent to 10' cells mL$^{-1}$. The fermentations, performed in 250 mL Schott bottles with a water lock placed on each bottle, were incubated statically for 7 days at 20° C. Weight loss was measured daily to estimate fermentation progress. After 7 days, the fermentations were stopped, filtered (0.15 mm paper filter) and samples for chromatographic analysis and ethanol measurements were taken. Please note however that high-throughput screening of aroma production of the segregants screened for the QTL analysis was performed differently, see below.

Mini-Scale Fermentations in Rich Growth Medium

Phenotyping of the individual segregants for IA production was performed using an in situ approach, and was conducted as follows: the segregants were streaked from the −80° C. stock on YPGlu 2% agar plates for 48 h at 30° C. Next, a single colony of each segregant was transferred to 80 µL YP. This suspension was mixed, and 50 µL was inoculated in a GC vial (20 mL headspace vials, Agilent) aliquoted with 5 mL YPGlu 4% agar. In case Antimycin A needed to be supplemented, the YPGlu 4% agar was supplemented with 3 mg/L Antimycin A. Dispersion of the inoculum over the full agar surface was ensured. The vials were tightly closed, and incubated at 30° C. After 48 h, the vials were briefly opened to release the build-up $CO_2$. After 96 h, the fermentation was ended, excess $CO_2$ was once again released by brief opening of the vials, and the vials were measured using gas chromatography (see further).

GC Analysis

Headspace gas chromatography coupled with flame ionization detection (HS-GC-FID) (Agilent Technologies, Santa Clara, USA), calibrated for 8 important aroma compounds, was used for the quantification of yeast aroma production (Table 4). The GC was equipped with a headspace autosampler (PAL system, CTC analytics, Zwingen, Switzerland) and contained a DB-WAXETER column (length, 30 m; internal diameter, 0.25 mm; layer thickness, 0.5 µm, Agilent Technologies, Santa Clara, USA) and $N_2$ was used as the carrier gas. Samples were heated for 25 min at 70° C. in the autosampler. The injector block and FID temperatures were both kept constant at 250° C. Samples of 5 mL filtered fermentation medium were collected in 15 mL glass tubes containing 1.75 g of sodium chloride each. These tubes were immediately closed and cooled, to minimize evaporation of volatile compounds. The oven temperature was held at 50° C. for 5 min, after which it increased to 80° C. at 4° C. $min^{-1}$. Next, it increased to 200° C. at 5° C. $min^{-1}$ and held at 200° C. for 3 min. Results were analyzed with the Agilent Chemstation software (Agilent Technologies, Santa Clara, USA).

TABLE 4

Schematic overview of the aroma compounds analyzed.

|  | Flavor description | Threshold (ppm) |
|---|---|---|
| Acetate esters | | |
| Ethyl acetate | Solvent | 30 |
| Isobutyl acetate | Banana, sweet | 1.6 |
| Isoamyl acetate | Banana, pear | 0.51 |
| Phenyl ethyl acetate | Roses, honey | 3.8 |
| Propyl acetate | Pear | NA |
| Higher alcohols | | |
| Isoamyl alcohol | Banana | 70 |
| Butanol | Alcohol | 450 |
| Phenyl ethanol | Roses, flowery | 125 |

The flavor description and reported threshold level are indicated (Meilgaard, 1975).
NA = not available.

Pooled-Segregant Whole-Genome Sequence Analysis and Determination of SNP Variant Frequency Whole-Genome Sequencing For each genetic mapping experiment, the selected segregants were grown separately in 1 mL YPGlu 2% cultures at 30° C. for 16 h. The cell count was measured for each culture separately, and the cultures were pooled based on the same cell count. Genomic DNA of the pooled samples (and parental strains) was extracted using the Qiagen Genomic prep 100G kit (Qiagen, Venlo, Netherlands) and send for sequencing to the VIB Nucleomics Core (Leuven, Belgium). Library preps were done using NEBNext Ultra library prep with Covaris shearing to the desired fragment length. Paired-end short reads of 250 bp were generated using an Illumina MiSeq v2 500. The reads were aligned to *S. cerevisiae* S288c reference sequence (release R41-1-1) using the Burrows-Wheeler Aligner software (BWA, v0.6.1) with default parameters, and the Next Generation Sequencing Eclipse Plugin (NGSEP) tool (Duitama et al., 2014b).

Filtering

Single nucleotide polymorphisms (SNPs) were selected for high quality, based on filtering for sufficient coverage (coverage should be >20 times, both in parental and pool sequences) and a ratio of 90% (as a false positive filter for parental strain sequences). In total, 60,570 and 28,395 informative SNPs and InDels were identified for Hybrid 2 and Hybrid 3, resp.

Statistical Model

For the selection of loci significantly enriched in the selected pool, the Extraction of over-represented alleles in BSA (EXPLoRA) tool was used (Duitama et al., 2014a). This is an algorithm for QTL mapping data analysis in Bulk Segregant Analysis experiments. The algorithm explicitly models the dependency between neighboring marker sites (SNPs) by exploiting the properties of linkage disequilibrium through a Hidden Markov Model. For more information, see Duitama et al. (2014a).

Sequencing of Unselected Pools

In addition to the selected pools, pools of unselected segregants were included in the experiment to detect involuntarily selection of certain phenotypes beneficial in this experimental setup, such as sporulation efficiency, spore viability and general growth speed. Although these random pools cannot be directly implemented in the EXPLoRA algorithm, it was used to manually cure the QTL selection.

RHA Analysis and Development of Knockout Mutants in BY4742

Genomic DNA was extracted in 96-well format, executed in the Tissue lyser ii (QIAGEN, Venlo, Netherlands) following manufacturer's instructions (ether extraction). To amplify DNA fragments, a C1000 Thermal Cycler (Biorad, Hercules, USA) was used, using ExTaq as polymerase. Antibiotic resistance cassette (KanMX) was amplified from a plasmid and targeted to the candidate genes using following primers:

IMP1

(SEQ ID NO: 11)
FW: CCAAATATTGCGTATCGAACCGTCCCAGAAGGGCTTGTCAAAATTGT

TAGCAGCTACAATCTACGCTGCAGGTCGACAA (SEQ ID NO: 12)
RV: GGAGATAATTTGTCACATTCATTAGATTCAAGAACATACAATGCATT

ACCCATGGGGCTGACGTTGGCCGATTCATTAA

ATF1

(SEQ ID NO: 13)
FW: GGACATTGAGCTAAGGTTCAATGCACTCGATGGTCTTCTCACTTCCG

AATATATAGATCTAGCTACGCTGCAGGTCGACAA (SEQ ID NO: 14)
RV: GGACGACGATTCTGACCCTTTCTATTTAAATAGCTCCTTACATCGAG

AAGATCTCTGCAGCCGTTGGCCGATTCATTAA

IMP2

(SEQ ID NO: 15)
FW: TAGCAATTTCATGGGTTCCGGTACTTCTAACAATCAATAATAATGTG

GTCCAGCTGAAGCTTCGTACGC (SEQ ID NO: 16)
RV: GTTGCCAGCGTTTCCGTTTGCGGGTTCAGCGTAGGCTGCATAGAGGT

ACCGTGCTTGGGTGTTTTGAAGTGG

SOM1

(SEQ ID NO: 17)
FW: GTGTCCGTGACCTCGTAGTTAGTGGCTGATTTGTCGGGTGCAATGCA

GTGGTGCTTGGGTGTTTTGAAGTGG (SEQ ID NO: 18)
RV: GGAGTGCCAATTCAAAGGAGCCGAATACGTCTGCTCGCCTTTTAAGA

GGCCAGCTGAAGCTTCGTACGC

Yeast transformations were performed described in Gietz et al. (2001). Checking of the cassette is integrated in the right spot was done by PCR, and identification of the allele that was deleted was done by Sanger sequencing of the PCR product.

CRISPR/Cas to Introduce Identified Mutant Alleles in Other Strains

Using the CRISPR/Cas9 technique, we introduced the two mutant alleles of the application in various other strains. In addition, we used this technology to develop the truncated IMP1 variants (IMP1truncA, IMP1truncB and IMP1truncC). The used CRISPR system is based on the solo CRIPSR' system for genome editing in Candida albicans (Vyas et al. 2015 Science advances 1.3: e1500248). The solo system was later on optimized for the use in S. cerevisiae by transferring the needed CRISPR machinery into a yeast compatible plasmid (pV1382). Based on the obtained sequence information of the IMP1 and ATF1 genes in industrial yeasts (Gallone, Brigida, et al. 2016 Cell 166.6: 1397-1410), we designed a "consensus guide sequence" (a sequence that can be applied in all or most industrial strains), conform to all requirements for the CRISPR system (20 nucleotides long, positioned 5' to a PAM sequence (NGG) and situated within 12 nucleotides of the target area). Below you can find the sequence of the designed guide DNA:

```
                                                (SEQ ID NO: 19)
IMP1:      5'-ATTACCCATGGGGCTGATCA-3'

(SEQ ID NO: 20)
ATF1:      5'-AGAACAATATGTAAAAGAGT-3'

(SEQ ID NO: 21)
IMP1truncA: 5'-CATACAATGCATTACCCATG-3'

(SEQ ID NO: 22)
IMP1truncB: 5'-ACGGTTCGATACGCAATATT-3'

(SEQ ID NO: 23)
IMP1truncC: 5'-AAACCTTTTCTTATGCAATT-3'
```

To create the repair template using the 60 bp oligos with ~20 bp overlap at 3' end, we simply subject them to PCR with no additional template, generating a product of ~100 bp. These products are then purified using the QIAEX II gel extraction kit. The sequence of the repair template can be found below (underlined=location of frame shifts).

```
                                                (SEQ ID NO: 24)
IMP1: 5'-GTATCGAACCGTCCCAGAAGGGCTTGTCAAAATTGTTAGCAG

CTACAATGCATTGCCCATGATCAGCCCCATGGGTAATGCATTGTATGTTCT

TGAATCT-3'

(SEQ ID NO: 25)
ATF1: 5'-CTGTACTAGGGATCAGCTCACATTAGCTTTGAAGGAAATCTG

CCTGAAAATCCAACTCTTTTACATATTGTTCTACCAACAAGATGGCCAAAT

CATGAA-3'

(SEQ ID NO: 26)
IMP1truncA: 5'-CGGAGATAATTTGTCACATTCATTAGATTCAAGAAC

ATACAATGCATTACCCATGTAGCTGATCATGGGCAAGATTGTAGCTGCTAA

CAATTTTGACAAG-3'

(SEQ ID NO: 27)
IMP1truncB: 5'-AAGATTGTAGCTGCTAACAATTTTGACAAGCCCTTC

TGGGACGGTTAGATACGCAATATTTGGGGTTTCAAATGGATCAATAATACA

TTTCTAGATGTGC-3'

(SEQ ID NO: 28)
IMP1truncC: 5'-GTGTACAATACCAGGGATGACGGTTGGTACACTTCC

CATCTGGTCAAAAACCTTTGAATTTACTGAGACGAGGGGAGAATCAATGTT

GCCAACACTGTCA-3'
```

For more details on the cloning and transformation protocol, see Vyas et al. (2015 Science advances 1.3: e1500248).

The invention claimed is:

1. A method of producing a fermented solution with a reduced level of at least one acetate ester, the method comprising:
    determining that a yeast comprises a disrupted, partially deleted, or completely deleted subunit of the inner membrane peptidase (IMP) complex, wherein the disrupted, partially deleted, or completely deleted subunit of the IMP complex has reduced activity as compared to a corresponding subunit of the IMP complex that is not disrupted, partially deleted, or completely deleted;
    adding the yeast comprising the disrupted, partially deleted, or completely deleted IMP subunit to a fermentation medium comprising glucose;
    fermenting the fermentation medium to produce the fermented solution; and
    measuring, in the fermented solution, a statistically significant reduction in the level of the at least one acetate ester as compared to a fermented solution obtained by fermentation under the same conditions using a yeast comprising the corresponding subunit of the IMP complex that is not disrupted, partially deleted or completely deleted.

2. The method according to claim 1, wherein the at least one acetate ester is selected from the group consisting of isoamyl acetate, ethyl acetate, phenylethyl acetate, propyl acetate, and isobutyl acetate.

3. The method according to claim 1, wherein the yeast further comprises one or more mutant alleles limiting acetate ester production.

4. The method according to claim 3, wherein the one or more mutant alleles limiting acetate ester production disrupts, partially deletes, or completely deletes AFTI, AFT2, IMP1, IMP2, SOM1, CBS1, COR1, QCR9, COX9 or COX12.

5. The method according to claim 1, wherein the disrupted, partially deleted, or completely deleted subunit of the IMP complex is a truncated Imp1 protein lacking residues 14-31 or 147-190 of a wild-type full length yeast Imp1 protein of SEQ ID NO: 4.

6. The method according to claim 1, wherein the disrupted, partially deleted, or completely deleted subunit of the IMP complex is a truncated Imp1 protein selected from the group consisting of SEQ ID NO: 2, SEQ ID NO: 6, SEQ ID NO: 7, and SEQ ID NO: 8.

7. The method according to claim 1, wherein the yeast comprising the corresponding subunit of the IMP complex that is not disrupted, partially deleted or completely deleted is yeast strain S228c or Y404.

8. A method of producing a fermented solution with a reduced level of at least one acetate ester, the method comprising:
    determining that a yeast comprises a disrupted, partially deleted, or completely deleted subunit of the inner membrane peptidase (IMP) complex, wherein the disrupted, partially deleted, or completely deleted subunit of the IMP complex has reduced activity as compared to a corresponding subunit of the IMP complex that is not disrupted, partially deleted, or completely deleted;
    adding the yeast comprising the disrupted, partially deleted, or completely deleted IMP subunit to a fermentation medium comprising glucose;
    fermenting the fermentation medium to produce the fermented solution; and
    measuring, in the fermented solution, the level of the at least one acetate ester, wherein the level of the at least one acetate ester is statistically significantly reduced as compared to a fermented solution obtained by fermentation under the same conditions using *S. cerevisiae* strain Y354, S228c or Y404.

9. The method according to claim 1, wherein the disrupted, partially deleted, or completely deleted subunit of the IMP complex is IMP1 IMP2, or SOM1.

* * * * *

SEQUENCE LISTING

<160> NUMBER OF SEQ ID NOS: 31

<210> SEQ ID NO 1
<211> LENGTH: 468
<212> TYPE: DNA
<213> ORGANISM: Saccharomyces cerevisiae

<400> SEQUENCE: 1

```
atgacggttg gtacacttcc catctggtca aaaacctttt cttatgcaat taggtcatta      60
tgcttcttgc atataataca tatgtatgca tacgaattta ctgagacgag gggagaatca     120
atgttgccaa cactgtcagc gaccaatgat tatgtgcatg tcttgaaaaa tttccaaaat     180
ggtagaggca taaaatggg tgactgcata gtagcactga aacctactga ccctaatcat      240
aggatttgca aaagggttac gggtatgcct ggtgatctcg tgctcgtgga tcccagtacg     300
atagttaatt atgtcggcga tgtgcttgtt gatgaggaga ggtttggtac ctatattaaa     360
gtccctgaag gtcatgtttg ggtaaccgga gataatttgt cacattcatt agattcaaga     420
acatacaatg cattacccat ggggctgatc atgggtaatg cattgtag                  468
```

<210> SEQ ID NO 2
<211> LENGTH: 155

<212> TYPE: PRT
<213> ORGANISM: Saccharomyces cerevisiae

<400> SEQUENCE: 2

```
Met Thr Val Gly Thr Leu Pro Ile Trp Ser Lys Thr Phe Ser Tyr Ala
1               5                   10                  15

Ile Arg Ser Leu Cys Phe Leu His Ile His Met Tyr Ala Tyr Glu
            20                  25                  30

Phe Thr Glu Thr Arg Gly Glu Ser Met Leu Pro Thr Leu Ser Ala Thr
            35                  40                  45

Asn Asp Tyr Val His Val Leu Lys Asn Phe Gln Asn Gly Arg Gly Ile
        50                  55                  60

Lys Met Gly Asp Cys Ile Val Ala Leu Lys Pro Thr Asp Pro Asn His
65                  70                  75                  80

Arg Ile Cys Lys Arg Val Thr Gly Met Pro Gly Asp Leu Val Leu Val
                85                  90                  95

Asp Pro Ser Thr Ile Val Asn Tyr Val Gly Asp Val Leu Val Asp Glu
            100                 105                 110

Glu Arg Phe Gly Thr Tyr Ile Lys Val Pro Glu Gly His Val Trp Val
            115                 120                 125

Thr Gly Asp Asn Leu Ser His Ser Leu Asp Ser Arg Thr Tyr Asn Ala
        130                 135                 140

Leu Pro Met Gly Leu Ile Met Gly Asn Ala Leu
145                 150                 155
```

<210> SEQ ID NO 3
<211> LENGTH: 573
<212> TYPE: DNA
<213> ORGANISM: Saccharomyces cerevisiae

<400> SEQUENCE: 3

```
atgacggttg gtacacttcc catctggtca aaaacctttt cttatgcaat taggtcatta      60
tgcttcttgc atataataca tatgtatgca tacgaattta ctgagacgag gggagaatca     120
atgttgccaa cactgtcagc gaccaatgat tatgtgcatg tcttgaaaaa tttccaaaat     180
ggtagaggca taaaaatggg tgactgcata gtagcactga aacctactga ccctaatcat     240
aggatttgca aagggttac gggtatgcct ggtgatctcg tgctcgtgga tcccagtacg     300
atagttaatt atgtcggcga tgtgcttgtt gatgaggaga ggtttggtac ctatattaaa     360
gtccctgaag tcatgtttg ggtaaccgga gataatttgt cacattcatt agattcaaga     420
acatacaatg cattacccat ggggctgatc atgggtaaga ttgtagctgc taacaatttt     480
gacaagccct tctgggacgg ttcgatacgc aatatttggg gtttcaaatg gatcaataat     540
acatttctag atgtgcaggc taagagcaac tga                                 573
```

<210> SEQ ID NO 4
<211> LENGTH: 190
<212> TYPE: PRT
<213> ORGANISM: Saccharomyces cerevisiae

<400> SEQUENCE: 4

```
Met Thr Val Gly Thr Leu Pro Ile Trp Ser Lys Thr Phe Ser Tyr Ala
1               5                   10                  15

Ile Arg Ser Leu Cys Phe Leu His Ile His Met Tyr Ala Tyr Glu
            20                  25                  30

Phe Thr Glu Thr Arg Gly Glu Ser Met Leu Pro Thr Leu Ser Ala Thr
            35                  40                  45
```

```
Asn Asp Tyr Val His Val Leu Lys Asn Phe Gln Asn Gly Arg Gly Ile
    50                  55                  60

Lys Met Gly Asp Cys Ile Val Ala Leu Lys Pro Thr Asp Pro Asn His
65                  70                  75                  80

Arg Ile Cys Lys Arg Val Thr Gly Met Pro Gly Asp Leu Val Leu Val
                85                  90                  95

Asp Pro Ser Thr Ile Val Asn Tyr Val Gly Asp Val Leu Val Asp Glu
            100                 105                 110

Glu Arg Phe Gly Thr Tyr Ile Lys Val Pro Glu Gly His Val Trp Val
        115                 120                 125

Thr Gly Asp Asn Leu Ser His Ser Leu Asp Ser Arg Thr Tyr Asn Ala
    130                 135                 140

Leu Pro Met Gly Leu Ile Met Gly Lys Ile Val Ala Ala Asn Asn Phe
145                 150                 155                 160

Asp Lys Pro Phe Trp Asp Gly Ser Ile Arg Asn Ile Trp Gly Phe Lys
                165                 170                 175

Trp Ile Asn Asn Thr Phe Leu Asp Val Gln Ala Lys Ser Asn
                180                 185                 190

<210> SEQ ID NO 5
<211> LENGTH: 147
<212> TYPE: PRT
<213> ORGANISM: Saccharomyces cerevisiae

<400> SEQUENCE: 5

Met Thr Val Gly Thr Leu Pro Ile Trp Ser Lys Thr Phe Ser Tyr Ala
1               5                   10                  15

Ile Arg Ser Leu Cys Phe Leu His Ile Ile His Met Tyr Ala Tyr Glu
                20                  25                  30

Phe Thr Glu Thr Arg Gly Glu Ser Met Leu Pro Thr Leu Ser Ala Thr
            35                  40                  45

Asn Asp Tyr Val His Val Leu Lys Asn Phe Gln Asn Gly Arg Gly Ile
    50                  55                  60

Lys Met Gly Asp Cys Ile Val Ala Leu Lys Pro Thr Asp Pro Asn His
65                  70                  75                  80

Arg Ile Cys Lys Arg Val Thr Gly Met Pro Gly Asp Leu Val Leu Val
                85                  90                  95

Asp Pro Ser Thr Ile Val Asn Tyr Val Gly Asp Val Leu Val Asp Glu
            100                 105                 110

Glu Arg Phe Gly Thr Tyr Ile Lys Val Pro Glu Gly His Val Trp Val
        115                 120                 125

Thr Gly Asp Asn Leu Ser His Ser Leu Asp Ser Arg Thr Tyr Asn Ala
    130                 135                 140

Leu Pro Met
145

<210> SEQ ID NO 6
<211> LENGTH: 147
<212> TYPE: PRT
<213> ORGANISM: Saccharomyces cerevisiae

<400> SEQUENCE: 6

Met Thr Val Gly Thr Leu Pro Ile Trp Ser Lys Thr Phe Ser Tyr Ala
1               5                   10                  15

Ile Arg Ser Leu Cys Phe Leu His Ile Ile His Met Tyr Ala Tyr Glu
                20                  25                  30
```

```
Phe Thr Glu Thr Arg Gly Glu Ser Met Leu Pro Thr Leu Ser Ala Thr
            35                  40                  45

Asn Asp Tyr Val His Val Leu Lys Asn Phe Gln Asn Gly Arg Gly Ile
 50                  55                  60

Lys Met Gly Asp Cys Ile Val Ala Leu Lys Pro Thr Asp Pro Asn His
 65                  70                  75                  80

Arg Ile Cys Lys Arg Val Thr Gly Met Pro Gly Asp Leu Val Leu Val
                85                  90                  95

Asp Pro Ser Thr Ile Val Asn Tyr Val Gly Asp Val Leu Val Asp Glu
               100                 105                 110

Glu Arg Phe Gly Thr Tyr Ile Lys Val Pro Glu Gly His Val Trp Val
               115                 120                 125

Thr Gly Asp Asn Leu Ser His Ser Leu Asp Ser Arg Thr Tyr Asn Ala
               130                 135                 140

Leu Pro Met
145

<210> SEQ ID NO 7
<211> LENGTH: 167
<212> TYPE: PRT
<213> ORGANISM: Saccharomyces cerevisiae

<400> SEQUENCE: 7

Met Thr Val Gly Thr Leu Pro Ile Trp Ser Lys Thr Phe Ser Tyr Ala
 1               5                  10                  15

Ile Arg Ser Leu Cys Phe Leu His Ile Ile His Met Tyr Ala Tyr Glu
                20                  25                  30

Phe Thr Glu Thr Arg Gly Glu Ser Met Leu Pro Thr Leu Ser Ala Thr
            35                  40                  45

Asn Asp Tyr Val His Val Leu Lys Asn Phe Gln Asn Gly Arg Gly Ile
 50                  55                  60

Lys Met Gly Asp Cys Ile Val Ala Leu Lys Pro Thr Asp Pro Asn His
 65                  70                  75                  80

Arg Ile Cys Lys Arg Val Thr Gly Met Pro Gly Asp Leu Val Leu Val
                85                  90                  95

Asp Pro Ser Thr Ile Val Asn Tyr Val Gly Asp Val Leu Val Asp Glu
               100                 105                 110

Glu Arg Phe Gly Thr Tyr Ile Lys Val Pro Glu Gly His Val Trp Val
               115                 120                 125

Thr Gly Asp Asn Leu Ser His Ser Leu Asp Ser Arg Thr Tyr Asn Ala
               130                 135                 140

Leu Pro Met Gly Leu Ile Met Gly Lys Ile Val Ala Ala Asn Asn Phe
145                 150                 155                 160

Asp Lys Pro Phe Trp Asp Gly
                165

<210> SEQ ID NO 8
<211> LENGTH: 172
<212> TYPE: PRT
<213> ORGANISM: Saccharomyces cerevisiae

<400> SEQUENCE: 8

Met Thr Val Gly Thr Leu Pro Ile Trp Ser Lys Thr Phe Glu Phe Thr
 1               5                  10                  15

Glu Thr Arg Gly Glu Ser Met Leu Pro Thr Leu Ser Ala Thr Asn Asp
                20                  25                  30
```

```
Tyr Val His Val Leu Lys Asn Phe Gln Asn Gly Arg Gly Ile Lys Met
         35                  40                  45

Gly Asp Cys Ile Val Ala Leu Lys Pro Thr Asp Pro Asn His Arg Ile
 50                  55                  60

Cys Lys Arg Val Thr Gly Met Pro Gly Asp Leu Val Leu Val Asp Pro
 65                  70                  75                  80

Ser Thr Ile Val Asn Tyr Val Gly Asp Val Leu Val Asp Glu Glu Arg
                 85                  90                  95

Phe Gly Thr Tyr Ile Lys Val Pro Glu Gly His Val Trp Val Thr Gly
             100                 105                 110

Asp Asn Leu Ser His Ser Leu Asp Ser Arg Thr Tyr Asn Ala Leu Pro
         115                 120                 125

Met Gly Leu Ile Met Gly Lys Ile Val Ala Ala Asn Asn Phe Asp Lys
130                 135                 140

Pro Phe Trp Asp Gly Ser Ile Arg Asn Ile Trp Gly Phe Lys Trp Ile
145                 150                 155                 160

Asn Asn Thr Phe Leu Asp Val Gln Ala Lys Ser Asn
                 165                 170
```

```
<210> SEQ ID NO 9
<211> LENGTH: 345
<212> TYPE: DNA
<213> ORGANISM: Saccharomyces cerevisiae

<400> SEQUENCE: 9
atgaatgaaa tcgatgagaa aaatcaggcc cccgtgcaac aagaatgcct gaaagagatg      60
attcagaatg ggcatgctcg gcgtatggga tctgttgaag atctgtatgt tgctctcaac     120
agacaaaact tatatcgaaa cttctgcaca tatggagaat tgagtgatta ctgtactagg     180
gatcagctca cattagcttt gaaggaaatc tgcctgaaaa tccaactctt ttacatattg     240
ttctaccaac aagatggcca atcatgaaa attattatcg cagttccgaa tactattcac     300
ggccacatcc agtgcatgat tatatttcag tattacaaga attga                     345

<210> SEQ ID NO 10
<211> LENGTH: 1577
<212> TYPE: DNA
<213> ORGANISM: Saccharomyces cerevisiae

<400> SEQUENCE: 10
atgaatgaaa tcgatgagaa aaatcaggcc cccgtgcaac aagaatgcct gaaagagatg      60
attcagaatg ggcatgctcg gcgtatggga tctgttgaag atctgtatgt tgctctcaac     120
agacaaaact tatatcgaaa cttctgcaca tatggagaat tgagtgatta ctgtactagg     180
gatcagctca cattagcttt gaaggaaatc tgcctgaaaa tccaactctt ttacatattg     240
ttctaccaac aagatggcca atcatgaaa attattatcg cagttccgaa tactattcac     300
ggccacatcc agtgcatgat tatatttcag tattacaaga attgaaactg agtggtgtgg     360
ttctcaatga acaacctgag tacagtgcag taatgaagca atattagaa gaattcaaaa     420 atagtaaggg ttcctatact gcaaaaattt ttaaacttac taccactttg actattcctt     480
actttggacc aacaggaccg agttggcggc taatttgtct tccagaagag cacacagaaa     540
agtggaaaaa atttatcttt gtatctaatc attgcatgtc tgatggtcgg tcttcgatcc     600
acttttttca tgattaaga gacgaattaa ataatattaa aactccacca aaaaaattag     660
attacatttt caagtacgag gaggattacc aattattgag gaaacttcca gaaccgatcg     720
```

-continued

```
aaaaggtgat agactttaga ccaccgtact tgtttattcc gaagtcactt ctttcgggtt      780
tcatctacaa tcatttgaga ttttcttcaa aaggtgtctg tatgagaatg gatgatgtgg      840
aaaaaaccga tgatgttgtc accgagatca tcaatatttc accaacagaa tttcaagcga      900
ttaaagcaaa tattaaatca aatatccaag gtaagtgtac tatcactccg tttttacatg      960
tttgttggtt tgtatctctt cataaatggg gtaaatttt caaaccattg aacttcgaat      1020
ggcttacgga tatttttatc cccgcagatt gccgctcaca actaccagat gatgatgaaa     1080
tgagacagat gtacagatat ggcgctaacg ttggatttat tgacttcacc ccctggataa     1140
gcgaatttga catgaatgat aacaaagaaa attttggcc acttattgag cactaccatg      1200
aagtaatttc ggaagcttta agaaataaaa agcatctcca tggcttaggg ttcaatatac     1260
aaggcttcgt tcaaaaatat gtgaacattg acaaggtaat gtgcgatcgt gccatcggga    1320
aaagacgcgg aggtacattg ttaagcaatg taggtctgtt taatcagtta gaggagcccg    1380
atgccaaata ttctatatgc gatttggcat ttggccaatt tcaaggatcc tggcaccaag    1440
cattttcctt gggtgtttgt tcgactaatg taaaggggat gaatattgtt gttgcttcaa    1500
caaagaatgt tgttggtagt caagaatctc tcgaagagct ttgctccatt tacaaagctc    1560
tccttttagg cccttag                                                   1577
```

```
<210> SEQ ID NO 11
<211> LENGTH: 79
<212> TYPE: DNA
<213> ORGANISM: Artificial Sequence
<220> FEATURE:
<223> OTHER INFORMATION: IMP1 FW primer

<400> SEQUENCE: 11
ccaaatattg cgtatcgaac cgtcccagaa gggcttgtca aaattgttag cagctacaat      60
ctacgctgca ggtcgacaa                                                  79
```

```
<210> SEQ ID NO 12
<211> LENGTH: 79
<212> TYPE: DNA
<213> ORGANISM: Artificial Sequence
<220> FEATURE:
<223> OTHER INFORMATION: IMP1 RV primer

<400> SEQUENCE: 12
ggagataatt tgtcacattc attagattca agaacataca atgcattacc catggggctg      60
acgttggccg attcattaa                                                  79
```

```
<210> SEQ ID NO 13
<211> LENGTH: 81
<212> TYPE: DNA
<213> ORGANISM: Artificial Sequence
<220> FEATURE:
<223> OTHER INFORMATION: ATF1 FW primer

<400> SEQUENCE: 13
ggacattgag ctaaggttca atgcactcga tggtcttctc acttccgaat atatagatct      60
agctacgctg caggtcgaca a                                               81
```

```
<210> SEQ ID NO 14
<211> LENGTH: 79
<212> TYPE: DNA
<213> ORGANISM: Artificial Sequence
<220> FEATURE:
```

<223> OTHER INFORMATION: ATF1 RV primer

<400> SEQUENCE: 14
ggacgacgat tctgaccctt tctatttaaa tagctcctta catcgagaag atctctgcag    60
ccgttggccg attcattaa                                                 79

<210> SEQ ID NO 15
<211> LENGTH: 69
<212> TYPE: DNA
<213> ORGANISM: Artificial Sequence
<220> FEATURE:
<223> OTHER INFORMATION: IMP2 FW primer

<400> SEQUENCE: 15
tagcaatttc atgggttccg gtacttctaa caatcaataa taatgtggtc cagctgaagc    60
ttcgtacgc                                                            69

<210> SEQ ID NO 16
<211> LENGTH: 72
<212> TYPE: DNA
<213> ORGANISM: Artificial Sequence
<220> FEATURE:
<223> OTHER INFORMATION: IMP2 RV primer

<400> SEQUENCE: 16
gttgccagcg tttccgtttg cgggttcagc gtaggctgca tagaggtacc gtgcttgggt    60
gttttgaagt gg                                                        72

<210> SEQ ID NO 17
<211> LENGTH: 72
<212> TYPE: DNA
<213> ORGANISM: Artificial Sequence
<220> FEATURE:
<223> OTHER INFORMATION: SOM1 FW primer

<400> SEQUENCE: 17
gtgtccgtga cctcgtagtt agtggctgat tgtcgggtg caatgcagtg gtgcttgggt    60
gttttgaagt gg                                                        72

<210> SEQ ID NO 18
<211> LENGTH: 69
<212> TYPE: DNA
<213> ORGANISM: Artificial Sequence
<220> FEATURE:
<223> OTHER INFORMATION: SOM1 RV primer

<400> SEQUENCE: 18
ggagtgccaa ttcaaaggag ccgaatacgt ctgctcgcct tttaagaggc cagctgaagc    60
ttcgtacgc                                                            69

<210> SEQ ID NO 19
<211> LENGTH: 20
<212> TYPE: DNA
<213> ORGANISM: Artificial Sequence
<220> FEATURE:
<223> OTHER INFORMATION: IMP1 gDNA

<400> SEQUENCE: 19
attacccatg gggctgatca                                                20

<210> SEQ ID NO 20
<211> LENGTH: 20

```
<212> TYPE: DNA
<213> ORGANISM: Artificial Sequence
<220> FEATURE:
<223> OTHER INFORMATION: ATF1 gDNA

<400> SEQUENCE: 20
agaacaatat gtaaaagagt                                              20

<210> SEQ ID NO 21
<211> LENGTH: 20
<212> TYPE: DNA
<213> ORGANISM: Artificial Sequence
<220> FEATURE:
<223> OTHER INFORMATION: IMP1truncA gDNA

<400> SEQUENCE: 21
catacaatgc attacccatg                                              20

<210> SEQ ID NO 22
<211> LENGTH: 20
<212> TYPE: DNA
<213> ORGANISM: Artificial Sequence
<220> FEATURE:
<223> OTHER INFORMATION: IMP1truncB gDNA

<400> SEQUENCE: 22
acggttcgat acgcaatatt                                              20

<210> SEQ ID NO 23
<211> LENGTH: 20
<212> TYPE: DNA
<213> ORGANISM: Artificial Sequence
<220> FEATURE:
<223> OTHER INFORMATION: IMP1truncC gDNA

<400> SEQUENCE: 23 aaacctttc ttatgcaatt                                               20

<210> SEQ ID NO 24
<211> LENGTH: 100
<212> TYPE: DNA
<213> ORGANISM: Artificial Sequence
<220> FEATURE:
<223> OTHER INFORMATION: IMP1 repair template

<400> SEQUENCE: 24
gtatcgaacc gtcccagaag ggcttgtcaa aattgttagc agctacaatg cattgcccat    60
gatcagcccc atgggtaatg cattgtatgt tcttgaatct                         100

<210> SEQ ID NO 25
<211> LENGTH: 99
<212> TYPE: DNA
<213> ORGANISM: Artificial Sequence
<220> FEATURE:
<223> OTHER INFORMATION: ATF1 repair template

<400> SEQUENCE: 25
ctgtactagg gatcagctca cattagcttt gaaggaaatc tgcctgaaaa tccaactctt    60
ttacatattg ttctaccaac aagatggcca aatcatgaa                          99

<210> SEQ ID NO 26
<211> LENGTH: 100
<212> TYPE: DNA
<213> ORGANISM: Artificial Sequence
<220> FEATURE:
```

```
<223> OTHER INFORMATION: IMP1truncA repair template

<400> SEQUENCE: 26
cggagataat tgtcacatt cattagattc aagaacatac aatgcattac ccatgtagct    60
gatcatgggc aagattgtag ctgctaacaa ttttgacaag                          100

<210> SEQ ID NO 27
<211> LENGTH: 100
<212> TYPE: DNA
<213> ORGANISM: Artificial Sequence
<220> FEATURE:
<223> OTHER INFORMATION: IMP1truncB repair template

<400> SEQUENCE: 27
aagattgtag ctgctaacaa ttttgacaag cccttctggg acggttagat acgcaatatt    60
tggggtttca aatggatcaa taatacattt ctagatgtgc                          100

<210> SEQ ID NO 28
<211> LENGTH: 100
<212> TYPE: DNA
<213> ORGANISM: Artificial Sequence
<220> FEATURE:
<223> OTHER INFORMATION: IMP1truncC repair template

<400> SEQUENCE: 28
gtgtacaata ccagggatga cggttggtac acttcccatc tggtcaaaaa cctttgaatt    60
tactgagacg aggggagaat caatgttgcc aacactgtca                          100

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
actccacttc aagtaagagt t                                              21

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
gcacggaata tgggactact tcg                                            23

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
agtcacatca agatcgttta tgg                                            23
```